US010058657B2

(12) United States Patent
Ulrich et al.

(10) Patent No.: US 10,058,657 B2
(45) Date of Patent: Aug. 28, 2018

(54) INJECTION DEVICES WITH ERGONOMIC ENHANCEMENTS

(71) Applicant: Eli Lilly and Company, Indianapolis, IN (US)

(72) Inventors: Michael Scott Ulrich, Columbus, OH (US); Andrew Vankirk Sweeney, Columbus, OH (US); Christopher H. Muenzer, Columbus, OH (US); Timothy M. Blum, Columbus, OH (US); Corrie Bennison, Lewis Center, OH (US); Christopher P. McKenzie, Lancaster, OH (US)

(73) Assignee: Eli Lilly and Company, Indianapolis, IN (US)

( * ) Notice: Subject to any disclaimer, the term of this patent is extended or adjusted under 35 U.S.C. 154(b) by 1071 days.

(21) Appl. No.: 14/355,590

(22) PCT Filed: Nov. 7, 2012

(86) PCT No.: PCT/US2012/063887
§ 371 (c)(1),
(2) Date: May 1, 2014

(87) PCT Pub. No.: WO2013/070715
PCT Pub. Date: May 16, 2013

(65) Prior Publication Data
US 2014/0296782 A1    Oct. 2, 2014

Related U.S. Application Data

(60) Provisional application No. 61/556,709, filed on Nov. 7, 2011.

(51) Int. Cl.
*A61M 5/31* (2006.01)
*A61M 5/32* (2006.01)
(Continued)

(52) U.S. Cl.
CPC .......... *A61M 5/3137* (2013.01); *A61M 5/158* (2013.01); *A61M 5/31* (2013.01);
(Continued)

(58) Field of Classification Search
CPC .............. A61M 5/3134; A61M 5/3143; A61M 2005/1586; A61M 5/3137; A61M 5/315; A61M 5/31511
See application file for complete search history.

(56) References Cited

U.S. PATENT DOCUMENTS

| 4,031,889 A | 6/1977 | Pike |
| 5,167,641 A | 12/1992 | Schmitz |

(Continued)

FOREIGN PATENT DOCUMENTS

| EP | 2221076 | 8/2010 |
| EP | 2489387 | 8/2012 |

(Continued)

OTHER PUBLICATIONS

European Patent Office Communication with Supplementary European Search Report and European Search Opinion pertaining to International Application No. PCT/US2012063887; dated Jul. 23, 2015.

(Continued)

*Primary Examiner* — Nathan R Price
*Assistant Examiner* — Melissa A Snyder
(74) *Attorney, Agent, or Firm* — Jonathan Anderson

(57) ABSTRACT

Injection devices with ergonomic enhancements are disclosed. Generally, the injection devices include large oversized grips, including flanges at the base end of the device for enhanced stability. Push-type and squeeze-type devices are described, as well as manual injectors and auto-injectors. Such injection devices are useful for delivering a fluid (e.g. medication) to a patient.

15 Claims, 45 Drawing Sheets

(51) Int. Cl.
*A61M 5/50* (2006.01)
*A61M 5/158* (2006.01)
*A61M 37/00* (2006.01)

(52) U.S. Cl.
CPC .......... *A61M 5/3134* (2013.01); *A61M 5/322* (2013.01); *A61M 5/3232* (2013.01); *A61M 5/3287* (2013.01); *A61M 5/5086* (2013.01); *A61M 37/0015* (2013.01); *A61M 2005/3139* (2013.01); *A61M 2205/586* (2013.01)

(56) References Cited

U.S. PATENT DOCUMENTS

| | | | |
|---|---|---|---|
| 5,304,128 A | | 4/1994 | Haber et al. |
| 5,645,824 A | | 7/1997 | Lim et al. |
| 6,086,568 A | | 7/2000 | Caizza |
| 6,086,569 A | | 7/2000 | Schweizer |
| 6,156,014 A | | 12/2000 | Petersen et al. |
| 6,200,291 B1 | | 3/2001 | DiPietro |
| 6,270,479 B1 | | 8/2001 | Bergens et al. |
| 6,332,875 B2* | | 12/2001 | Inkpen ................ A61M 5/3287 604/117 |
| 6,537,242 B1* | | 3/2003 | Palmer .............. A61M 37/0015 600/309 |
| 7,632,245 B1 | | 12/2009 | Cowan et al. |
| 7,713,244 B1 | | 5/2010 | Cherif Cheikh et al. |
| 7,988,663 B2 | | 8/2011 | Schiller et al. |
| 8,333,769 B2* | | 12/2012 | Browne ............. A61B 17/1615 606/185 |
| 8,430,862 B2* | | 4/2013 | Peyman ................ A61F 9/0017 604/301 |
| 2003/0229308 A1 | | 12/2003 | Tsals ....................... A61M 5/20 604/116 |
| 2005/0187522 A1 | | 8/2005 | Miller |
| 2007/0043335 A1* | | 2/2007 | Olsen ................ A61M 5/14276 604/890.1 |
| 2008/0269692 A1* | | 10/2008 | James ................ A61M 5/3202 604/198 |
| 2009/0054842 A1* | | 2/2009 | Yeshurun .......... A61M 37/0015 604/173 |
| 2009/0093787 A1* | | 4/2009 | Barbour .............. A61M 5/3137 604/506 |
| 2009/0227942 A1 | | 9/2009 | Stroem Hansen et al. |
| 2009/0259179 A1* | | 10/2009 | Hillios .................... A61M 5/46 604/110 |
| 2010/0030152 A1* | | 2/2010 | Lee ................... A61M 37/0015 604/131 |
| 2010/0069846 A1* | | 3/2010 | Stamp ................ A61M 5/2033 604/135 |
| 2010/0174225 A1 | | 7/2010 | Pesach et al. |
| 2011/0071492 A1* | | 3/2011 | Horvath ................ A61M 5/326 604/506 |

FOREIGN PATENT DOCUMENTS

| | | |
|---|---|---|
| JP | 2003509082 | 3/2003 |
| JP | 2009511177 | 3/2009 |
| JP | 2009519798 | 5/2009 |
| JP | 3167383 | 3/2011 |
| WO | 1995001198 | 1/1995 |
| WO | 199934850 | 7/1999 |
| WO | 20070047200 | 4/2007 |
| WO | 20070071485 | 6/2007 |
| WO | 2011047298 | 4/2011 |

OTHER PUBLICATIONS

Patent Cooperation Treaty International Search Report and the Written Opinion of the International Searching Authority pertaining to International Application No. PCT/US12/63887; dated Apr. 1, 2013.
Patent Cooperation Treaty International Preliminary Report on Patentability pertaining to International Application No. PCT/US2012/063887; dated May 13, 2014.
Office Action issued by the Japanese Patent Office pertaining to Japanese patent application No. 2014-540211.
Office Action issued by the Japanese Patent Office pertaining to Japanese patent application No. 2014-540211 dated Feb. 6, 2018.

* cited by examiner

750

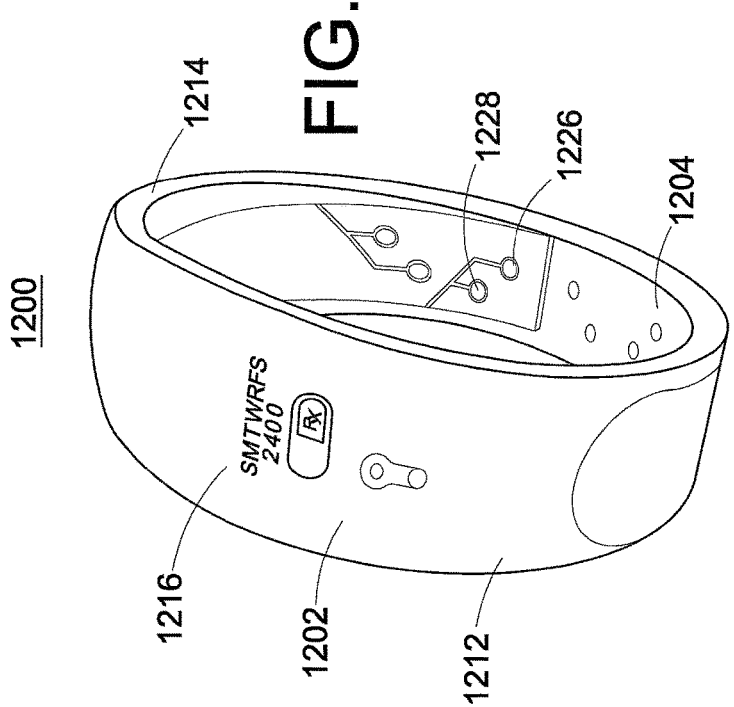
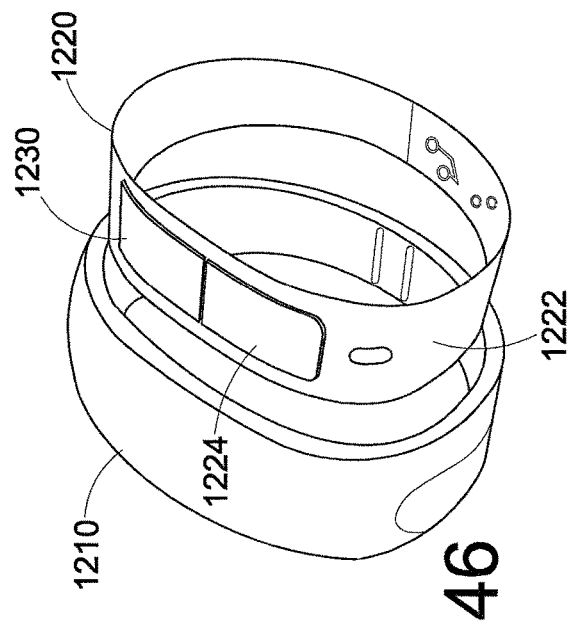
FIG. 45
FIG. 46

INJECTION DEVICES WITH ERGONOMIC ENHANCEMENTS

This application claims priority to U.S. Provisional Patent Application Ser. No. 61/556,709, filed Nov. 7, 2011, the disclosure of which is hereby incorporated by reference in its entirety.

BACKGROUND

The present disclosure relates generally to drug delivery technology including injection devices that are modified to be more easily used. Such devices include manual syringes, autoinjectors, and related fluid delivery apparatuses. Various structures, methods of making, and methods of using such injection devices are also disclosed.

Several drugs, vaccines, medications, therapeutic agents, diagnostic agents, etc. are administered via injection devices such as manual syringes and auto-injectors. This preferably occurs under sterile conditions. Generally, such devices include a barrel or tube containing a formulation, and a piston (such as a rubber piston) for ejecting the formulation in the barrel through a hollow injection needle. The needle pierces the skin into the body and delivers the substance by various routes such as intravenously, intramuscularly, subcutaneously, etc. The motive force for ejecting the formulation can be manual (e.g. pushing the thumb down on the device) or mechanical (e.g. a spring, a battery, etc.). The piston is pushed along the inside of the barrel, allowing the fluid (liquid or gas) to be expelled through an orifice at the end of the tube fitted with a needle, such as a hypodermic needle. Several medications are commonly self-administered by laypersons, for example in the administration of insulin by diabetics. Such self-administration reduces costs, increases convenience to the patient, and increases patient compliance.

Current syringe and auto-injector form factors and ergonomics are designed for a general patient population. For example, the user interfaces and control surfaces, such as the fingerflange on the barrel and the thumbrest on the plunger, are rather small. The plunger of a syringe is also vertically oriented. While suitable for a large majority, these traditional designs present challenges in handling and operation to a minority of patients, and may lead to use errors that become barriers to effective self-injection treatments. In particular, patients with finger/hand deformities or with reduced strength, dexterity, or coordination can find traditional syringes and auto-injectors difficult to use. These symptoms and conditions are common in people with rheumatoid arthritis (RA), multiple sclerosis (MS), who may otherwise be able to self-administer such medications.

BRIEF DESCRIPTION

The injection devices of the present disclosure are targeted for users with deficiencies and limitations in manual dexterity, coordination, and strength, for example users with symptoms of rheumatoid arthritis (RA), multiple sclerosis (MS), and other such conditions/diseases. The injection devices generally contain integral ergonomic features to address difficulties with handling and operating the device, as well as features to provide a stable platform. One common theme is appropriate sizing of the housings and control features so that they can be effectively handled. Prominent interfaces are useful in this regard. These injection devices are useful for delivering a fluid, such as medication, to a patient.

Disclosed in some embodiments is an injection device, comprising: a housing having a barrel located within the housing for containing a fluid, a top end with an opening for receiving a portion of a plunger within the barrel, and a base end that has an orifice for dispensing the fluid from the barrel; a lower flange extending radially from the base end of the housing; wherein the plunger has a gripping end with an external grip extending from the housing and a second end movably positioned within the barrel such that when the external grip is depressed towards the lower flange, fluid is dispensed by the plunger through the orifice.

The injection device may further comprise an auto-retracting needle.

The housing may be transparent or contain a viewing window for viewing the interior of the housing. The housing may include graduated marks indicating the volume of fluid contained within the housing.

The lower flange may be a deformable material capable of creating suction when the plunger is pulled away from the housing. The housing may have a right circular conical shape.

The injection device may further comprise a plunger handle, the plunger handle comprising a shaft, a gripping end that extends from the top end of the housing, and a latching end adapted to push the piston through the barrel. The gripping end of the plunger handle may include a ring shaped grip. In general embodiments, the plunger handle is pulled away from the housing, then pushed into the housing to insert a needle and dispense fluid from the barrel.

The barrel may comprise a needle end with a needle, a plunger end, a forward surface at the needle end for interacting with a return spring, and a fingerflange extending radially at the plunger end, the barrel being seated within a lower channel at the base end of the housing. An inner sleeve may be present at the base end, the return spring being located between a lower channel sidewall and the inner sleeve.

The injection device may further comprise a penetration drive, the penetration drive comprising a plunger sleeve with a front surface for contacting the fingerflange and an inner channel, and the penetration drive resting upon a separation spring located within the lower channel.

The injection device may further comprise an upper channel piece that surrounds the lower channel, an injection head extending from an interior top surface of the upper channel piece, the injection head having a U-shaped form with laterally flexible legs and forming a cavity therebetween.

The lower channel may include a guide surface that interacts with the injection head to alternately flex the legs inwards and outwards.

A lower end of the upper channel piece may taper towards the lower channel.

The piston is generally attached to a first end of a plunger shaft, the plunger shaft extending through the front surface of the plunger sleeve, a second end of the plunger shaft including a thumbrest upon which the injection head can push to depress the piston within the barrel.

The injection device may further comprise a plunger handle, the plunger handle comprising a shaft, a gripping end that extends from the top end of the housing, and a latching end adapted to push the piston through the barrel. The upper channel piece may include a groove that is complementary to the latching end of the plunger handle.

The injection device might include a string that connects the lower flange to the plunger handle to create suction.

Alternatively, the plunger handle includes a tunnel such that when the plunger handle is pulled upwards, suction is created.

The width of the lower flange may be at least twice the width of the base end of the housing.

In some embodiments, the piston is a bottom end of an inner barrel, the inner barrel containing a second piston slidably received within the inner barrel.

In some other embodiments, the gripping end of the plunger includes a shell that surrounds the housing, the shell having a bottom end and the top end, the top end of the housing being slidably received within the bottom end of the plunger shell; and the external grip protrudes from a side of the plunger shell. A stop may be included to prevent the bottom end of the plunger shell from contacting the lower flange. The external grip may include two rings. The plunger shell may taper inwards between the bottom end and the top end.

Such embodiments as described above may share some common features.

The injection device may further comprise a needle that is inserted when the external grip is pushed downwards towards the lower flange. The needle may be an auto-retracting needle. The housing may be transparent or contain a viewing window for viewing the interior of the housing. The external grip may be ring shaped. The width of the lower flange may be at least twice the width of the base end of the housing. The injection device may further comprise a visual indicator for indicating whether the injection device has been used, such as a chemical color change.

Disclosed in some other embodiments is an injection device, comprising: a housing having a top end and a base end that has an orifice for dispensing the fluid from the barrel; a hull within the housing having a lower end and an upper end, wherein the hull contains a barrel for containing a fluid, a plunger slidably received within the barrel, and an injection drive; a lever extending radially from the lower end of the hull through the housing; an external grip which is an upper flange attached to the lever outside the housing; and a biasing mechanism biasing the hull away from the base end of the housing; wherein when the upper flange is depressed towards the lower flange, fluid is dispensed from the barrel through the orifice.

The upper flange may be an annulus. The biasing mechanism may comprise a return spring and an inner sleeve, the return spring being located between the inner sleeve and a housing sidewall. The housing may include one or more shafts through which the lever passes. The housing may have a cylindrical or elliptical shape. Sometimes, the housing includes a stop surface to prevent the upper flange from contacting the lower flange. Other times, the upper flange can contact the lower flange when fully depressed.

Disclosed in other embodiments is an injection device, comprising: a housing having a top end and a base end, wherein a needle can protrude from the base end; a lower flange extending radially from the base end of the housing; a barrel located within a lower channel of the housing for containing a fluid to be dispensed; a needle attached to the barrel and oriented to be able to protrude from the base end; a penetration drive for inserting the needle and pushing the piston through the barrel; a piston slidably received within the barrel; a plunger handle having a gripping end that extends from the top end of the housing and having a latching end adapted to latch to an upper channel piece; and an upper channel piece adapted to activate the penetration drive.

Also disclosed is an injection device, comprising: a housing having a top end, a base end, and a first side surface, and an orifice in the base end; an ampoule located within the housing for containing a liquid to be dispensed by the injection device; a lever extending from the first side surface of the housing for squeezing the ampoule to dispense liquid; and a safety interlock biased to extend from the base end of the housing and prevent the first lever from being pushed until the safety interlock is disengaged.

The safety interlock may comprise an annular ring and a blocking wall extending transversely from the annular ring. The blocking wall may include a stop face at an upper portion and a channel at a middle portion. The lever may include a key that passes through the channel when the safety interlock is disengaged.

The housing may be transparent or contain a viewing window for viewing the ampoule. The top end of the housing may include a visual indicator for indicating whether the injection device has been used. The visual indicator may be a window in the top end, and wherein an upper end of the lever moves a color segment from a non-visible location to a visible location viewable through the window. Alternatively, the visual indicator may be a chemical color change.

The first lever further may include a safety trigger to prevent lateral motion of the lever after the safety interlock is disengaged. In certain embodiments, the safety trigger comprises an outer surface extending through a slot in the first lever, a stop arm that engages the first lever, and a catch arm extending towards the housing; and wherein the housing comprises a safety cavity and a stop surface that engages the catch arm.

The first lever may be biased away from the housing by a torsion spring. The blocking wall of the safety interlock may be a continuous wall, or one or more discrete walls. A compaction wall may be located within the housing adjacent to the ampoule, wherein the lever pushes the compaction wall against the ampoule to dispense liquid.

In some embodiments, the injection device has two levers extending from opposite side surfaces of the housing, and the safety interlock prevents both levers from being pushed until the safety interlock is pushed towards the base end of the housing.

Also disclosed is an injection device, comprising: a housing having a top end, a base end, a first side surface, and a second side surface opposite the first side surface, wherein a needle can protrude from the base end; an ampoule located within the housing for containing a liquid to be dispensed by the injection device; and a first lever extending from the first side surface and a second lever extending from the second side surface of the housing for squeezing the ampoule to dispense liquid; and a safety interlock biased to extend from the base end of the housing and prevent the two levers from being pushed until the safety interlock is disengaged.

The safety interlock may comprise an annular ring and two channels, and the first lever and the second lever each comprise a key that passes through one channel when the safety interlock is disengaged. The two channels may be present on opposite sides of a continuous wall extending transversely from the annular ring. Alternatively, one channel is located in a first blocking wall extending transversely from the annular ring, the other channel is located in a second blocking wall extending transversely from the annular ring, and the first and second blocking walls extend from opposite sides of the annular ring.

The injection device may further comprise two compaction walls located on opposite sides of the ampoule and biased away from the ampoule, wherein the levers engage the two compaction walls to squeeze the ampoule.

The top end may include a upper window for indicating whether the injection device has been used.

Further disclosed in embodiments is an injection device, comprising: a housing having a base end and a top end; a hook extending from a rear end of the top end of the housing; and an actuation button on a front end of the top end of the housing opposite the hook.

An auto-inserting needle can extend from the base end of the housing. A penetration drive may be present inside the housing for inserting a needle and dispensing fluid in a barrel through the needle.

The rear surface of the housing may be complementary to an inward surface of the hook. The actuation button may move towards the rear end upon being pushed. The housing may be transparent or contain a viewing window for viewing the interior of the housing.

Described in other embodiments is an injection device, comprising: a housing having a base end and a top end, wherein a needle can protrude through the base end; a lower flange extending radially from the base end of the housing; a hull within the housing having a lower end and an upper end; a lever extending radially from the lower end of the hull through the housing; an upper flange attached to the lever outside the housing; a biasing mechanism biasing the hull away from the base end of the housing; and the hull containing a barrel, a plunger slidably received within the barrel, and an injection drive for automatically ejecting a fluid through a needle.

The biasing mechanism may comprise a return spring and an inner sleeve, the return spring being located between the inner sleeve and a housing sidewall.

The plunger may comprise a shaft, a piston at a bottom end of the shaft, and a thumbrest at a top end of the shaft. The hull can include a locking mechanism biased to remain between the piston and the thumbrest, and include a drive spring acting between the thumbrest and the upper end of the hull.

The lower end of the hull may include a passage, wherein the base end of the housing includes an inner sleeve that can extend through the passage to disengage the locking mechanism in the hull.

The housing may include one or more shafts through which the lever passes. The upper flange may be an annulus. The housing may be transparent or contains a viewing window for viewing the interior of the housing. The housing may have an cylindrical or elliptical shape.

The housing may include a stop surface to prevent the upper flange from contacting the lower flange. Alternatively, the upper flange can contact the lower flange when fully depressed.

Also disclosed in embodiments is an injection device, comprising: a housing having an upper end and a lower end; a hull surrounded by the housing, a base of the hull extending beyond the lower end of the housing, wherein a needle can be extended from the base of the hull, and wherein the hull contains a fluid to be dispensed; and a grip at the upper end of the housing.

The lower end of the housing may contain a cutout or a transparent window for viewing the hull. The hull may be transparent. Sometimes, the hull contains a fluid chamber, a piston at an upper end of the fluid chamber, and a penetration drive for pushing the piston through the fluid chamber.

Also described herein in different embodiments is an injection device, comprising: a barrel having an upper end and a lower end; a vial having an upper end and a lower end, the upper end of the vial engaging the lower end of the barrel, and a needle being located at the lower end of the vial; a push button extending from an upper surface of the barrel; two handles extending from opposite sides of the barrel, each handle being formed from a strand that is bent to make three sides; and a twist ring on an external surface of the barrel for controlling whether the push button can be depressed.

The injection device may further comprise a needle cap. Sometimes, the needle cap is labeled with a 1, the twist ring is labeled with a 2, and the push button is labeled with a 3.

The two handles may extend from a lower portion of the barrel, when the twist ring is located on an upper portion of the barrel. The two handles can have an arcuate curve towards the lower end of the barrel.

The injection device may further comprise a piston at the lower end of the barrel.

The push button is generally part of a plunger. In some embodiments, the barrel contains two chambers, with the plunger and the twist ring cooperating to maintain separation between the two chambers.

Also described herein is a wearable injection device, comprising: a control interface that forms an outer surface of the device; and a medication band that forms an inner surface of the device, the medication band containing a microchip, a medication reservoir, and microneedles connected to the reservoir.

The medication band can also contain sensors. The control interface can also contain an electronic display. The control interface includes an exterior surface and two side surfaces that cooperate with the medication band.

Also described herein is an injection device, comprising: a hull having an upper end and a lower end, wherein a needle can extend from the lower end of the hull; a bulb at the upper end of the hull, the bulb having two opposite squeezable quadrants and two rigid quadrants; and an outer twist ring surrounding the hull, the outer twist ring including a contoured shell conforming to the bulb and two cutout sections that expose the quadrants of the bulb, wherein the outer twist ring covers the squeezable quadrants in a first position and exposes the squeezable quadrants in a second position.

Sometimes, the outer twist ring extends from the upper end of the hull to the lower end of the hull, and the two cutout sections extend from a lower end of the twist ring to a height sufficient to expose the quadrants of the bulb.

The injection device may further comprise a flange extending radially from the lower end of the hull. Sometimes, the hull is transparent. In some embodiments, a top of the outer twist ring includes a cutout or transparent window that exposes a display in the hull.

The present disclosure also describes various embodiments of an injection device, comprising: a housing; a pump located within the housing, the pump comprising a reagent chamber, a reaction chamber, and a fluid chamber, the reagent chamber being fluidly connected to only the reaction chamber, the reaction chamber being fluidly connected to the fluid chamber by a passage, and the fluid chamber including an outlet connected to a needle that extends from a bottom surface of the housing; a button located above the reagent chamber; and an adhesive patch on a bottom surface of the housing.

The injection device may further comprise a protective layer covering the pump. The injection device may alternatively further comprise a thin film covering the adhesive patch, the thin film including a pull tab.

The housing can be formed from a top piece and a bottom piece. In particular embodiments, the reagent chamber is oriented in a longitudinal axis, and wherein the reaction chamber and the fluid chamber are oriented in a radial axis.

Also described in various embodiments is an injection device, comprising: a housing having a top surface, a bottom surface, and a side surface; the top surface having a display and an injection button; and an injecting site located on the bottom surface. The injection device may further comprise a secondary button on the side surface. The injecting site can comprise a patch of microneedles attached to a reservoir inside the housing.

Described herein in different embodiments also is an injection device, comprising: a housing having a top side and a front side; a carrying handle on the top side of the housing; a sliding door on the front side of the housing that extends from the top side when in an open position, the sliding door including a display; and an outlet for delivering fluid located on the housing. The housing can have a rectangular shape with rounded surfaces and corners.

Various embodiments of another injection device are disclosed which comprise: a flexible substrate; a patch of microneedles; and a drug reservoir connected to the path of microneedles.

The flexible substrate can be in the form of a wristband having an inner surface and an outer surface, the drug reservoir being located within the substrate, the patch of microneedles being located on the inner surface; and the device further comprising an electronic display on the outer surface.

Alternatively, the drug reservoir and the patch of microneedles can be part of an injection pad which is attached to the flexible substrate. The injection device can include a plurality of injection pads. Sometimes, the plurality of injection pads includes a plurality of different shapes. Sometimes, the flexible substrate has a rectangular shape. A fastener can be located on one end of the injection device that cooperates with another fastener on the substrate. The injection device occasionally further comprises a communications port or a wireless communications link.

These and other non-limiting aspects and/or objects of the disclosure are more particularly described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIG. 45 is a perspective assembled view of an eighth exemplary embodiment of an injection device of the present disclosure, which is a wearable device with two components.

FIG. 46 is a perspective exploded view of the eighth exemplary embodiment showing the two components separated from each other.

DETAILED DESCRIPTION

Figure 1:
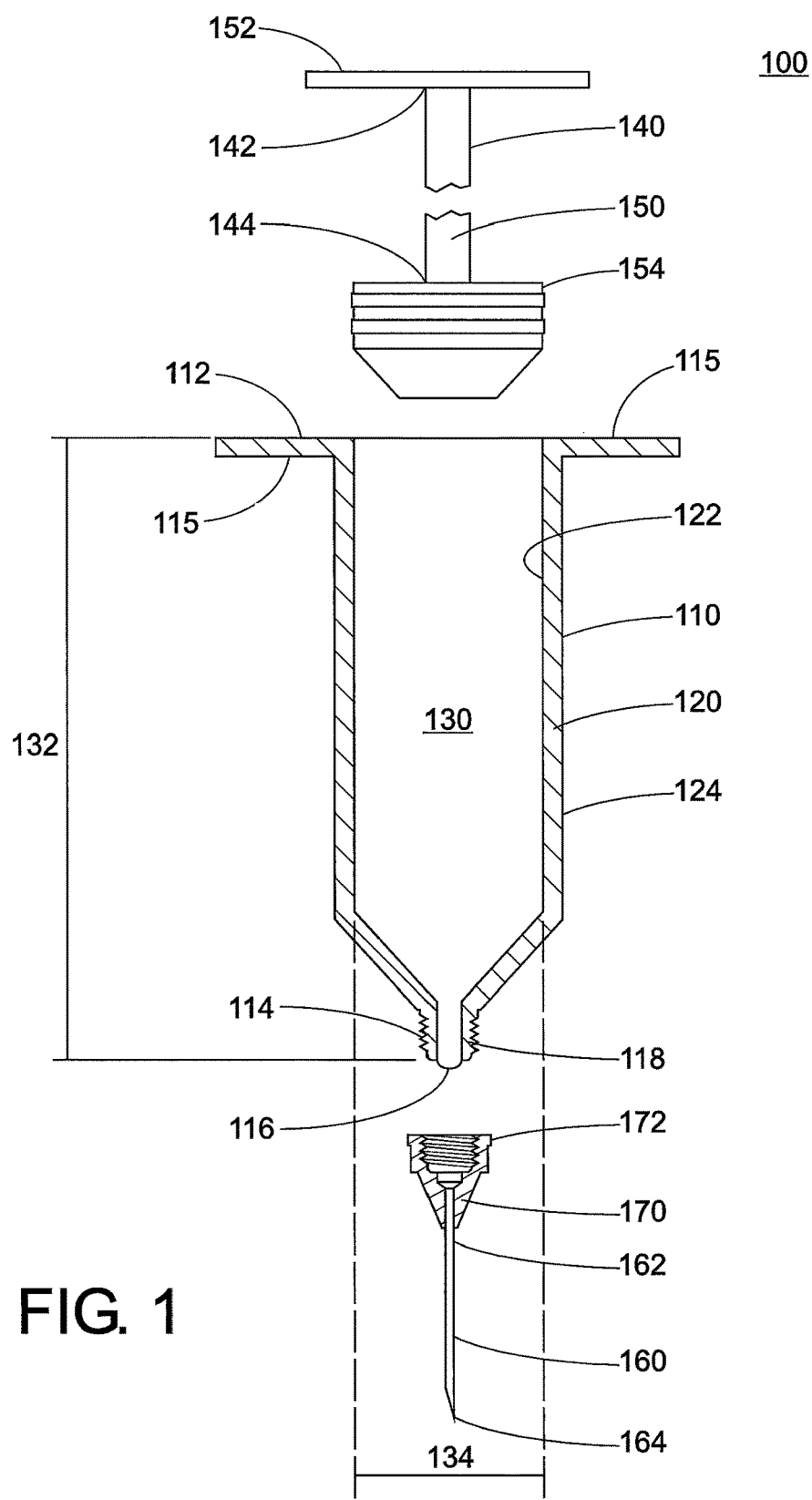
FIG. 1 is a diagram showing the components of a traditional syringe.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. In the following specification and the claims which follow, reference will be made to a number of terms which shall be defined to have the following meanings.

The singular forms "a," "an," and "the" include plural referents unless the context clearly dictates otherwise.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "internal" and "external" are relative to a surface, and should not be construed as requiring a particular orientation or location of the structure. Similarly, the terms "upper", "lower", "top", "bottom" are relative to each other in location, i.e. an upper component is located at a higher elevation than a lower component.

Initially, FIG. 1 is a diagram showing the various components of a traditional hypodermic syringe 100. An explanation of each component and its function can be helpful in understanding the injection devices of the present disclosure. In this regard, the syringe includes a barrel 110, a plunger 140, and a needle 160.

The barrel 110 is the part of the hypodermic syringe that contains the fluid to be injected into a patient, and also defines the path through which the plunger 140 will travel. The barrel 110 is hollow, cylindrical, and has a plunger end 112 and a needle end 114. The plunger end may also be referred to as a closed end 112 of the barrel, because fluid will not pass through this end when the plunger 140 is inserted. Similarly, the needle end may also be referred to as an open end 114 of the barrel because fluid can pass through this end when the needle 160 is attached. The barrel is formed from a sidewall 120 that surrounds an interior space 130. The sidewall 120 includes an interior surface 122 and an exterior surface 124. The barrel itself is usually transparent for viewing of fluid within the interior space, and a scale can also be imprinted on the exterior surface. The needle end 114 can be tapered towards an orifice 116 through which fluid exits the interior space 130. The length 132 and diameter 134 of the barrel are variable, though they come in various standard sizes. The needle end 114 also includes a female fitting 118 to form a leak-free connection with the needle 160. The plunger end 112 also includes a fingerflange 115 which flares out from the barrel, and allows the user to press on the plunger 140 with the thumb while holding the barrel in place with two fingers.

The plunger 140 is used to discharge fluid present in the barrel 110 of the syringe. The plunger 140 includes a shaft 150 with a thumbrest 152 on one end 142 and a piston 154 on the other end 144. The shaft is long enough for the piston 154 to travel the length of the interior space 130 of the barrel. The piston 154 fits snugly against the interior surface 122 of the barrel to make an airtight seal. A lubricant (not visible) may be present between the piston 154 and the interior surface 122 of the barrel to reduce the gliding force.

The needle 160 is essentially a small thin tube, and is the part of the syringe that actually pierces the skin of the patient. On one end 162 is a hub 170, which includes a male fitting 172 for attachment to the needle end of the barrel, such as a Luer lock. The other end of the needle 164 is beveled to increase the ease of insertion into the patient.

As described within, the injection devices of the present disclosure generally contain integral ergonomic features that make them easier to handle and operate. Several different exemplary embodiments are presented. The injection devices typically include a barrel or other container for the fluid to be dispensed, and a plunger of various construction. It is contemplated that the injection device may be offered with or without a needle. For example, the injection device may be a single-use device, or a multiple-use device in which the needle may be replaced. Needles are also offered in various sizes, and the injection device can be modified to operate with such different sizes, as described further herein. For the purposes of this disclosure, the term "injection device" is used to refer to manual syringes, auto-injectors, and infusion pumps of any size or shape.

FIGS. 2-13 depict a first exemplary embodiment of an injection device of the present disclosure. Here, the user interface includes a plunger with a ring-shaped interface, as well as a wide flange at the base that functions as a hand rest for stabilizing the device on the injection site. Operated using two hands, this approach provides additional stability while self-administering an injection. This also minimizes a person's need to use fine motor control to operate the device, in contrast with a traditional syringe.

Figure 2:
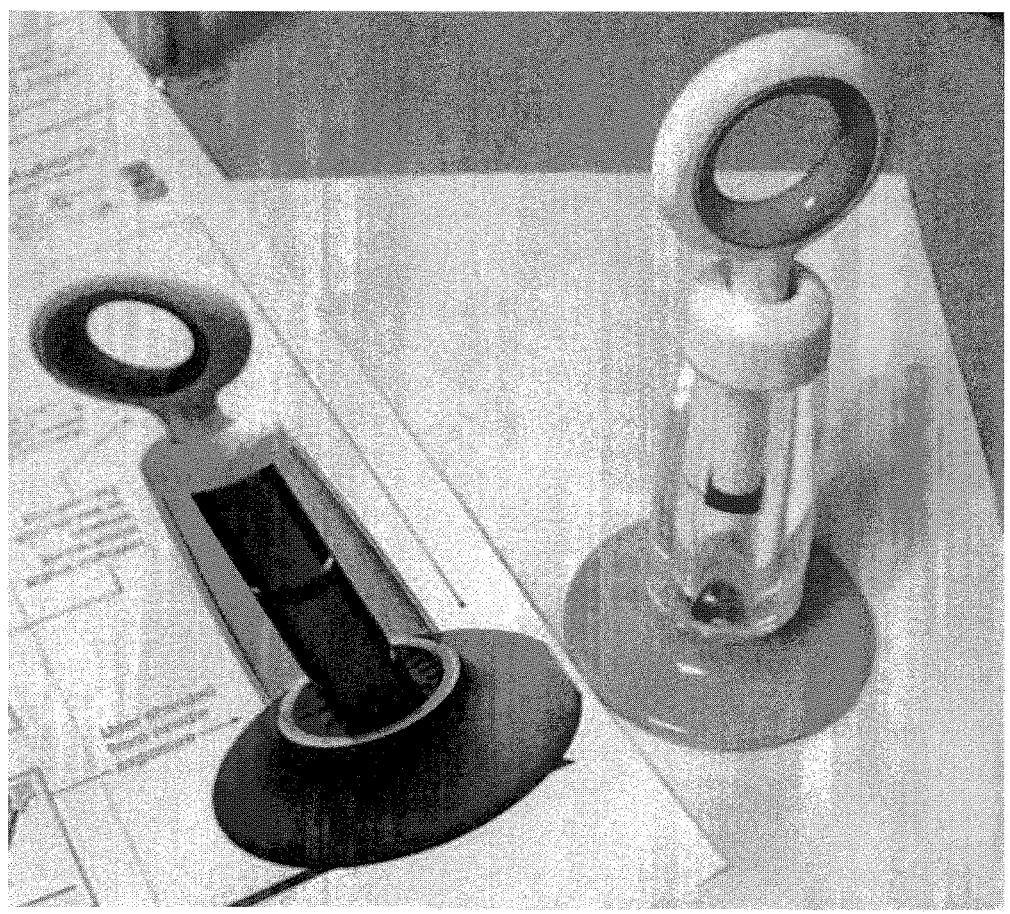
FIG. 2 is a perspective view showing a first exemplary embodiment of an injection device of the present disclosure.
Figure 3:
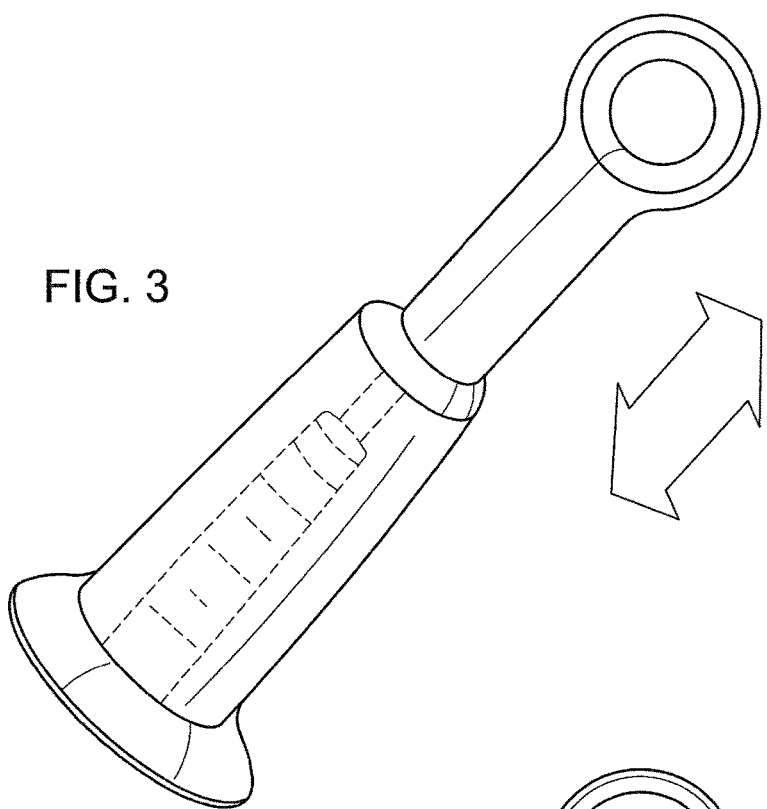
FIG. 3 is a perspective view of the first exemplary embodiment showing the motion of the plunger handle relative to the housing.

FIG. 2 is a perspective view depicting an embodiment of this first exemplary injection device. The device includes a housing. At the base of the housing is a flange extending away from the housing. The plunger having a ring-shaped plunger grip extends from the top of the housing. As seen in these two figures, the flange and the plunger grip have different colors from the rest of the device, which indicate that these surfaces are for users to hold onto. In addition, the oversize interface features aid in the handling of the device. It is contemplated that the flange and the plunger grip may be made from a soft-touch rubber material for comfort. The housing can be transparent, providing a clear view of the contents of the injection device as well as allowing the user to monitor the progress of the injection. As illustrated generally in FIG. 3, the plunger can be moved up and down in the vertical direction.

Figure 4:
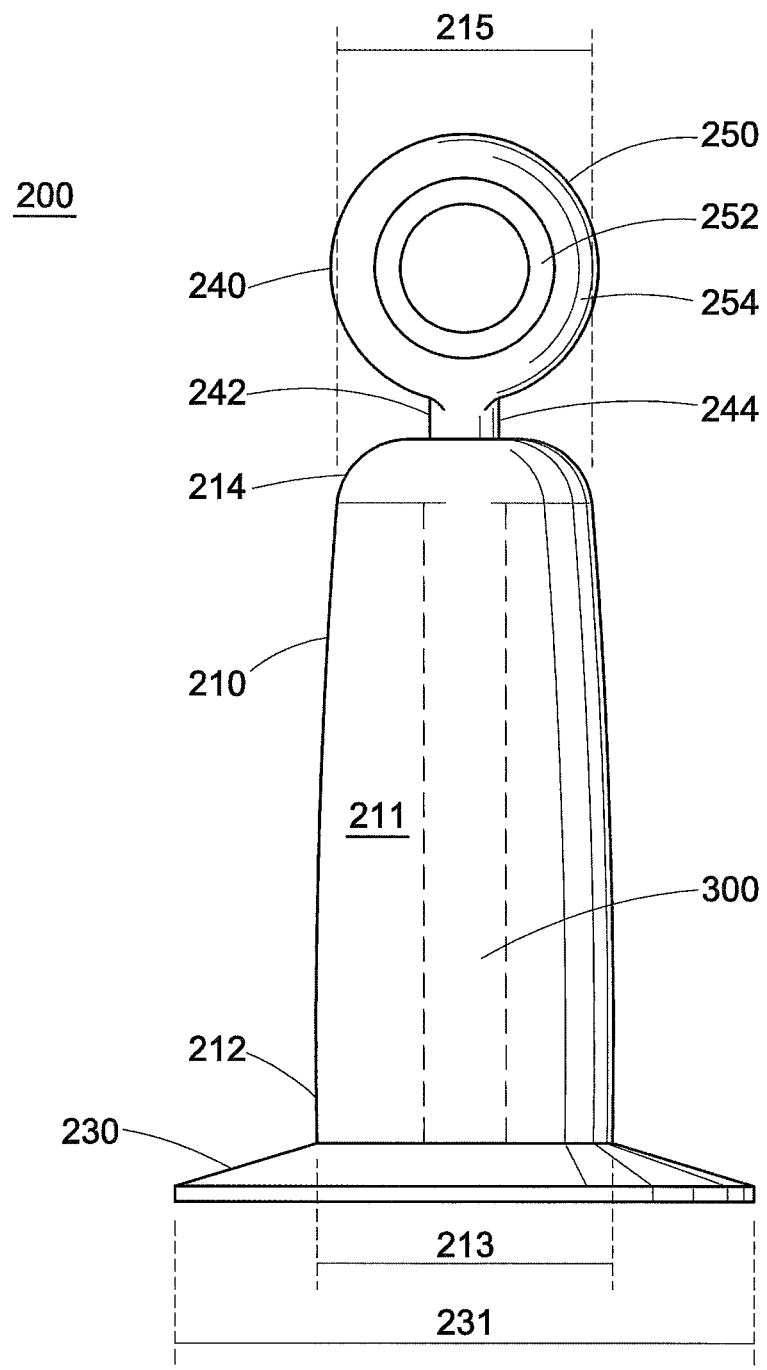
FIG. 4 is an exterior side view of the first exemplary embodiment in an initial state.

FIG. 4 is a side view of this injection device. The device 200 includes a housing 210 which has a base end 212 and a top end 214. The housing can generally be any shape, such as cylindrical, elliptical, rectangular, square, etc, when considered from a top view. However, the housing is depicted here as having a right circular conical shape, or the shape of a frustum. The width 213 of the base end 212 is greater than the width 215 of the top end 214. This is a convenient ergonomic shape that does not require the device to be held in a particular orientation during usage. Alternatively, the housing may be cylindrical or elliptical. Please note that the axis of the injection device runs from the base end to the top end, with the base end being placed on the user.

A lower flange 230 extends radially from the base end of the housing 210, and serves as the hand rest discussed above. The lower flange here is depicted as having a full disk shape and being located below the base end of the housing 210. However, the lower flange could alternatively have an annular shape and be located around the housing at the base end. The lower flange is intended to provide a wide base to stabilize the housing. It should be noted that the lower flange extends around the entire base end. In embodiments, the width 231 of the lower flange 230 is at least twice the width 213 of the base end 212 of the housing 210. If the housing 210 and the lower flange 230 are cylindrical, the width would correspond to the diameter. The width of a person's thumb is typically between 0.5 inches to 1 inch. In embodiments, the width 231 is from about 2 inches to about 4 inches, including about 2.5 inches. It should be noted that the width 213 at the base end 212 of the housing 210 will always be greater than the width 215 at the top end 214 of the housing 210, because this increases stability.

The plunger handle 240 includes a shaft 242 and a gripping end 244 that extends from the top end 214 of the housing. Put another way, the gripping end 244 is outside of or external to the housing 210. The gripping end 244 includes an external grip 250, which is shown here as being ring shaped. The grip 250 is divided into an internal grip surface 252 and an external grip surface 254. As discussed above, the internal grip surface 252 and the lower flange 230 are colored to indicate that they are surfaces for the user to hold onto. In embodiments, the grip may have an outer diameter (roughly equivalent to width 215) of about 1 and 5/8 inches, and the inner diameter of the grip may be about 7/8 inches.

The housing 210 may be transparent (indicated at reference numeral 211), or may contain a viewing window for viewing the interior of the housing. Inside the housing 210 is a barrel, indicated generally at reference numeral 300. The barrel contains a fluid to be dispensed, and the transparent housing or viewing window allows the user to monitor the progress.

Figure 5:
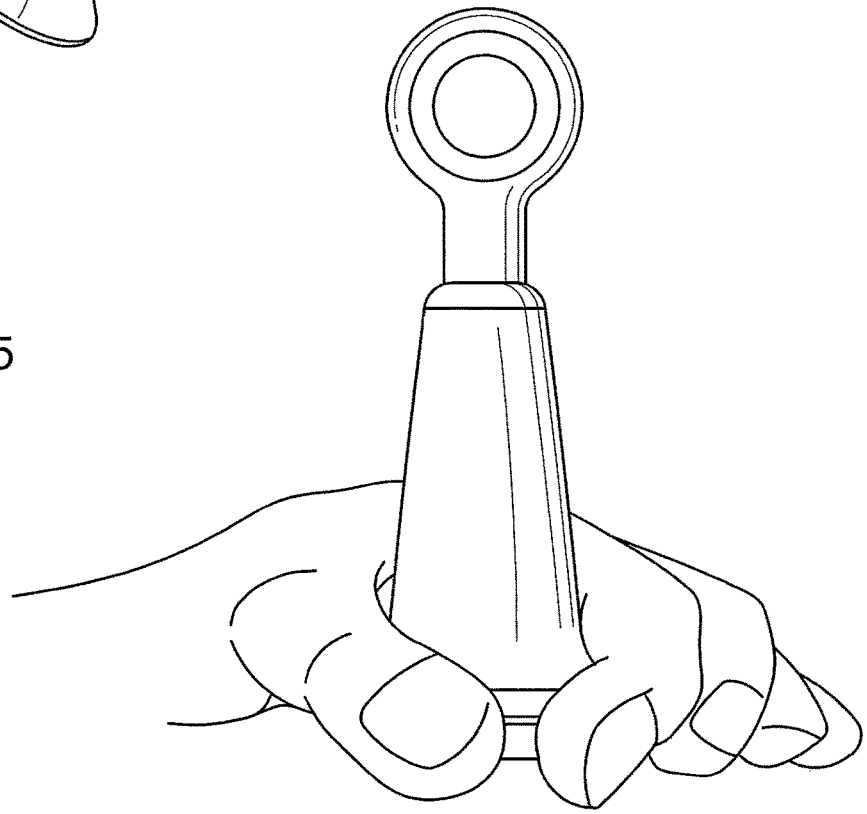
FIG. 5 is a diagram illustrating how a user's hand engages a lower flange on the first exemplary embodiment of an injection device of the present disclosure.
Figure 6:
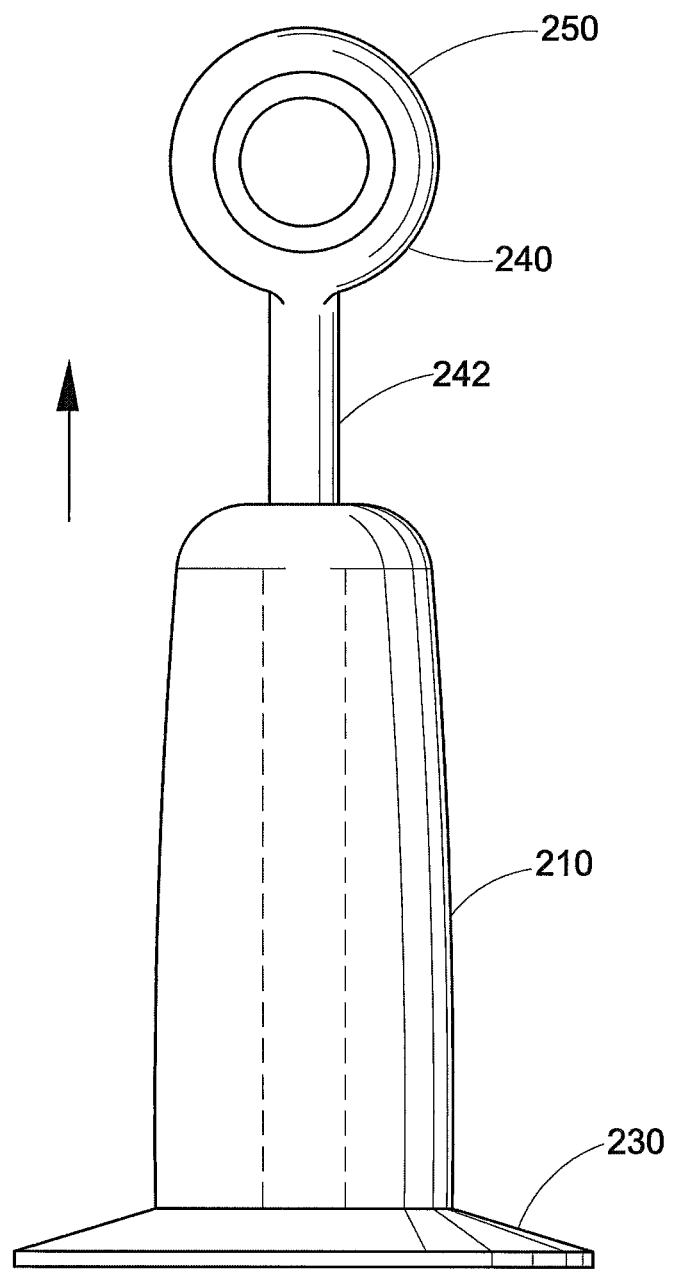
FIG. 6 is an exterior side view of the first exemplary embodiment with the plunger handle being pulled upwards.
Figure 7:
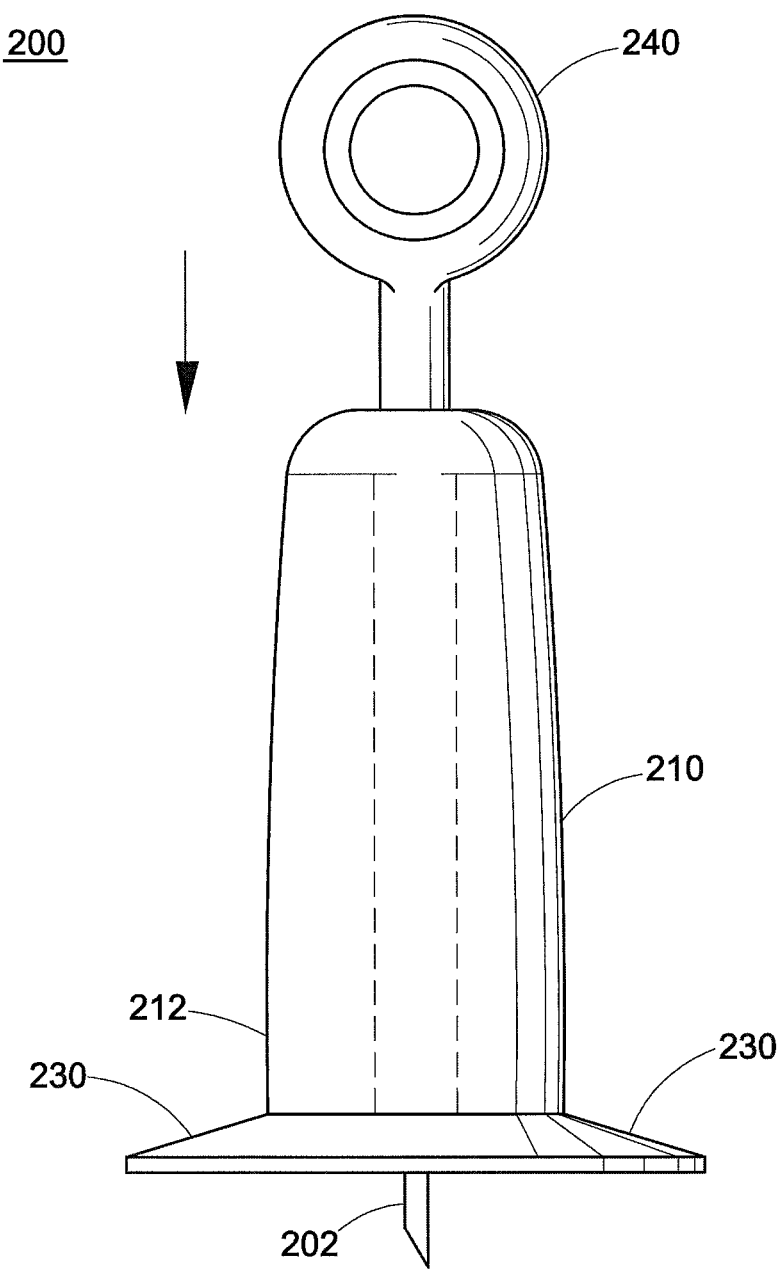
FIG. 7 is an exterior side view of the first exemplary embodiment with the plunger handle being pushed downwards into the housing. A needle is shown protruding through the housing.

Generally, the user operates the device by placing the device at the desired injection site. As seen in FIG. 5, the injection device 200 can be held in place by placing one hand on the wide flange. As illustrated in FIG. 6, the user then pulls the plunger handle 240 upwards in a vertical direction using the other hand. In some embodiments, it is contemplated that the lower flange can be made from a deformable rubber material so that when the plunger handle is pulled upwards, the lower flange will seal against the skin and provide suction. This is similar to pinching the skin prior to injection. Next, as illustrated in FIG. 7, the user pushes the plunger handle 240 into the device 200 to start the injection process. Put another way, the external grip is pushed downwards towards the lower flange. This pushing motion can be used to insert a needle to a predetermined depth and dispense the contents of the device through the needle. The needle 202 protrudes through the base end of the housing 210 and beyond the lower flange 230. The user can control the speed of the delivery of the contents as desired. At the end of the push stroke when the fluid is completely dispensed, the device subsequently shields the user from the needle to minimize exposure. The needle should automatically retract into the housing, and the plunger cannot be subsequently moved.

This injection device may be made in the form of an auto-injector where the needle is automatically inserted and the fluids dispensed, either upon pulling the plunger handle upwards beyond a threshold point or upon pushing the plunger handle downwards beyond a threshold point. Such devices are known in the art.

In particular embodiments, however, this injection device is contemplated to be a manual syringe and operated by two hands. This allows the user to control the speed of injection by varying the speed at which the plunger handle is depressed back into the housing 210. Different aspects of injection can affect various users, and controlling the injection speed allows each user to control their experience to minimize any pain or discomfort. For example, one user might prefer to inject slowly so that the fluid injection does not hurt, while another user might prefer to inject quickly so the needle can be removed. Put another way, the plunger handle 240 is pulled away from the housing 210, and then pushed into the housing 210 to insert the needle 202 and dispense fluid from the barrel 300 through the needle.

FIGS. 8-13 are side views showing the interior of the housing 210 through the different motions of using the injection device. These figures provide one example of an injection mechanism which can be used for manual injection. As depicted here, the mechanism also includes an auto-retracting needle.

Figure 8:
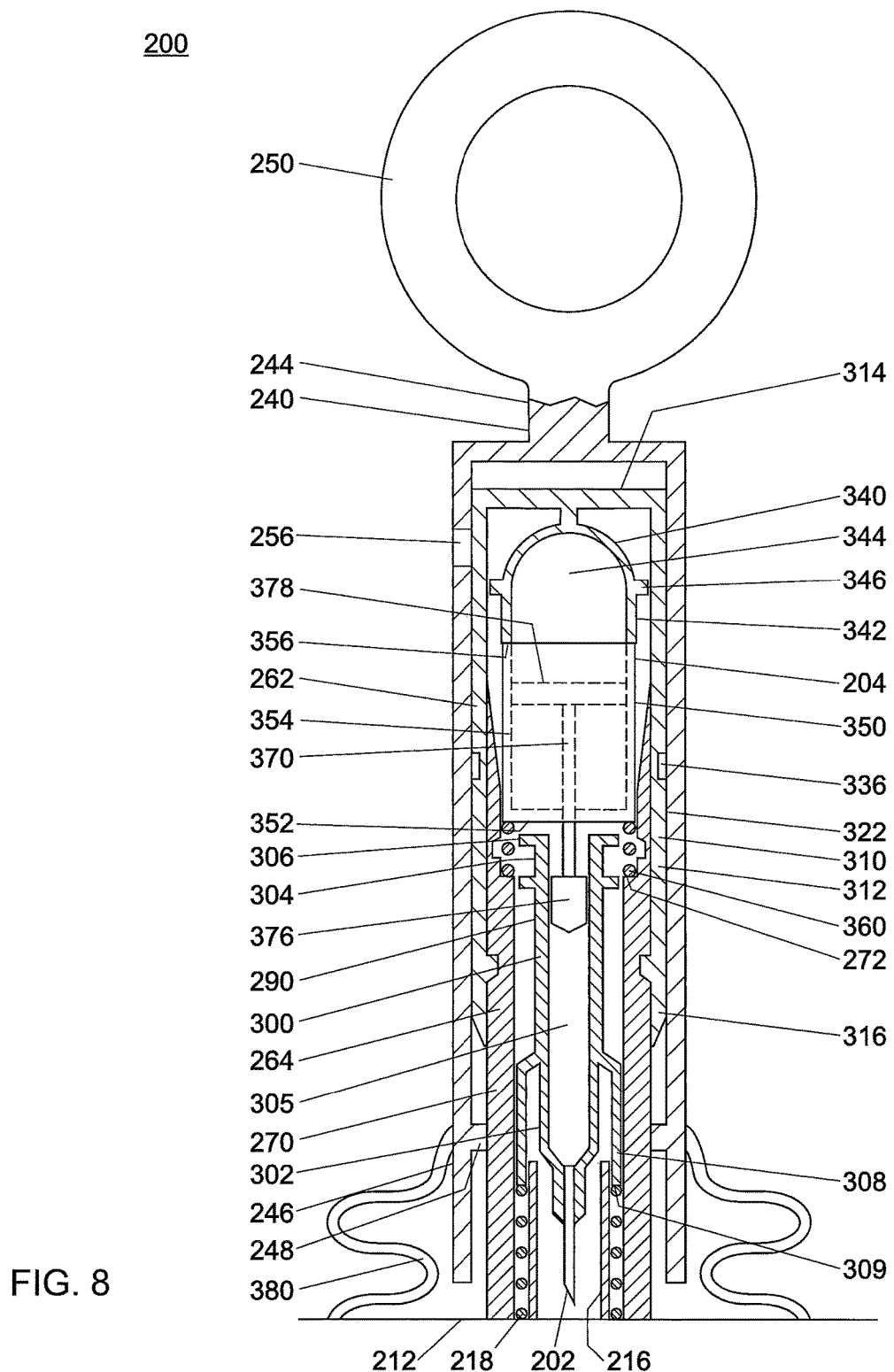
FIG. 8 is an interior cross-sectional view of the first exemplary embodiment of an injection device of the present disclosure, showing the internal components in an initial state.

FIG. 8 shows the injection device 200 (and the mechanism) in its initial state. The plunger handle 240 comprises a hollow shaft 242 (see FIG. 9), a gripping end 244 having a grip 250, and a latching end 246. As shown here, the latching end 246 includes a tongue 248. As explained further, the latching end 246 is adapted to push a piston 376 through the barrel 300 and dispense fluid through the needle 202 through interaction with other components.

The plunger handle 240 surrounds a channel 260 including an upper channel 262 and a lower channel 264. Extending from the base end 212 of the housing 210 is a lower channel sidewall 270, which generally defines the lower channel. Seated within the lower channel sidewall 270 is an injection assembly 290. The injection assembly 290 includes the barrel 300 and the needle 202. The barrel 300 has a needle end 302 and a plunger end 304, with the needle 202 being attached to the needle end 302. A fingerflange 306 extends radially from the plunger end 304 of the barrel. Fluid is contained in an interior space 305 within the barrel.

As depicted here, the injection device includes an auto-retracting needle. To enable the auto-retraction, an inner sleeve 216 also extends from the base end of the housing 210. This inner sleeve 216 is located within the lower channel sidewall 270, or in other words is closer to the center of the injection device than the lower channel sidewall. The inner sleeve is shorter than the lower channel sidewall. A return spring 218 is located between the lower channel sidewall 270 and the inner sleeve 216. The return spring 218 is a compression spring, and is seen here in an extended state (not compressed). The needle end 302 also includes a forward surface 309 for interacting with the return spring. Here, the forward surface 309 is located on a collar 308 that extends away from the barrel 300 and towards the needle end 302.

An upper channel piece 310 is located above and surrounding the lower channel sidewall 270. The upper channel piece 310 is formed from a sidewall 312 and includes a top wall 314. The exterior surface 322 of the upper channel piece includes a groove 336 which interacts with the tongue 248 on the latching end 246 of the plunger handle 240. The lower end 316 of the upper channel piece also tapers downwards towards the lower channel 264 to allow the plunger handle 240 to be pulled upwards more easily. The interior side surface 318 of the upper channel piece 310 also includes a catch 330. The catch 330 includes a stop surface 332 located above a tapered surface 334 that tapers downwards. The catch 330 engages a trench 280 on the exterior surface 278 of the lower channel sidewall 270. This prevents the upper channel piece 310 from moving upwards away from the lower channel sidewall 270 when the plunger handle 240 is being pulled away from the housing (as seen in FIG. 6).

An injection head 340 extends from the interior top surface 320 of the upper channel piece 310. The injection head 340 has a U-shaped form with laterally flexible legs 342 that form a cavity 344 therebetween. The legs are biased to flex outwards. Extending outwardly from a central location on each leg 342 is a rudder 346 that contacts a guide surface 274 of the lower channel sidewall 270. This guide surface causes the legs to flex inwards and outwards as needed. The injection head is typically made from a resilient flexible material.

Between the injection head 340 and the fingerflange 306 of the barrel is a penetration drive 204. The penetration drive 204 includes a plunger sleeve 350. As seen here, the plunger sleeve 350 has a front surface 352 facing the fingerflange 306. The front surface 352 also includes a tube 351 through which a plunger shaft 370 will pass. The opposite side of the plunger sleeve 350 is generally open and will accept the injection head 340, as will be described later. The plunger sleeve 350 also includes a sidewall 354 that provides a rear surface 356 around the periphery of the plunger sleeve. At this initial state, the legs 342 of the injection head 340 are resting on the rear surface 356. The front surface 352 and the sidewall 354 of the plunger sleeve include shafts (not visible) through which the rudders 346 of the legs 342 of the injection head 340 will pass.

The penetration drive 204 rests upon a separation spring 360 that separates the front surface 352 of the penetration drive 204 from the fingerflange 306. The separation spring 360 is a compression spring which is in an extended state.

The separation spring 360 is located within the lower channel sidewall 270, and is depicted here as resting upon a flat surface 272 within the lower channel sidewall. The lower channel 264 includes the guide surface 274 which interacts with the rudders 346 on the legs of the injection head. This guide surface 274 is depicted here at the interior upper end 276 of the lower channel sidewall 270.

A plunger shaft 370 is also present. A piston 376 is attached to a first end of the plunger shaft and is located within the barrel 300. The piston 376 is slidably received within the barrel 300 and during operation is used to dispense the fluid within the barrel. The plunger shaft 370 extends through the tube 351 in the front surface 352 of the plunger sleeve 350. The second end of the plunger shaft is located within the plunger sleeve and includes a thumbrest 378. In operation, the injection head 340 will push against the thumbrest 378 to depress the piston 376.

As discussed above, the lower flange 230 may be used to seal against the skin and provide suction. Illustrated herein are two separate methods by which such suction might be performed. First, a string 380 is shown that extends through the base end 212 of the housing 210 and connects a surface (not visible) of the lower flange to the plunger handle 240. Here, the string is loose (not taut). As a separate second method, a tunnel 256 is located in the plunger handle 240 which passes completely through. Their use will be illustrated herein.

Figure 9:
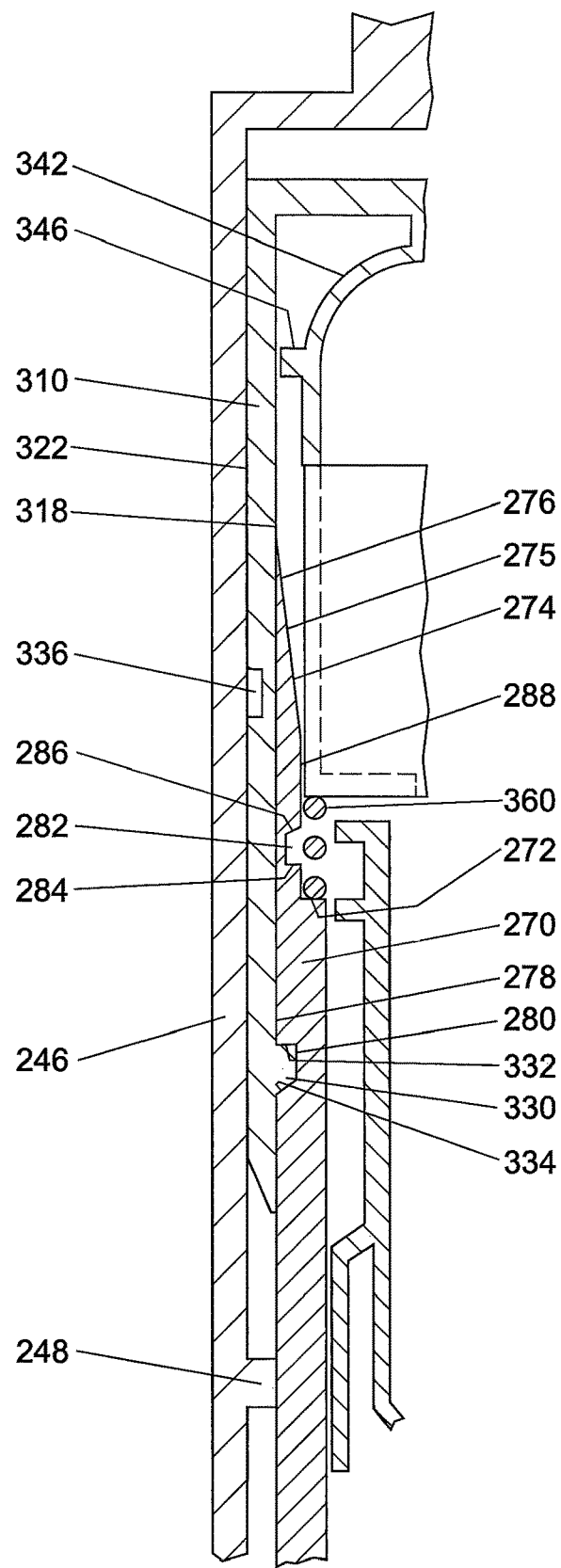
FIG. 9 is a magnified view of certain components in the initial state.

FIG. 9 is a magnified portion permitting some aspects of the injection mechanism to be better seen. In particular, the catch 330 on the interior side surface 318 of the upper channel piece 310, including the stop surface 332 and the tapered surface 334, and the trench 280 on the exterior surface 278 of the lower channel sidewall 270 are more visible. The guide surface 274 of the lower channel sidewall includes a tapering surface 275 which extends downward from the exterior surface 278 of the lower channel sidewall to the interior surface 288 of the lower channel sidewall. Located upon the interior surface 288 below the tapering surface 275 is a slit 282 into which the rudder 346 of the injection head will fit. The slit 282 includes a lower stop surface 284, and may also include a top tapered surface 286 which tapers upwards out of the lower channel sidewall.

Figure 10:
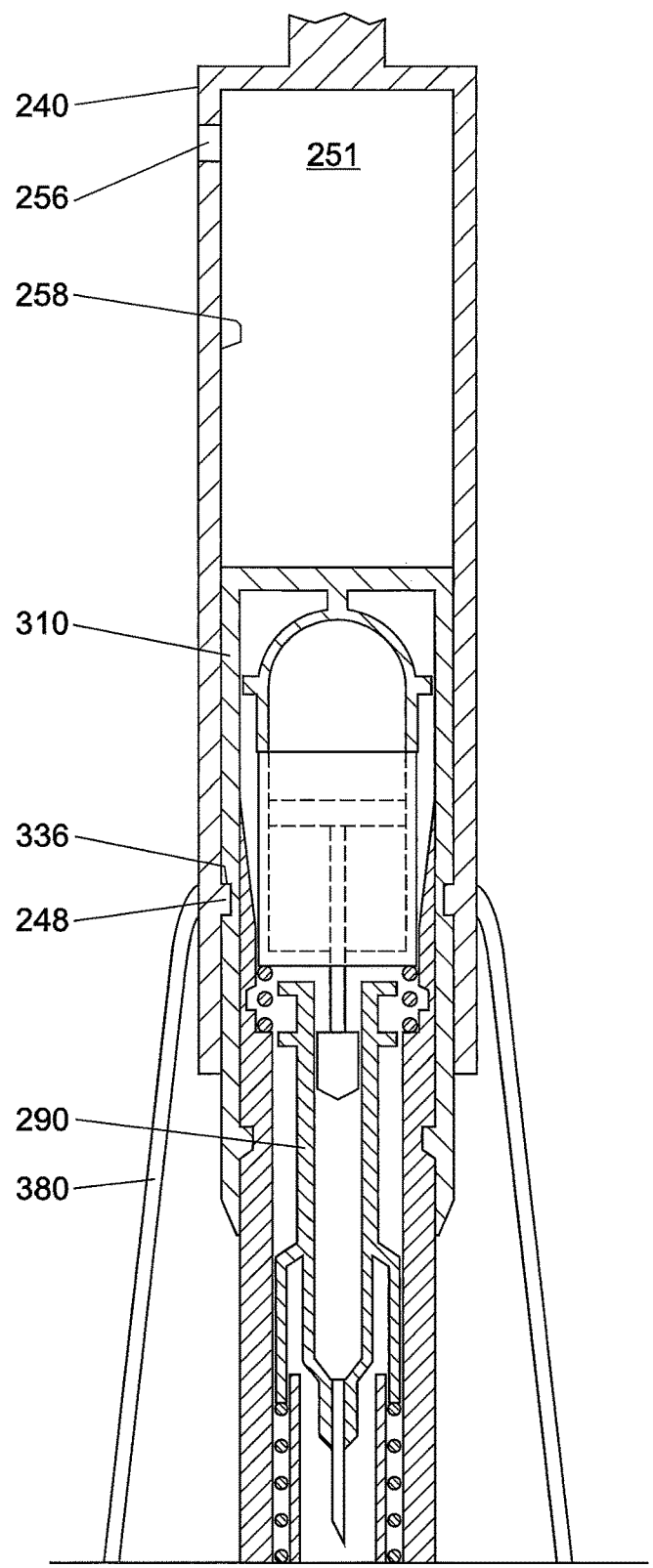
FIG. 10 is an interior cross-sectional view of the first exemplary embodiment of an injection device of the present disclosure, showing the internal components after the plunger handle has been pulled upwards (as in FIG. 6).

FIG. 10 now shows the injection mechanism after the plunger handle 240 has been pulled upwards, i.e. away from the housing 210. This corresponds to FIG. 6. The upper channel piece 310 is not pulled upwards along with the plunger handle 240 due to the insertion of the catch 330 into the trench 280 of the lower channel sidewall. The tongue 248 on the latching end of the plunger handle slides upward on the exterior surface 322 of the upper channel piece until the tongue 248 engages the groove 336 on the upper channel piece. Once the tongue 248 and groove 336 are engaged, the upper channel piece 310 and the plunger handle 240 will act as one component.

With regards to suction, the string 380 is pulled taut when the plunger handle 240 is extended. This causes the lower flange 230 to deform, creating suction between the lower flange and the skin of the user. Alternatively, pulling the plunger handle upwards creates an additional volume 251. The tunnel 256 in the plunger handle accesses this additional volume, reducing pressure within the housing 210 and again causing the lower flange 230 to deform and create suction. An O-ring (not shown) may be present on the interior surface 258 of the plunger handle to confirm that the additional volume 251 is airtight.

Figure 11:
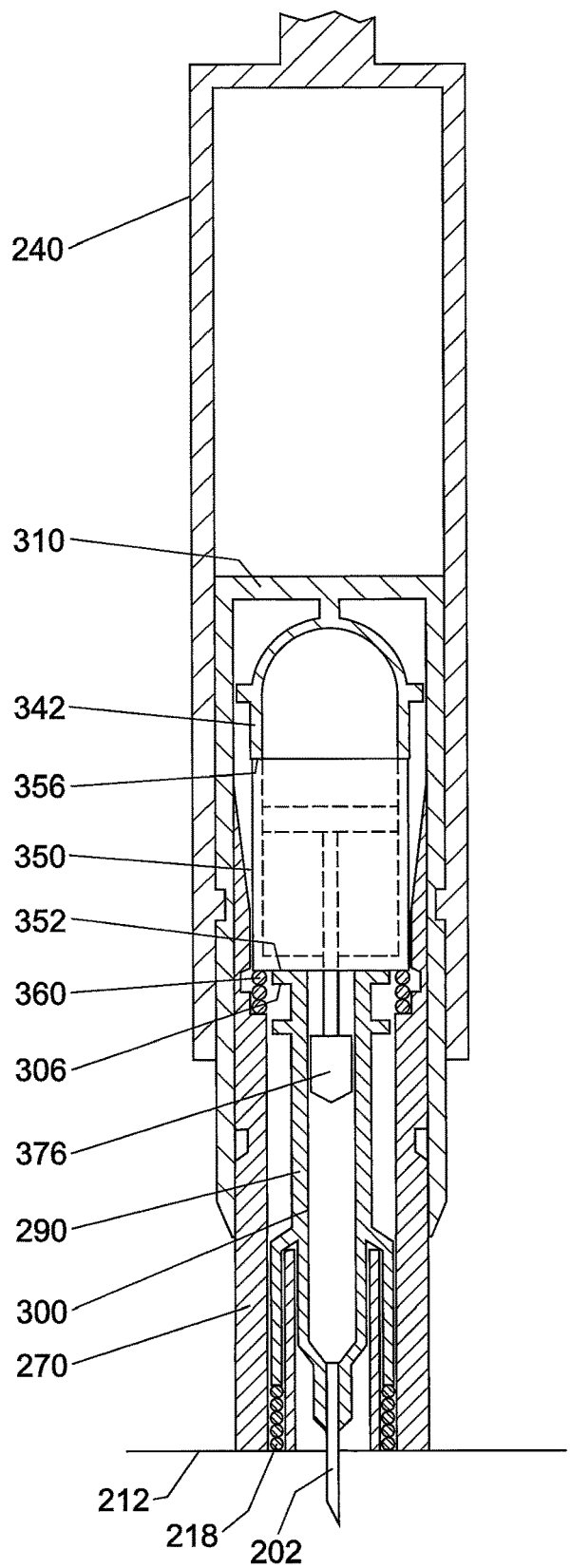
FIG. 11 is an interior cross-sectional view of the first exemplary embodiment of an injection device of the present disclosure, showing the internal components after the plunger handle is pushed down to a first level, showing the auto-insertion of the needle.

FIG. 11 now shows the injection mechanism as the plunger handle is being pushed downwards back into the housing 210, where the plunger handle 240 has reached a first level. Because the upper channel piece 310 and the plunger handle 240 are now joined together, the upper channel piece 310 is also moving downwards. The legs 342 of the injection head are pushing on the rear surface 356 of the plunger sleeve, causing the plunger sleeve 350 to travel downwards and compress the separation spring 360. This causes the front surface 352 of the plunger sleeve to contact the fingerflange 306 and push the barrel 300 downwards, causing the needle 202 to extend out of the housing 210 and into the user. The insertion depth of the needle can be predetermined and controlled. The return spring 218 is also compressed. Note that the piston 376 travels with the plunger sleeve 350 and the barrel 300, and has not yet been depressed. Also note that the catch 330 and the trench 280 are disengaged, so that the upper channel piece 310 can move down the lower channel sidewall 270 (see FIG. 9).

Figure 12:
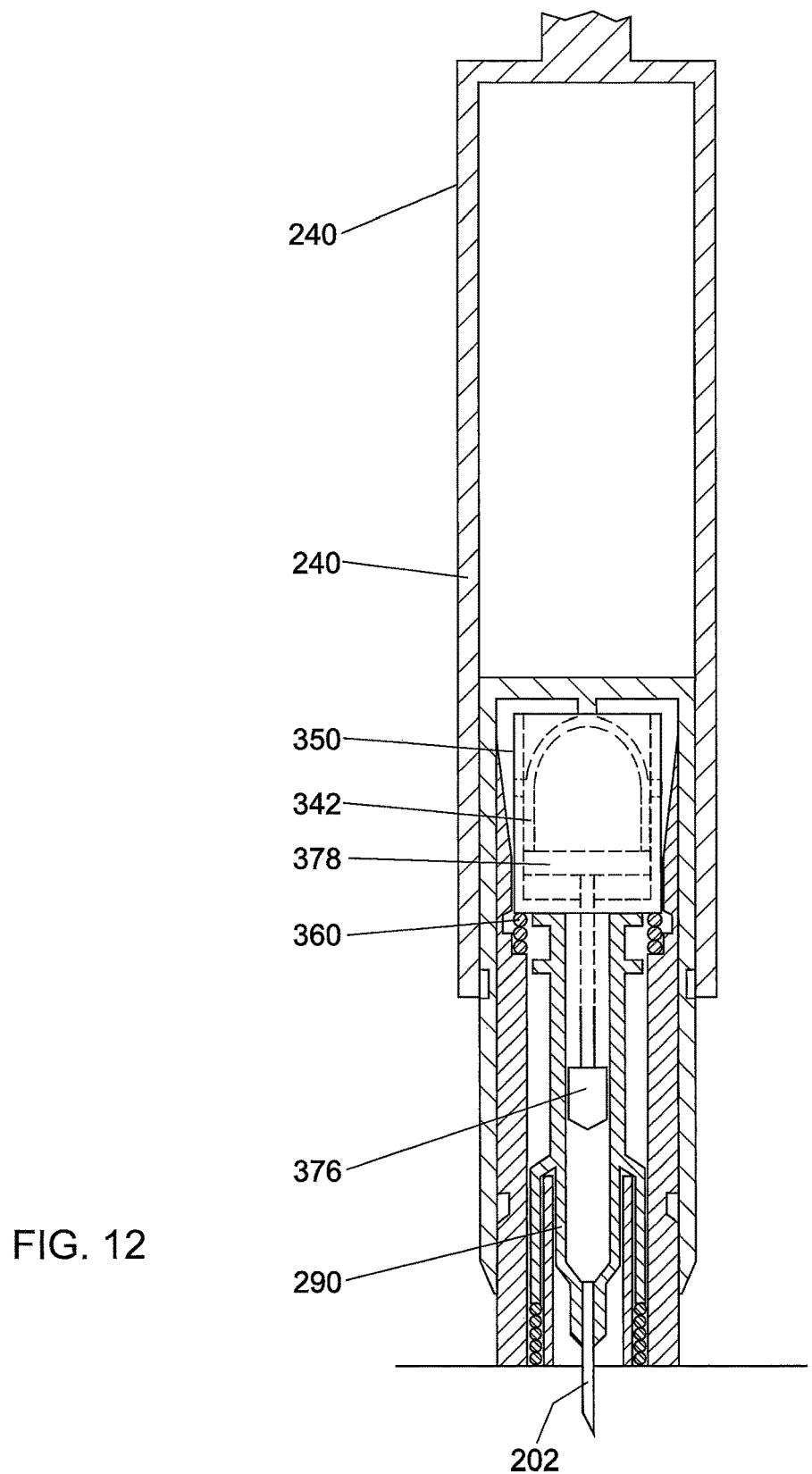
FIG. 12 is an interior cross-sectional view of the first exemplary embodiment of an injection device of the present disclosure, showing the internal components after the plunger handle is pushed down to a second level, showing the auto-injection of fluid through the needle.

FIG. 12 shows the injection mechanism as the plunger handle 240 is still being depressed and has now reached a second level. Once the plunger sleeve 350 has completely compressed the separation spring 360, the rudders 346 of the legs of the injection head contact the guide surface 274 of the lower channel sidewall. This causes the legs to flex inwards, falling off of the rear surface 356 of the plunger sleeve and into the interior of the plunger sleeve 350. As a result, the legs 342 now contact the thumbrest 378 on the plunger shaft and begin depressing the piston 376 to dispense fluid through the needle 202. Because there is no longer pressure being exerted on the plunger sleeve 350, the separation spring 360 may be decompressed/extended and push the plunger sleeve upwards. However, the thumbrest 378 will eventually contact the plunger sleeve and continue pushing the plunger sleeve downwards.

Figure 13:
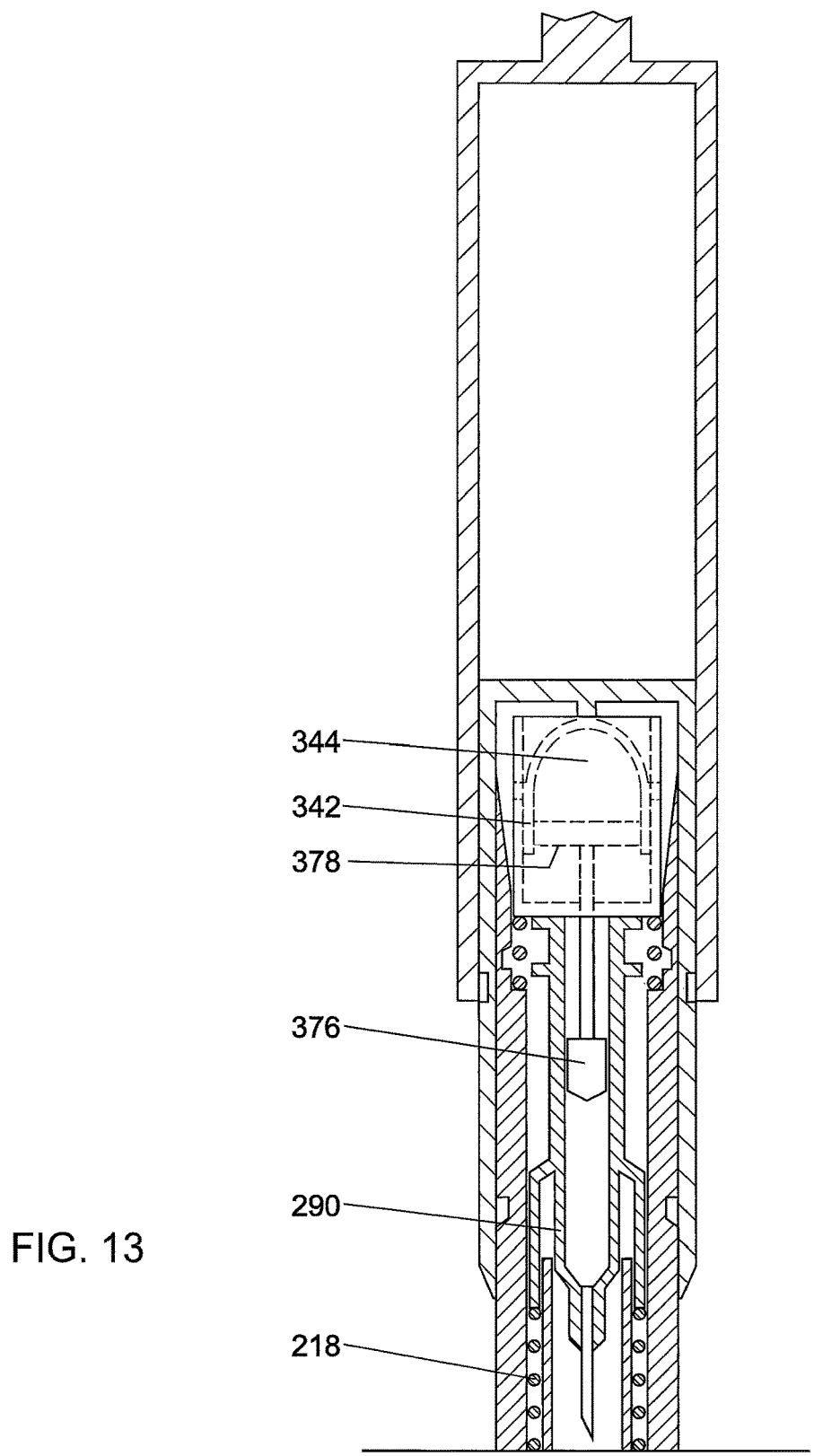
FIG. 13 is an interior cross-sectional view of the first exemplary embodiment of an injection device of the present disclosure, showing the internal components after injection is complete and showing the auto-retraction of the needle.

FIG. 13 shows the injection mechanism after injection is complete. Referring back to FIG. 9, the piston 376 will be depressed until the rudders 346 reach the slit 282. At this point, the legs 342 will flex back outwards and no longer contact the thumbrest 378. This reopens the cavity 344, which is sized to accommodate the thumbrest 378. The return spring 218 decompresses and pushes the injection assembly 290 upwards so that the thumbrest 378 is located within the cavity 344 between the legs of the injection head.

Some medications are unstable in a dissolved state, or are hygroscopic. These medications are usually separated into a liquid and a solid and mixed at the time of use. For example, a drug is lyophilized, then mixed with a liquid at the time of use. In another variation on this first exemplary embodiment of an injection device, the injection device is modified to include two compartments. The liquid can be stored in one compartment and a powder can be stored in the other compartment.

Figure 14:
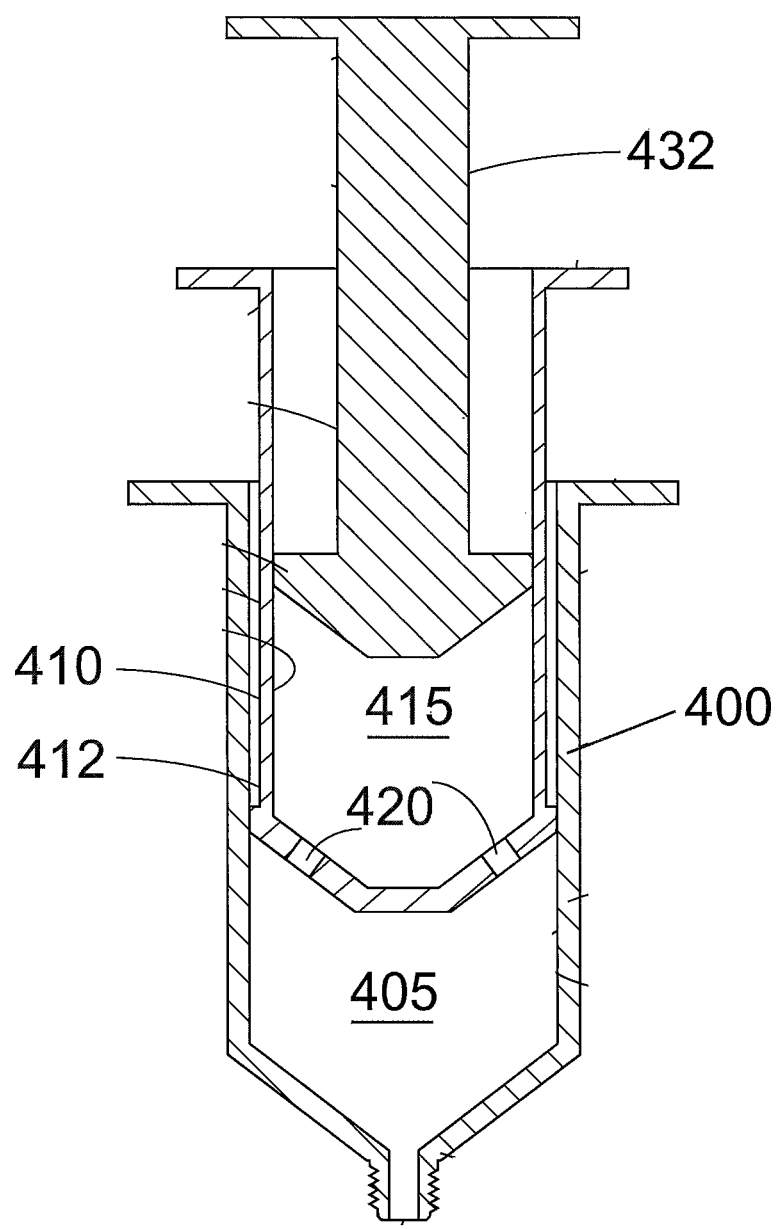
FIG. 14 is a diagram illustrating a variation on the first exemplary embodiment, wherein the injection device contains two compartments and how a liquid and powder can be mixed within the injection device.

Syringes having two compartments are known in the art. FIG. 14 provides a depiction of how the injection device described in FIGS. 8-13 could be suitably modified. In FIG. 14, the outer barrel 400 corresponds to the barrel 300 of FIG. 9. Disposed within the outer barrel 400 is an inner barrel 410 which can slide within the outer barrel 310. The bottom end 412 of this inner barrel would operate as the piston 376 of FIG. 9. The inner barrel 410 contains an interior space 415. The bottom end 412 notably contains one or more discrete channels 420 which permit fluid within the inner barrel 410 to be injected into the interior space 405 of the outer barrel 400 containing the powder, to reconstitute the drug and form the fluid. The inner barrel 410 then acts as a piston to eject the fluid through the needle 202. The injection head 340, penetration drive 204, and the lower channel sidewall 270 of FIG. 8 would be suitably modified to act on the second piston 432 in the inner barrel 410, then continue pushing the inner barrel 410 through the outer barrel 400 to eject fluid through the needle 202. In this regard, it is believed that the inner barrel 410 would not depress significantly while the plunger 430 is being depressed, because the dry powder alone should flow worse than the fluid. In addition, the relative friction between the plunger 430, the inner barrel 410, and the outer barrel 400 can be modified to control this factor.

A second exemplary embodiment of an injection device of the present disclosure is illustrated in FIGS. 15-22. As opposed to the traditional syringe in which the thumb is used to depress the plunger and dispense the fluid in the needle, this embodiment uses a squeezing motion of at least one lever to self-administer medication. A safety feature is present at the needle exit point of the device, in the form of a safety interlock that prevents the lever from being squeezed until the safety interlock is depressed. The injection function can then be engaged. The injection device also includes a color change visual indicator that provides a visual cur that the injection process is complete.

Figure 15:
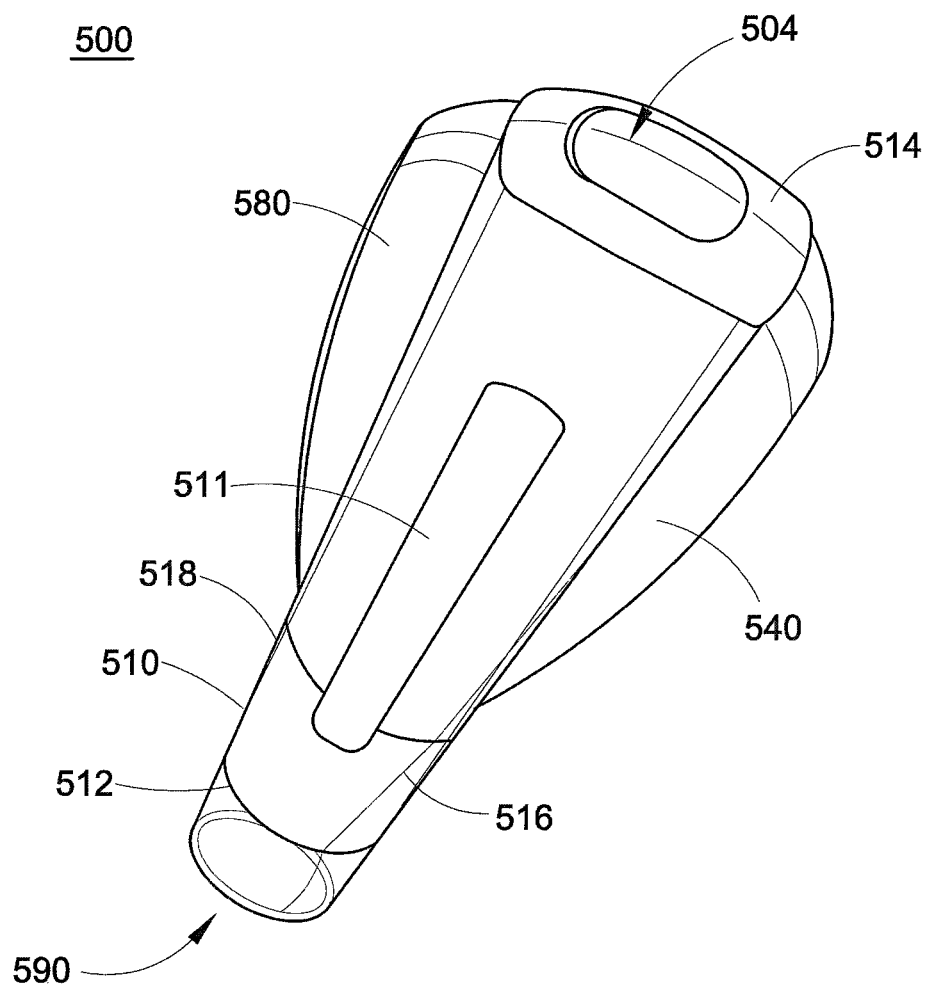
FIG. 15 is a perspective view showing a second exemplary embodiment of an injection device of the present disclosure.

FIG. 15 is a perspective exterior view of this second exemplary embodiment. The injection device 500 includes a housing 510 having a base end 512, a top end 514, and a side surface. The needle will protrude from the base end upon use. The top end 514 includes a visual indicator 504 for indicating whether the injection device has been used. At least one lever 540 extends from a side of the housing. As shown here, there are two levers 540, 580 that extend from opposite sides 516, 518 of the housing. A safety interlock 590 extends from the base end 512 of the housing and prevents the lever(s) from being pushed until the safety interlock is disengaged. Generally, the safety interlock is disengaged by pushing the safety interlock 590 towards the base end 512 of the housing for a sufficient distance. The safety interlock also acts as a safety ring for the needle.

Figure 16:
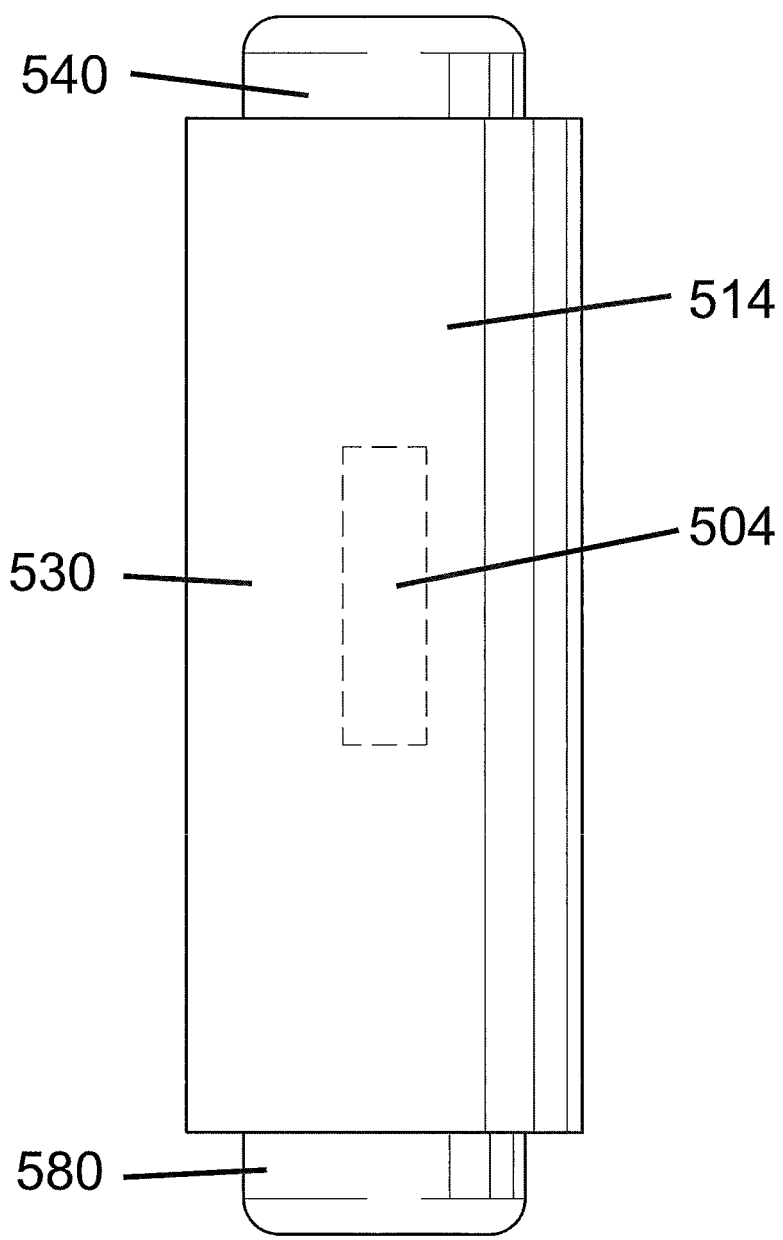
FIG. 16 is a top exterior view of the second exemplary embodiment of an injection device of the present disclosure.

FIG. 16 is a top exterior view of the injection device 500. From this top view, the injection device has a rectangular profile. The visual indicator 504 is placed in a central location 530. The two levers 540, 580 are visible on opposite sides.

Figure 17:
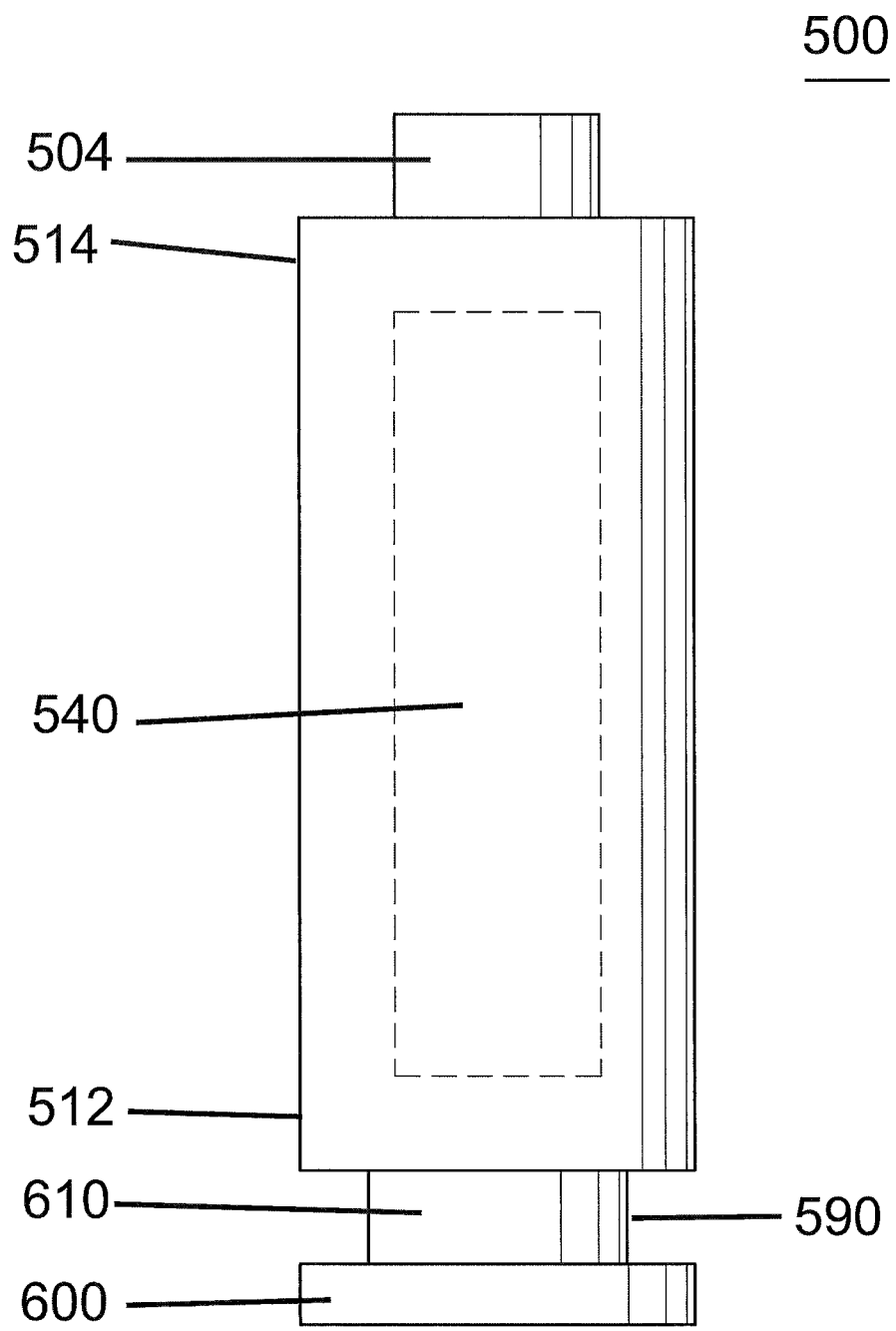
FIG. 17 is a side exterior view of the second exemplary embodiment of an injection device of the present disclosure.

FIG. 17 is a side exterior view of the injection device 500. The safety interlock 590 protrudes from the base end 512 of the housing. The safety interlock is depicted here as an annular ring 600 that parallels the base end of the housing. A blocking wall 610 extends transversely from the annular ring 600. The blocking wall is shown here as a discrete wall, with a second blocking wall 630 on the opposite side of the annular ring 600. However, in embodiments, the blocking wall could also be a continuous wall that completely encircles the annular ring.

Figure 18:
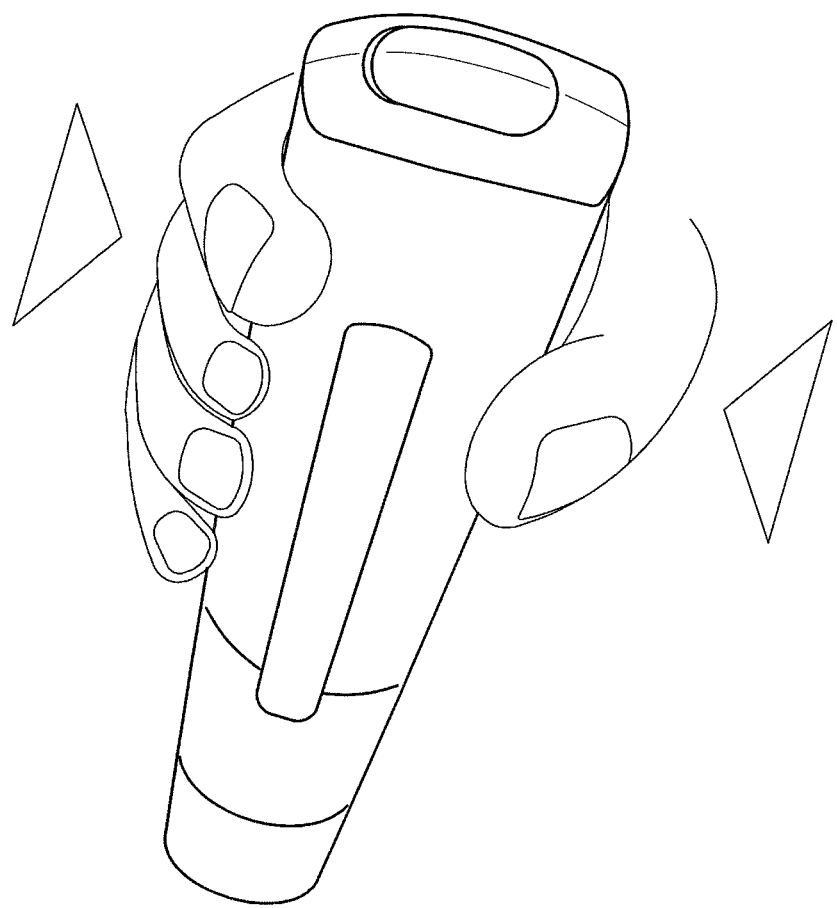
FIG. 18 is a perspective view showing the second exemplary embodiment of an injection device of the present disclosure being squeezed.

FIG. 18 illustrates the use of the injection device. The safety interlock is disengaged, and the lever(s) is squeezed towards the center of the housing.

Figure 19:
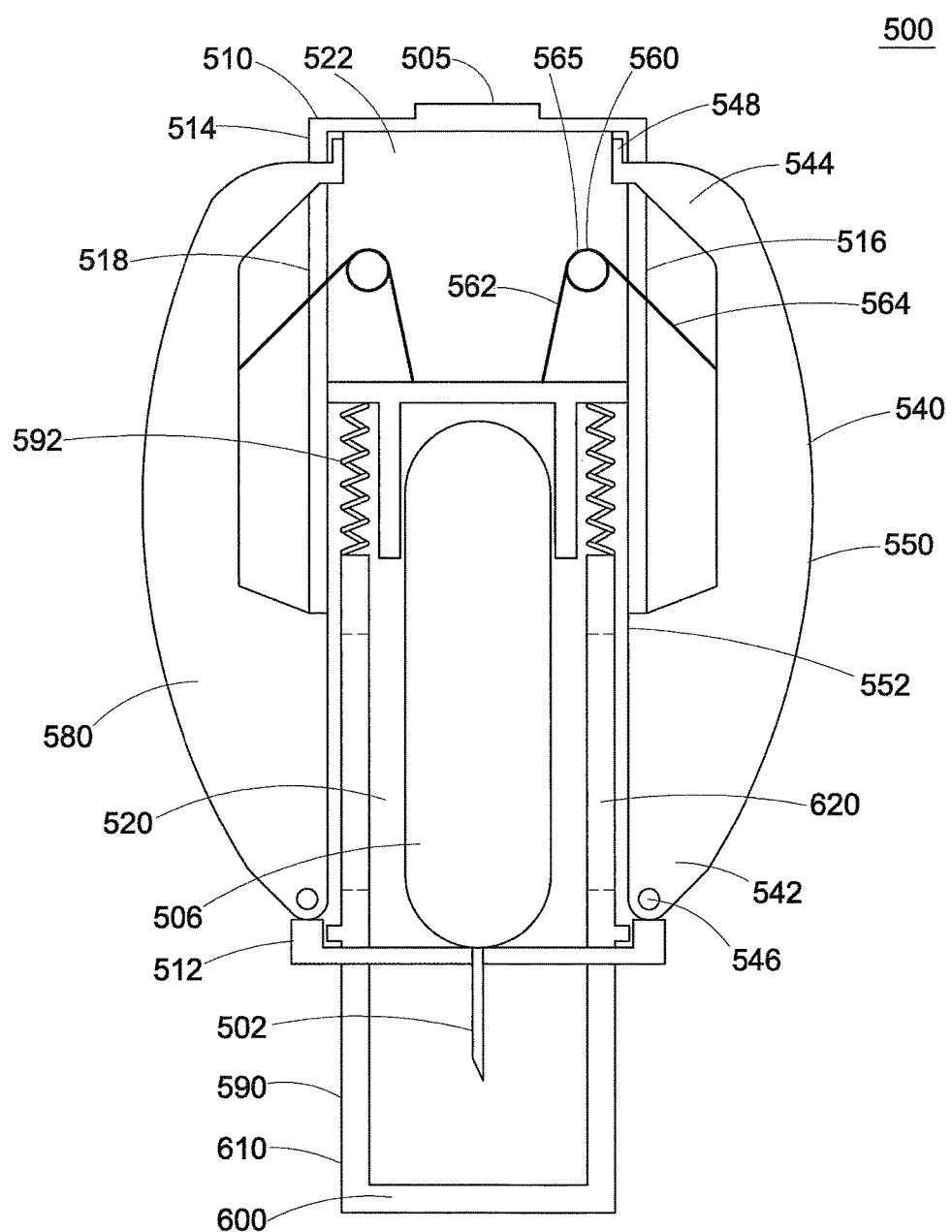
FIG. 19 is a front cross-sectional view of the second exemplary embodiment of an injection device of the present disclosure, illustrating a first possible construction in the initial unsqueezed state.

FIG. 19 is a front cross-sectional view of one possible construction for this second exemplary embodiment. It should be noted that while this description is given with respect to two levers, the description applies equally to a construction that uses only one lever. The housing 510 has a base end 512, a top end 514, a first side surface 516, and a second side surface 518. A needle 502 can protrude through an opening (not shown) in the base end 512 of the housing. The top end 514 includes a visual indicator to indicate whether the syringe has been used. The visual indicator is depicted here as an upper window 505 in the top end. A flexible ampoule 506 is located within a central cavity 520 in the housing, and contains the fluid that will be dispensed. The needle 502 is connected to the flexible ampoule 506. A first lever 540 extends from the first side surface 516, and a second lever 580 extends from the second side surface 518. When squeezed, the two levers 540, 580 will squeeze the ampoule 506 between them, causing fluid to be ejected from the ampoule through the needle. A safety interlock 590 is biased to extend from the base end 512 of the housing. The safety interlock prevents the levers from being pushed or squeezed together until the safety interlock is disengaged.

The housing 510 again may be transparent or contain a viewing window suitable for viewing the ampoule. A viewing window 511 can be seen in FIG. 15.

Each lever 540 includes an exterior grip surface 550, a pivot 546 at a first end 542, and a latch 548 at a second end 544. The pivot 546 and the latch 548 interact with the housing 510 to fix the lever in place. A clothespin spring 560 is used to bias each lever away from the housing. A clothespin spring is a torsion spring that includes two legs 562, 564 and a central coil 565, with the legs being separated at rest and the spring storing energy when the legs are squeezed together.

Figure 20:
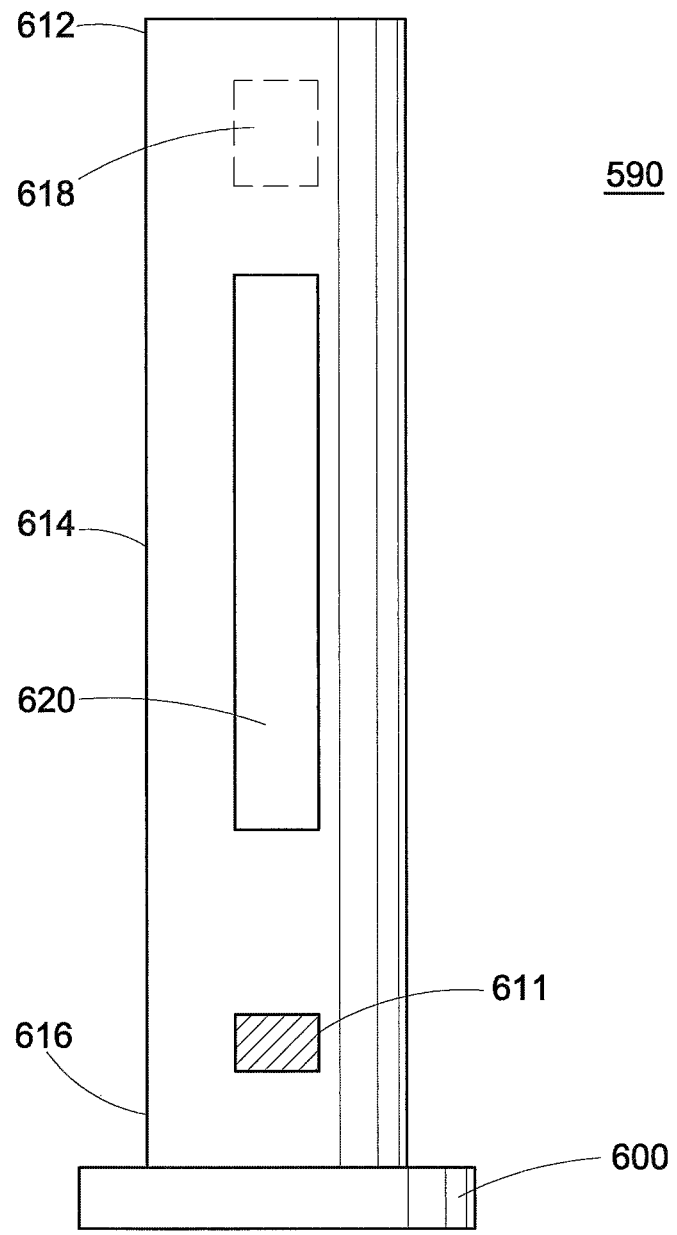
FIG. 20 is a side view of the safety interlock.

The safety interlock 590, in embodiments, includes an annular ring 600 and a blocking wall 610 extending transversely from the annular ring. A side view of the safety interlock is provided in FIG. 20. The annular ring 600 is located at a lower portion 616 of the blocking wall. A stop face 618 is located at an upper portion 612 of the blocking wall, and a channel 620 is located at a middle portion 614 of the blocking wall. A catch 611 extends from the blocking wall. Note that the channel is essentially a hole that extends through the blocking wall, while the catch is a structure extending from the blocking wall. Referring back to FIG. 19, safety springs 592 are used to bias the safety interlock 590 away from the housing. The safety springs are compression springs, and are in their extended state when the safety interlock is engaged. As depicted here, the catch 611 engages the housing 510 to control the distance that the safety interlock extends away from the base end of the housing. As depicted in FIG. 20, the catch 611 is located between the annular ring 600 and the channel 620. However, the catch 611 could also be located at the upper portion 612 of the blocking wall, engaging a suitable stop surface in the housing.

The safety interlock 590 interacts with the lever 540 to prevent or permit squeezing of the ampoule. In this regard, the lever 540 is shaped to provide a key 552. When the safety interlock is engaged, the stop face 618 engages the key 552. When the safety interlock is disengaged, the blocking wall (and the stop face) moves upwards into the housing until the channel 620 is aligned with the key 552. The key 552 then passes through the channel 620 to squeeze the ampoule 506. As depicted here, the key 552 is located near the first end 542 of the lever, with the pivot 546 being located near the base end 512 of the housing. However, it is also possible for the pivot 546 to be located near the top end 514 of the housing, and the key 552 to be located near the second end 544 of the lever by the latch 548.

Different variations on the safety interlock are possible, depending on the overall construction of the injection device. For example, when two levers are used, the safety interlock comprises an annular ring and two channels. Each lever has a key that passes through one of the channels. If the blocking wall is a continuous wall, the two channels are present on opposite sides of the continuous wall. If two discrete blocking walls are used, then one channel is located in a first blocking wall extending transversely from the annular ring, the other channel is located in a second blocking wall extending transversely from the annular ring, and the first and second blocking walls extend from opposite sides of the annular ring.

During operation, the safety interlock 590 is disengaged by pushing the safety interlock against the skin of the user at an injection site. As the safety interlock 590 enters the housing 510, the needle 502 passes through the center of the annular ring and into the skin. The levers 540, 580 can then be squeezed together to inject the fluid from the ampoule.

The housing 510 includes a top cavity 522 which can be used with the visual indicator/window to indicate that the injection is complete. Generally, any type of color change could be used. In embodiments, a chemical color change occurs. For example, the movement of the lever could be used to release a chemical compound or to cause a reaction between two chemical compounds. It is also possible for the movement of the lever to generate an electrical current that causes a visual change.

Figure 21:
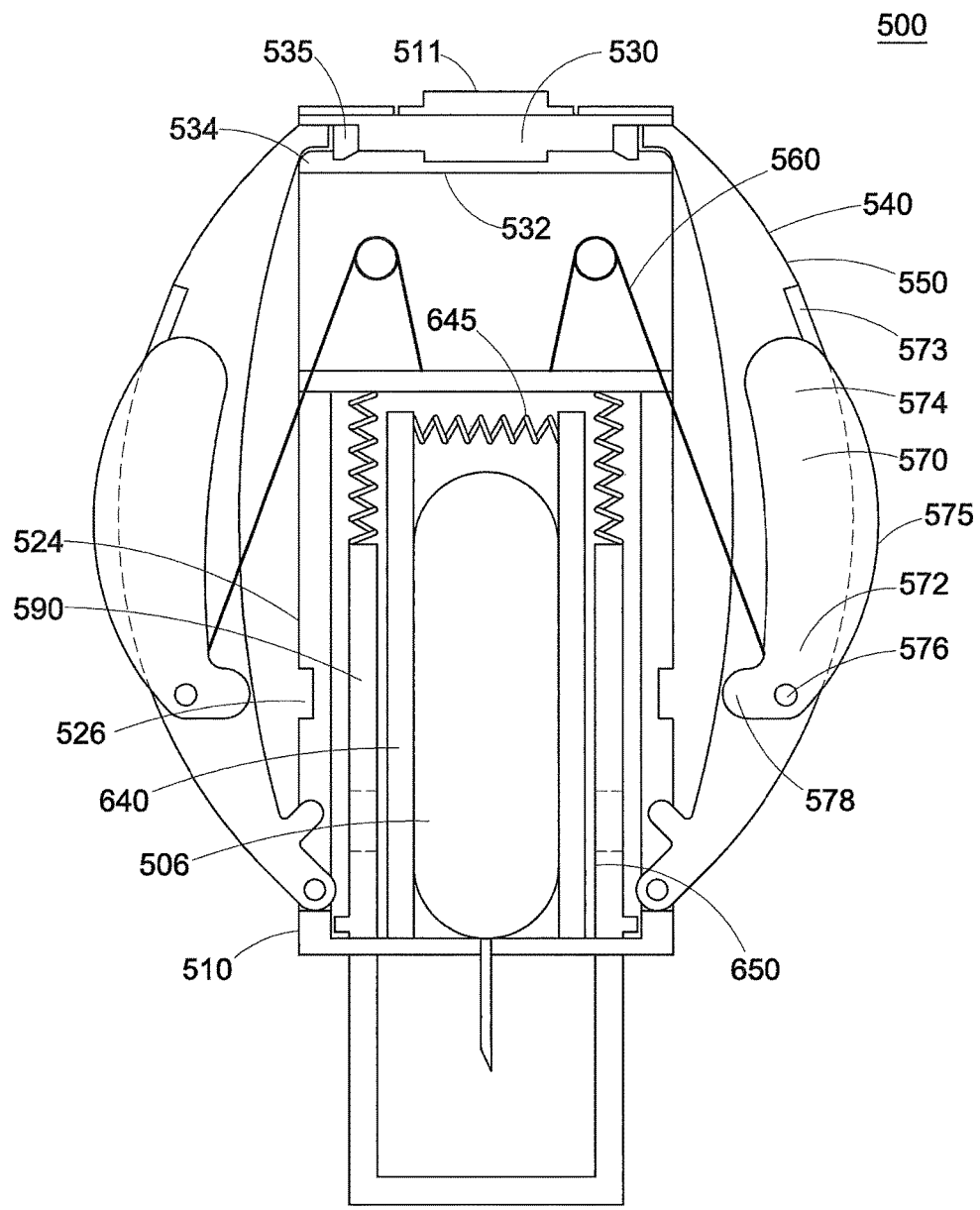
FIG. 21 is a front cross-sectional view of the second exemplary embodiment of an injection device of the present disclosure, illustrating a second possible construction in the initial unsqueezed state.

FIG. 21 is another front cross-sectional view of a second possible construction for this second exemplary embodiment. Here, each lever 540 further includes a safety trigger 570 to prevent lateral motion of the lever 540 after the safety interlock is disengaged. This adds a second layer of safety so that premature squeezing of the levers, even after the needle has been inserted, does not occur. Here, a slot (not visible) is present in the exterior grip surface 550 of the lever. The safety trigger 570 includes an outer surface 575 that extends through the slot. A pivot 576 is present at a first end 572 of the safety trigger, as well as a catch arm 578 that extends towards the housing from the first end 572, so that the safety trigger is roughly L-shaped. A stop arm 573 is present on a second end 574 of the safety trigger to engage the lever 540 and prevent the safety trigger from passing completely through the slot 551. The clothespin spring 560 engages the safety trigger 570, so that both the lever 540 and the safety trigger 570 are biased away from the housing 510. The housing 510 itself includes a stop surface 524 that engages the catch arm 578, and a safety cavity 526 adjacent the stop surface. As seen here, the catch arm 578 engages the stop surface 524 if the outer surface 575 is not squeezed, preventing any lateral motion if only the exterior grip surface 550 of the lever is squeezed. In another variation, located between the safety interlock 590 and the flexible ampoule 506 is a compaction wall 640. The compaction wall is adjacent the ampoule. Two compaction walls 640, 650 are visible here, and they are biased away from the ampoule by a compression spring 645 which is shown here in an extended state.

Figure 22:
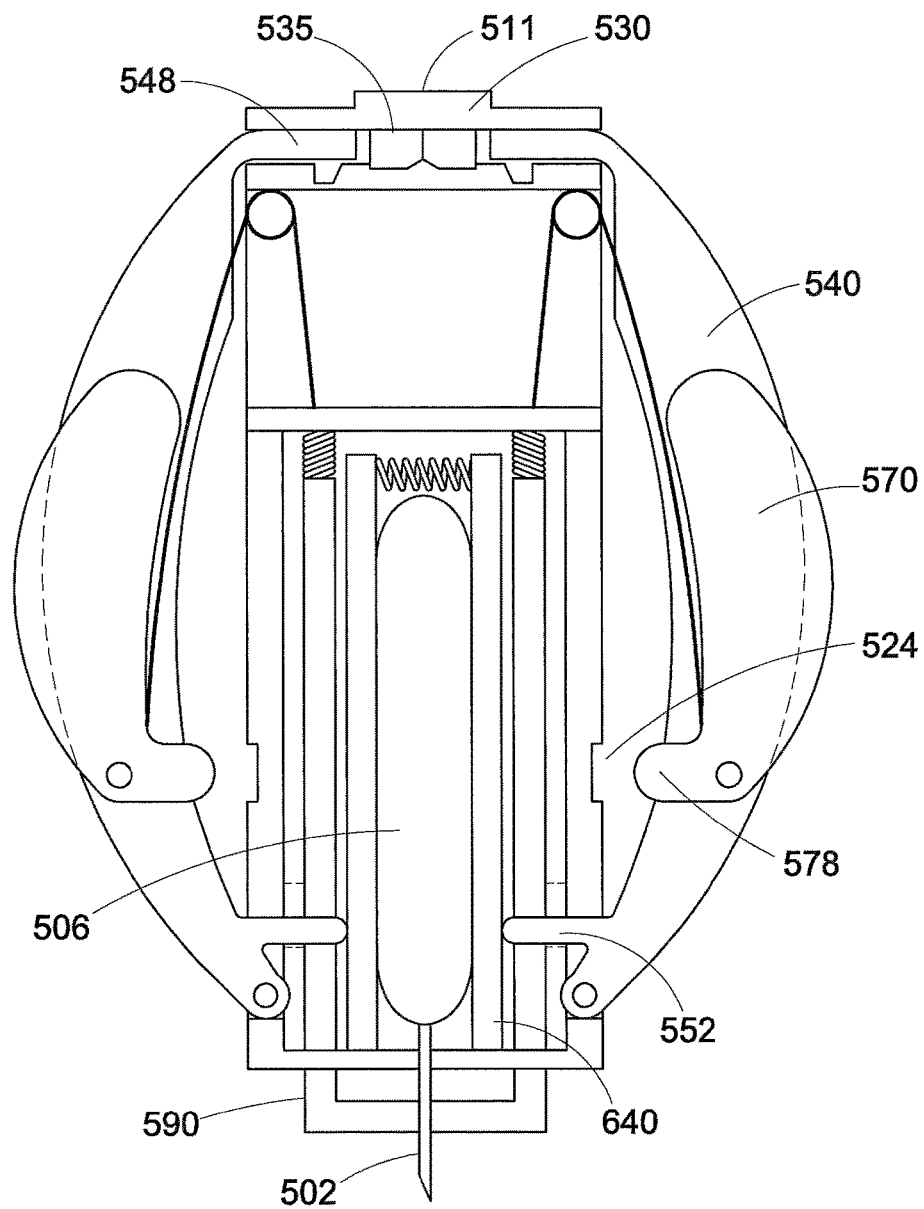
FIG. 22 is a front cross-sectional view of the second exemplary embodiment of an injection device of the present disclosure, illustrating the second possible construction in the squeezed state.

FIG. 22 shows another front cross-sectional view of the second possible construction for this second exemplary embodiment, after the levers are squeezed. After the safety interlock 590 is disengaged, the safety triggers 570 are squeezed, causing the catch arm 578 to pivot and travel beyond the stop surface 524 into the safety cavity 526. This allows the levers 540 to be fully squeezed, causing the key 552 to pass through the channel 620 in the blocking wall 610 and contact the compaction wall 640, causing the ampoule 506 to be squeezed and fluid to be ejected from the needle 502.

Referring back to FIG. 21, also depicted at the top end 514 of the housing is a mechanism for visually indicating whether the syringe has been used. A central location 530 is visible through the window 511. A ledge 532 is located in the central location, and has a first color. Located at a non-visible location 534 to the side of the central location is a color segment 535 having a second different color.

Referring now to FIG. 22, when the levers are squeezed, the latch 548 on the lever travels, moving the color segment 535 from the non-visible location 534 to the visible central location 530. In effect, the color segment 535 hides the first color and displays the second color through the window 511.

The injection device 500 is subsequently removed by releasing the levers 540, allowing the safety springs 592 to push the safety interlock 590 away from the housing and cover the needle 502 as the needle is pulled out of the skin.

Figure 23:
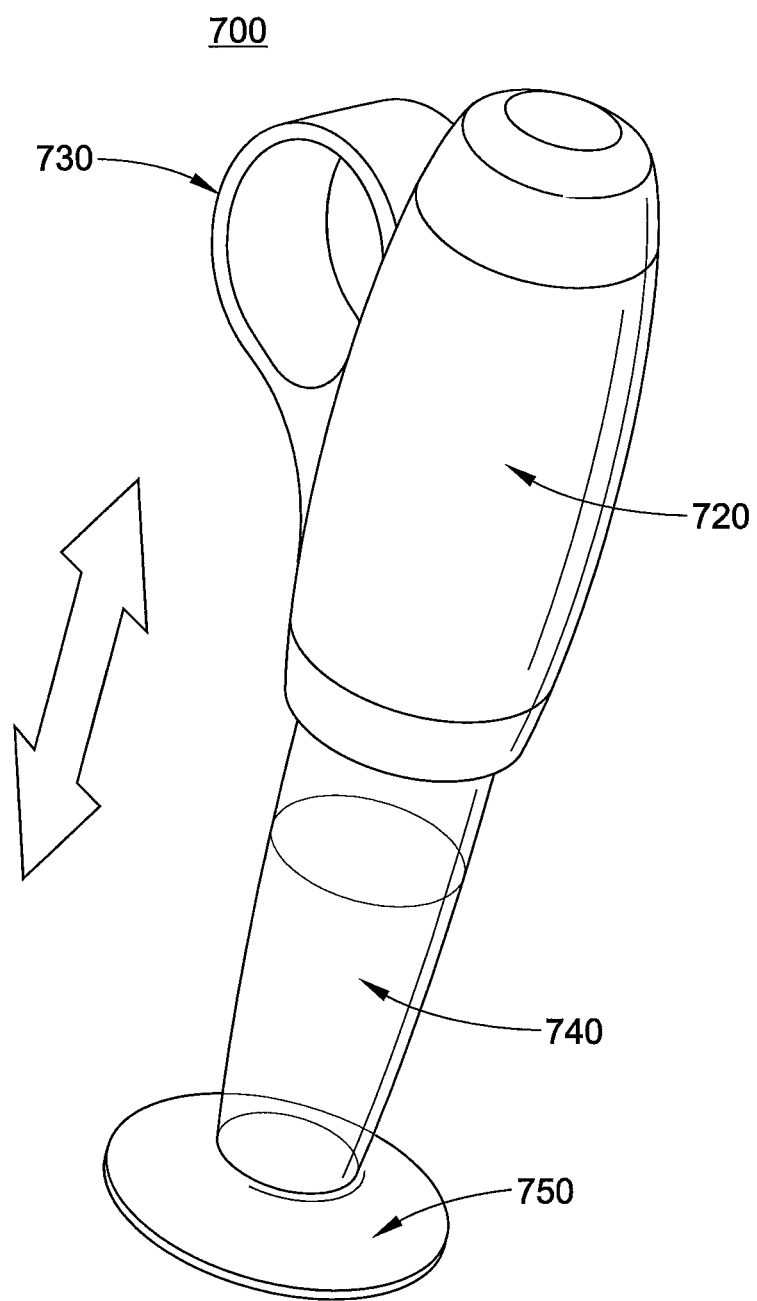
FIG. 23 is a perspective view of a first variation on a third exemplary embodiment of an injection device of the present disclosure.
Figure 24:
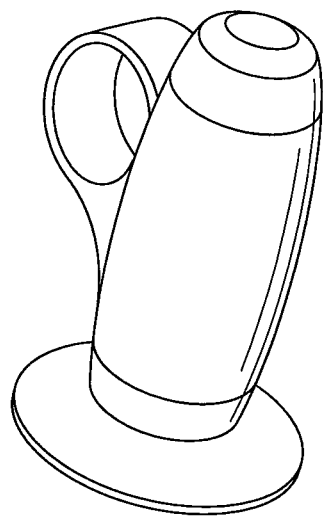
FIG. 24 is a perspective view of the first variation of FIG. 23 in a compressed or depressed state.
Figure 25:
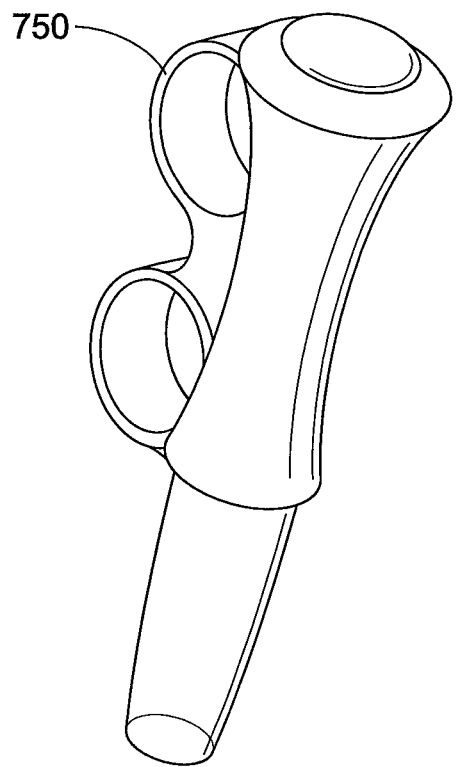
FIG. 25 is a perspective view of a second variation on a third exemplary embodiment of an injection device of the present disclosure.

FIGS. 23-26 illustrate a third exemplary embodiment of an injection device of the present disclosure. Each figure shows a perspective view of some variations on the third exemplary embodiment. Here, the injection device provides grip aids that are integral to the housing to enhance handling of the device during operation. Generally, the injection device 700 includes a housing 740 and a plunger having a plunger shell 720. The plunger shell surrounds the housing, and telescopes over the housing as the device is compressed to dispense fluid. In FIG. 23, the injection device includes an external grip 730 protruding from the side of the plunger shell, which forms one ring. A lower flange 750 also extends radially from the base end of the housing. This acts as a holding surface for a second hand to stabilize the injection device. Again, it should be noted that the lower flange extends around the entire base end. FIG. 24 shows the device of FIG. 23 in the compressed state. In FIG. 25, the external grip 750 on the plunger shell includes two rings, and no lower flange is present. In embodiments, the grip may have an outer diameter of about 1 and ⅝ inches, and the inner diameter of the grip may be about ⅞ inches.

These injection devices are generally contemplated to be auto-injectors, and such mechanisms are known in the art. This embodiment can be a single-use prefilled injection device. A needle, a barrel, and a plunger are located within the device. The needle may be an auto-inserting needle and/or an auto-retracting needle. A penetration drive may be included to insert the needle and dispense fluid through the needle. A visual indicator may be included on the housing to indicate whether the device has been used. Again, the visual indicator can be a chemical color change. In some embodiments, the housing is transparent. A mechanism within the device may also assist the user by reducing the amount of force needed to compress the device during injection.

Figure 26:
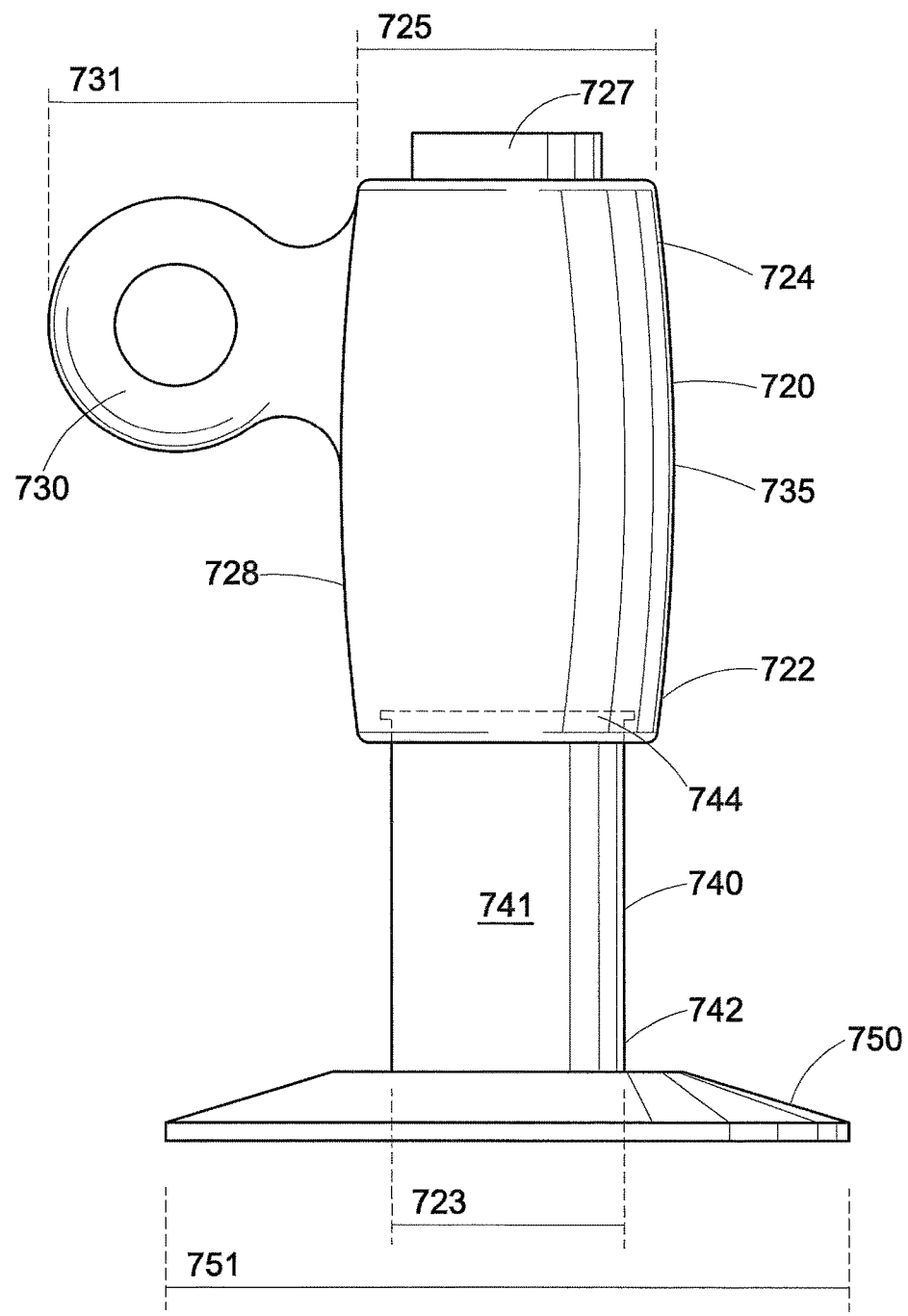
FIG. 26 is an exterior side view of the first variation of FIG. 23.

FIG. 26 is a side view of the variation shown in FIG. 23. The device is formed from a plunger shell 720 and a housing 740. The plunger shell 720 has a bottom end 722 and a top end 724 located on opposite sides. The housing 740 has a base end 742 and an upper end 744 located on opposite sides. The upper end 744 is slidably received within the bottom end 722 of the plunger shell. The housing is transparent (reference numeral 741). The housing has a shorter height than the plunger shell. A lower flange 750 extends radially from the base end 742 of the housing. An external grip 730 protrudes from a side 728 of the plunger shell. The side 728 is an exterior surface of the injection device. The visual indicator is shown as a window 727 on the top end 724 of the plunger shell.

Similar to the embodiment of FIG. 2, the lower flange 750 extends radially from the base end 742 of the housing, and serves as a hand rest. Again, the lower flange can be a full disk shape and be located below the base end of the housing, or alternatively have an annular shape and be located around the housing at the base end. In embodiments, the width 751 of the lower flange is at least twice the width 723 of the bottom end 722 of the plunger shell 720 (which is wider than the). If the plunger shell 720 and the lower flange 750 are cylindrical, the width would correspond to the diameter.

The external grip 730 on the plunger shell is oversized for ease of use. In embodiments, the width 731 of the external grip is equal to or greater than the width 725 of the top end 724 of the plunger shell 720. This width is measured as the outer width of the grip, not the inner width. In particular embodiments, the width 731 of the external grip is at least 1.5 inches. When the grip is circular, the width corresponds to the diameter.

A stop may be present within the housing to prevent the bottom end 722 of the plunger shell from contacting the lower flange 750. This leaves room between the external grip and the lower flange for the second hand which is stabilizing the injection device.

In FIG. 26, the plunger shell 720 tapers outwards between the bottom end 722 and the top end 724 (reference numeral 735). However, this direction of taper is not significant, and the taper may be inwards between the bottom end and the top end if desired.

Figure 27:
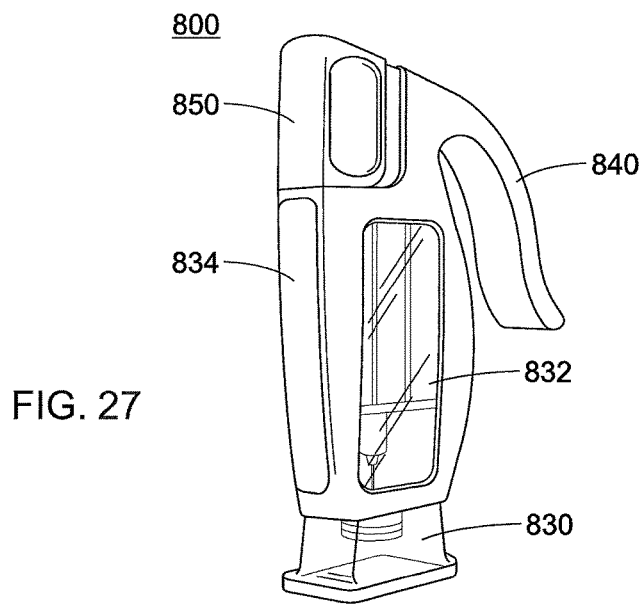
FIG. 27 is a perspective view of a fourth exemplary embodiment of an injection device of the present disclosure.
Figure 28:
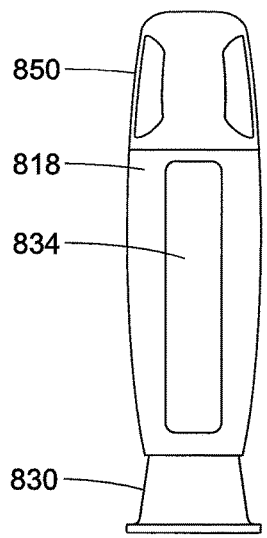
FIG. 28 is a front view of the fourth exemplary embodiment of an injection device of the present disclosure.
Figure 29:
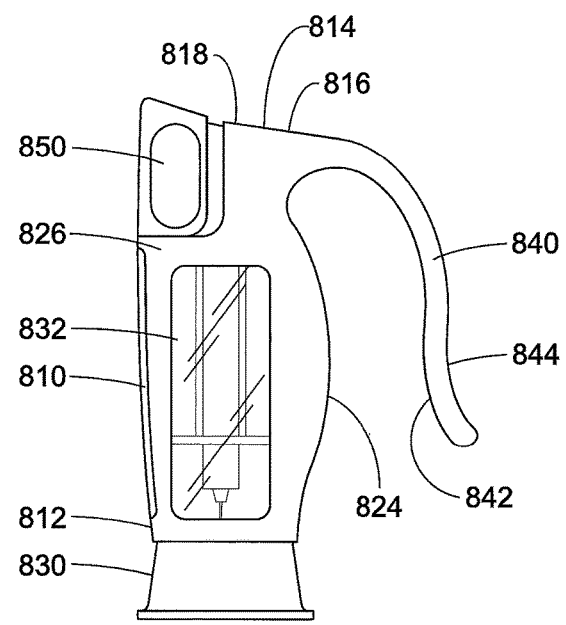
FIG. 29 is a side view of the fourth exemplary embodiment of an injection device of the present disclosure.

FIGS. 27-31 illustrate a fourth exemplary embodiment of an injection device. FIG. 27 is a perspective view. FIG. 28 is a front view. FIG. 29 is a side view. It is contemplated that this embodiment is an autoinjector. This embodiment can be a single-use prefilled injection device. A needle, a barrel, and a plunger are located within the housing. The needle may be an auto-inserting needle and/or an auto-retracting needle. A penetration drive may be included to insert the needle and dispense fluid through the needle.

The injection device 800 includes a housing 810 having a base end 812 and a top end 814. The needle (not shown) extends from the base end 812 of the housing. A transparent needle shield 830 may also be present below the base end 812. A hook 840 extends from a rear end 816 of the top end 814 of the housing 810, away and towards the base end. An actuation button 850 is located on a front end 818 of the top end 814 of the housing, the front end being opposite the rear end. The actuation button 850 is thus opposite the hook 840 on the top end 814 of the housing. The actuation button 850 moves towards the rear end 816 upon being pushed. As seen in FIG. 29, the hook 840 includes an inward surface 842 and an outward surface 844. The rear surface 824 of the housing may be complementary to the inward surface 842 of the hook. In addition, at least one of the side surfaces 826 includes a transparent window 832 for the user to view the internal mechanism and medication. A pad 834 may be present on the front surface 822 of the housing for comfort, if desired.

Figure 30:
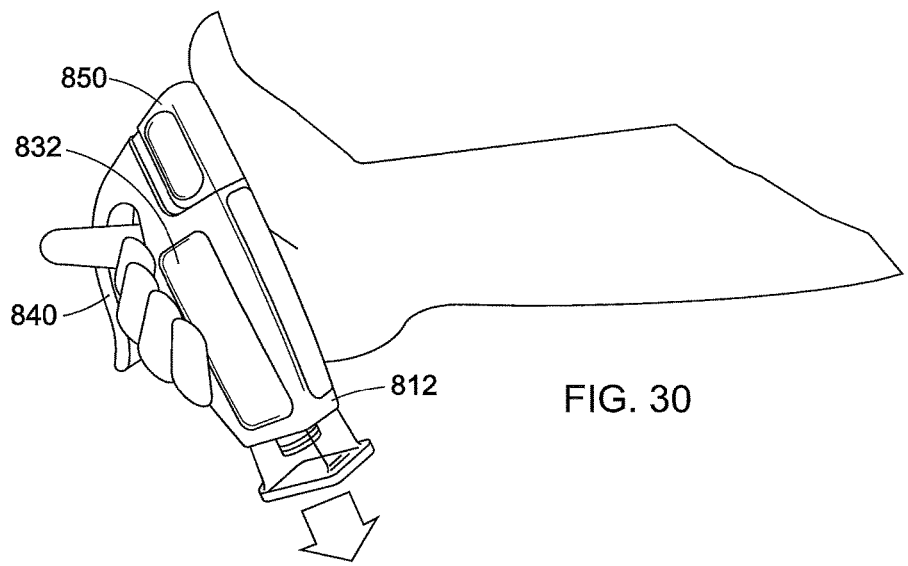
FIG. 30 is a diagram illustrating how to hold the fourth exemplary embodiment.
Figure 31:
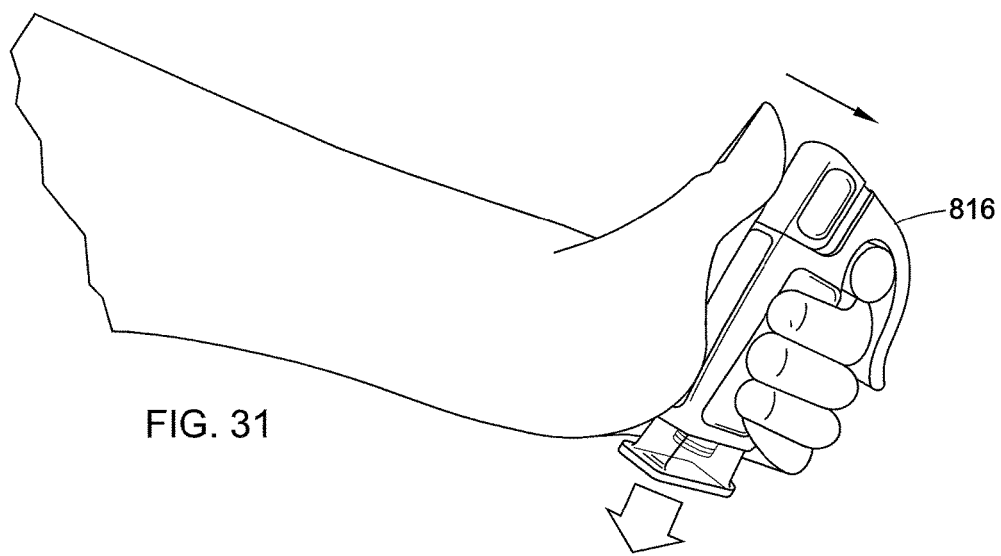
FIG. 31 is a diagram illustrating the activation of the fourth exemplary embodiment.

The actuation button 850 in some embodiments has a width (from front end 818 to rear end 816) of about 1 inch, a length (from top end 814 to base end 812) of about 1.5 inches, and a depth (from side to side) of 0.75 inches. The transparent window 832 may have a width (from front end 818 to rear end 816) of about 0.5 inches and a length (from top end 814 to base end 812) of about 2 inches in some embodiments FIG. 30 and FIG. 31 illustrate the usage of the fourth exemplary embodiment of an injection device. As seen in FIG. 30, the device is grasped with the housing in the palm, the rear end against the fingers so that the hook 840 extends over the hand, with the fingers between the housing 810 and the hook, and the base end 812 pointed towards the user. The actuation button 850 is adjacent the thumb. As shown in FIG. 31, the actuation button 850 moves towards the rear end 816 when the button is depressed, following the natural motion of the thumb. An internal mechanism then inserts the needle and dispenses medication.

Figure 32:
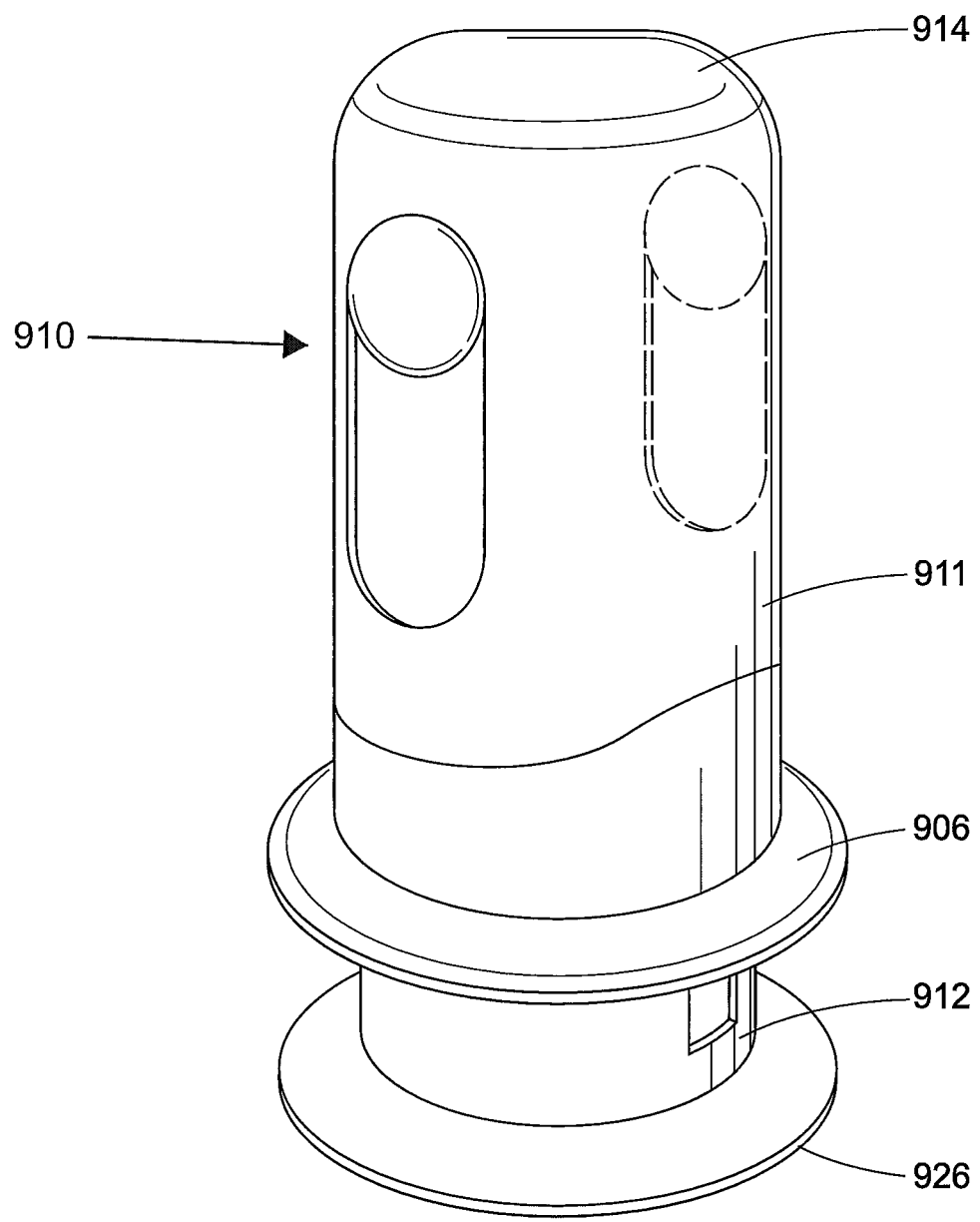
FIG. 32 is a perspective view of a fifth exemplary embodiment of an injection device of the present disclosure.
Figure 34:
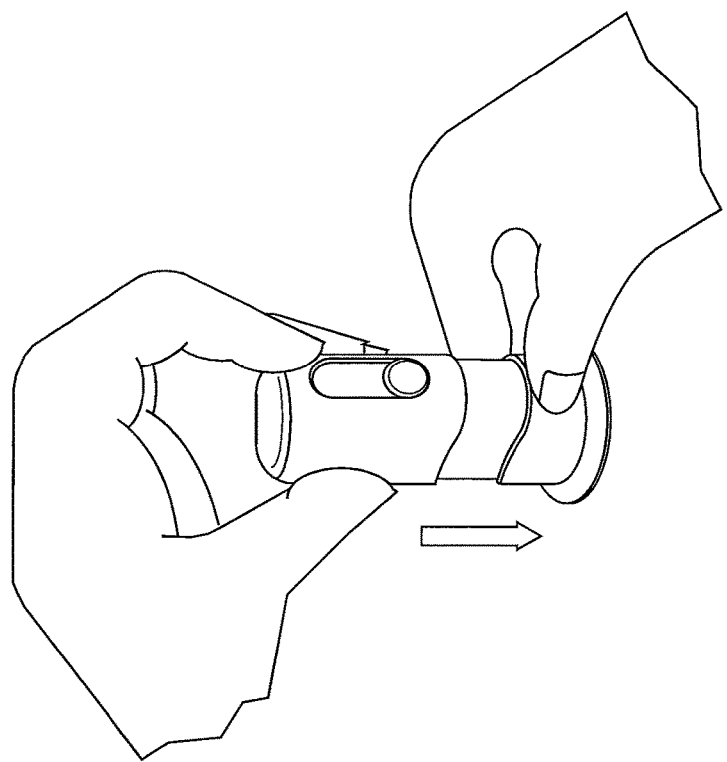
FIG. 34 is a diagram illustrating how the fifth exemplary embodiment is activated.
Figure 33:
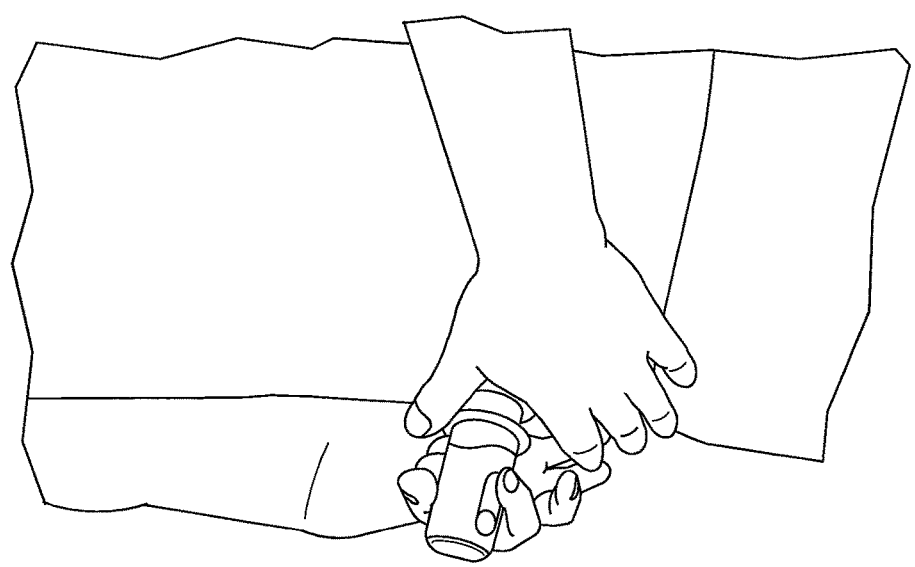
FIG. 33 is a diagram showing the fifth exemplary embodiment of an injection device of the present disclosure being placed against the skin of a user.
Figure 35:
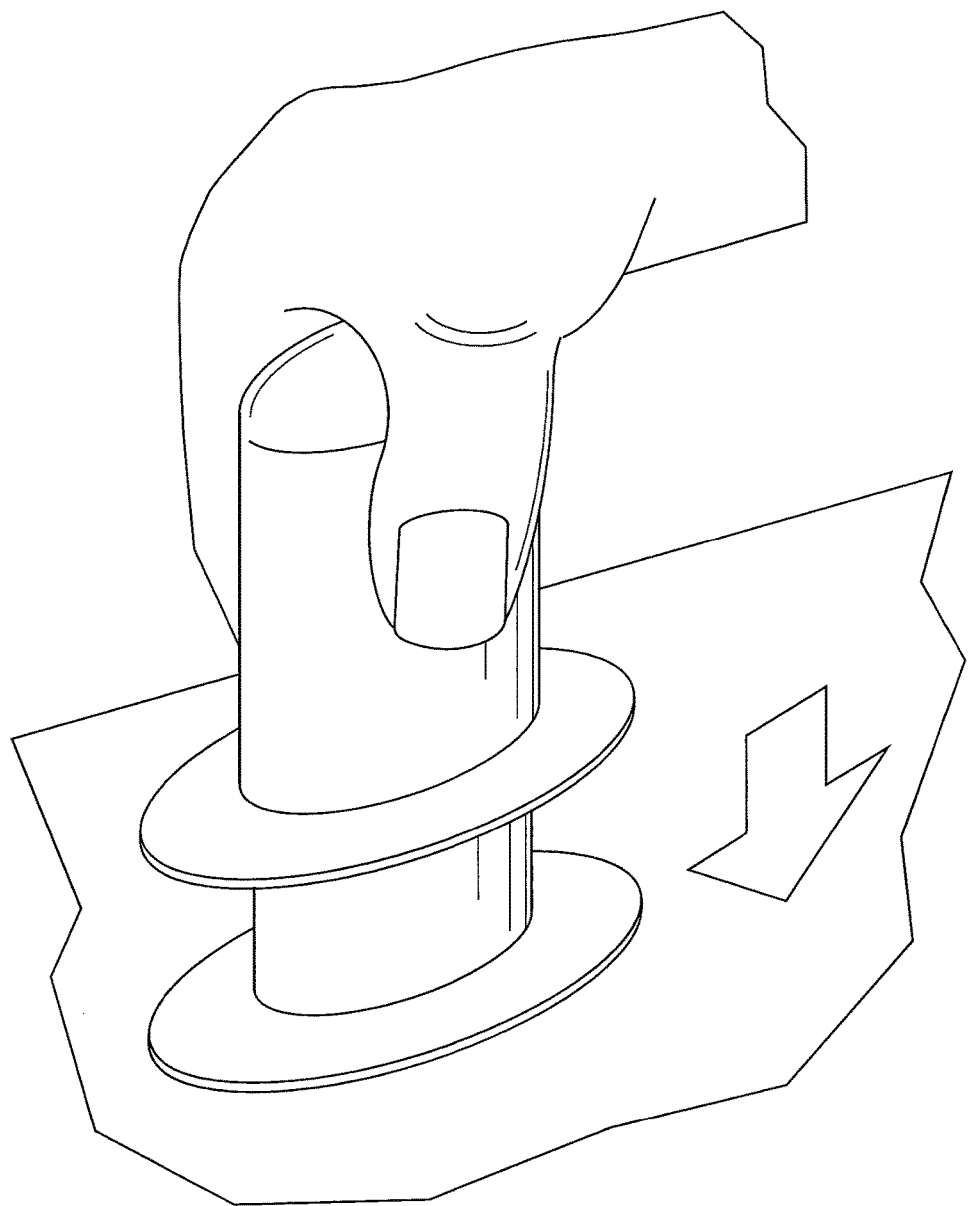
FIG. 35 is a perspective view of a second variation of the fifth exemplary embodiment of an injection device of the present disclosure. Here, the housing is elliptical instead of cylindrical.

FIGS. 32-38 illustrate a fifth exemplary embodiment of an injection device of the present disclosure. FIG. 32 is a perspective view of one variation of this fifth exemplary embodiment. Generally, the injection device 900 includes a housing 910 having a base end 912 and a top end 914. A lower flange 926 extends radially from the base end of the housing, and acts as a needle shield. An upper flange 906 is also present, and may be considered to be an external grip or injection ring or button that operates similar to the traditional syringe plunger. FIG. 33 depicts the injection device being placed against the stomach of a user. FIG. 34 depicts the usage of the injection device. Generally, the upper flange 906 is pushed downwards towards the lower flange 926. This causes the needle to be inserted and fluid to be dispensed. FIG. 35 is a perspective view of another variation of this fifth exemplary embodiment. Whereas the variation in FIG. 32 has a cylindrical shape between the base end and the top end, the variation of FIG. 35 has an elliptical shape instead. Again, the housing may be transparent or contain a viewing window for viewing the interior of the housing. In FIG. 32, the portion of the housing above the upper flange is a viewing window 911.

Figure 36:
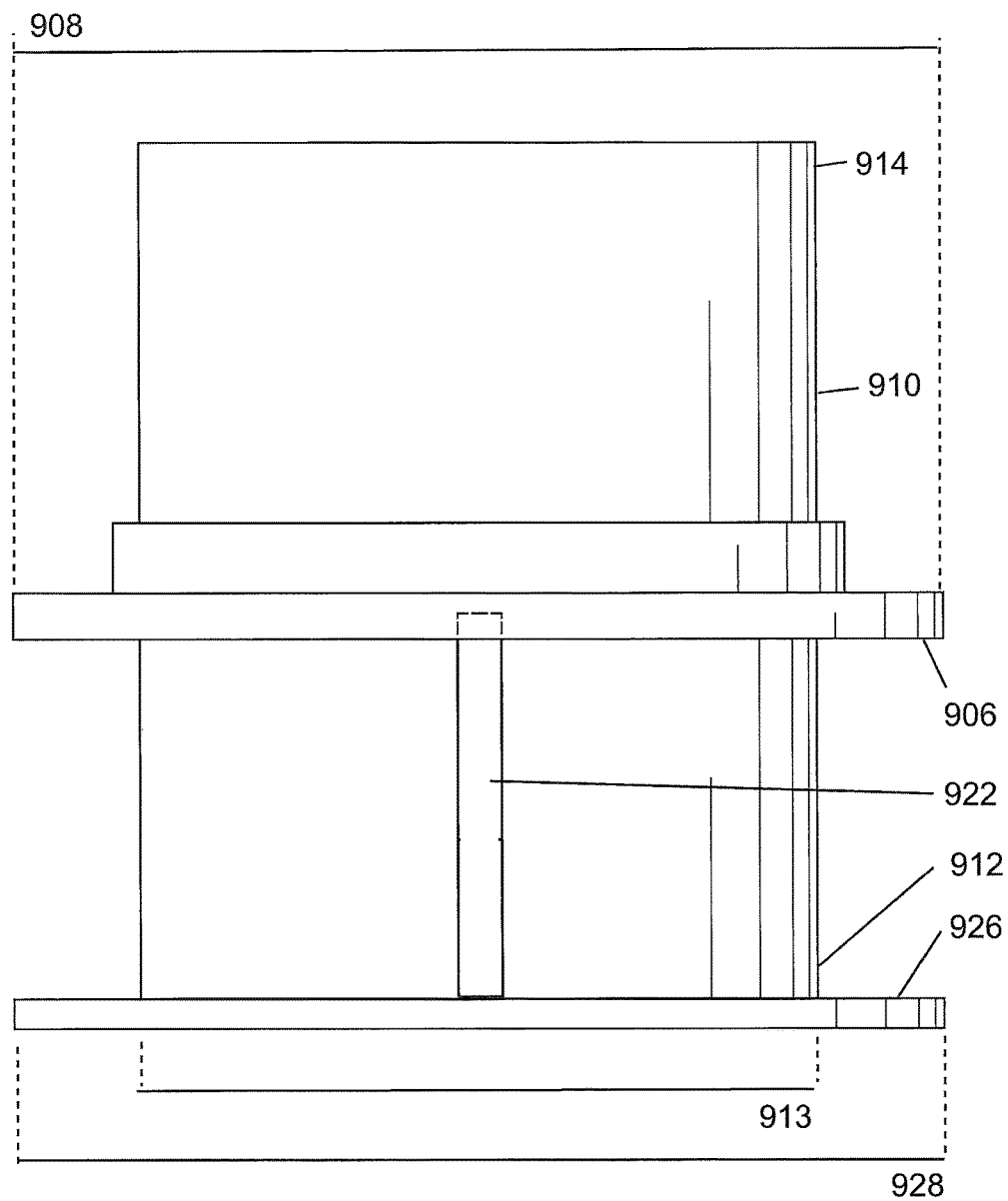
FIG. 36 is an exterior side view of the fifth exemplary embodiment of FIG. 33.

FIG. 36 is an exterior side view of the variation of FIG. 32. The housing 910 has a base end 912 and a top end 914. A lower flange 926 extends radially from the base end 912 of the housing. Again, the lower flange can be a full disk shape and be located below the base end of the housing, or alternatively have an annular shape and be located around the housing at the base end. In embodiments, the width 928 of the lower flange is at least twice the width 913 of the base end 912 of the housing. If the housing and the lower flange are cylindrical, the width would correspond to the diameter. In some embodiments, the width 928 of the lower flange is from about 2 inches to about 4 inches, including about 2.5 inches.

The external grip/upper flange 906 may have the same width 908 as the lower flange, or have a smaller width. In some embodiments, a stop may be present within the housing to prevent the upper flange from contacting the lower flange. This leaves room between the upper flange and the lower flange for a second hand to stabilize the injection device. Alternatively, in other embodiments, the upper flange 906 contacts the lower flange 926 upon being depressed fully, and the user holds the housing at the top end 914 (as shown in FIG. 34). The upper flange 906 is attached to a lever that passes through the housing 910. Put another way, the upper flange is attached to the lever outside the housing. A shaft 922 is seen here for the lever to travel up and down with respect to the housing. The upper flange 906 is an annulus that surrounds the housing. Both the lower flange and the lower flange extend around the entire housing.

Figure 37:
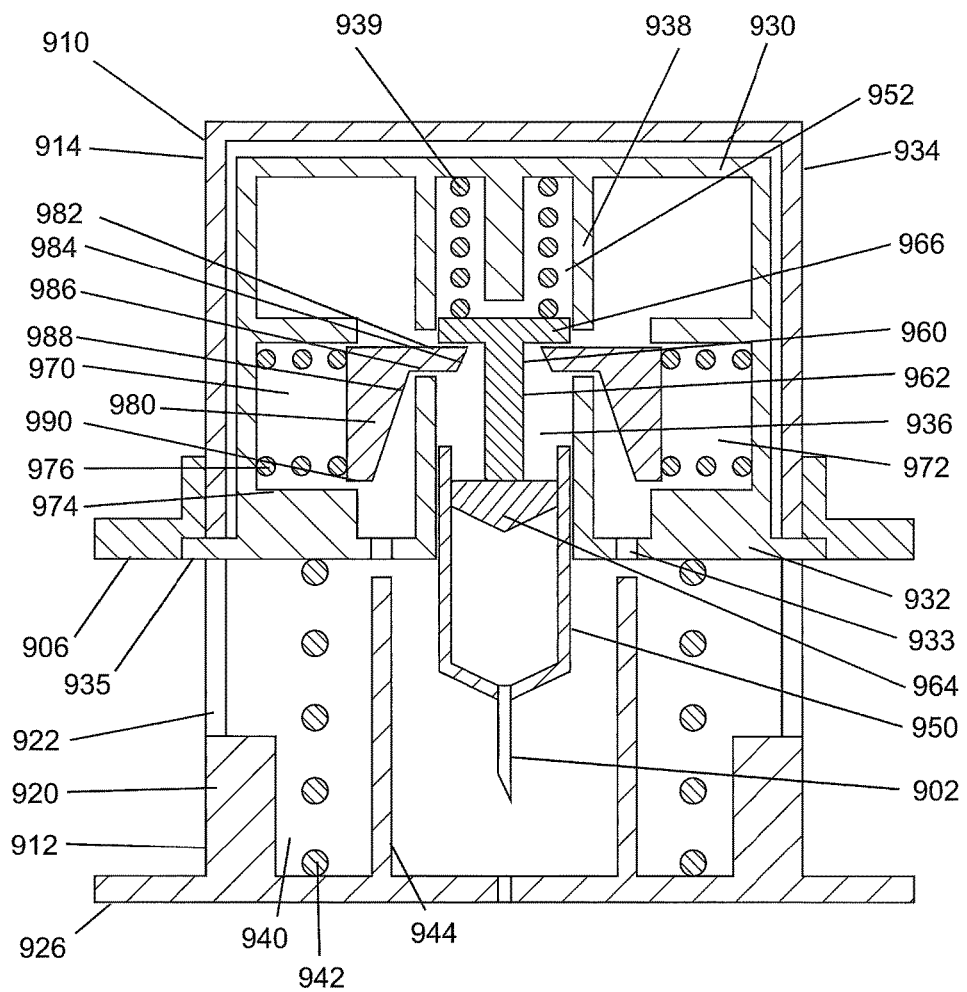
FIG. 37 is a side cross-sectional view of the fifth exemplary embodiment, showing the internal components in an initial state.

FIG. 37 is a cross-sectional side view illustrating one possible mechanism within this fifth exemplary embodiment. Again, the housing 910 has a base end 912 and a top end 914 located on opposite sides. The housing is formed from a sidewall 920. A shaft 922 is present in the housing for the lever 935 to extend through. A needle 902 can protrude through an opening (not shown) in the base end.

A hull 930 is present within the housing. The hull 930 has a lower end 932 and an upper end 934 located on opposite sides. The lever 935 extends radially from the lower end 932 of the hull through the housing 910 and is attached to the upper flange 906. A biasing mechanism 940 biases the hull away from the base end 912 of the housing. The hull 930 contains the barrel 950, a plunger 960 slidably received within the barrel, and an injection drive 952 for automatically ejecting a fluid through a needle. In FIG. 37, the mechanism is in its initial storage state.

The biasing mechanism 940 includes a return spring 942 and an inner sleeve 944. The return spring 942 is located between the housing sidewall 920 and the inner sleeve 944. The return spring 942 is a compression spring and is extended in this initial state. The return spring 942 contacts the lower end 932 of the hull and the base end 912 of the housing.

The plunger 960 includes a shaft 962, a piston 964 at the bottom end of the shaft, and a thumbrest 966 at a top end of the shaft. The piston 964 is located within the barrel 950. A drive spring 939 acts between the thumbrest 966 and the upper end 934 of the hull. The drive spring 939 is a compression spring which is compressed in the initial state (i.e. storing energy).

The barrel 950, plunger 960, and drive spring 939 are located within a central channel 936 in the hull. The central channel 936 is surrounded by, or defined by, a channel sidewall 938. The central channel 936 runs from the upper end 934 to the lower end 932 of the hull. The barrel 950 is fixed in place at the lower end 932 of the hull.

A locking mechanism 970 prevents the drive spring 939 from depressing the plunger in the initial state. This locking mechanism is located between the piston 964 and the thumbrest 966, and is depicted as a pair of locks 980 extending through the channel sidewall 938. Each lock 980 includes a top stop surface 982 upon which the thumbrest sits. A top tapered surface 984 runs from the top stop surface towards the hull away from the central channel. A bottom tapered surface 988 runs from an intermediate flat surface 986 down to a lower surface 990 of the lock. The locks are located within a lock cavity 972 on the side of the hull formed by two lock surfaces 974 that extend towards the hull. A locking spring 976 is located within the lock cavity to bias each lock towards the channel sidewall. The locking spring 976 is a compression spring which is extended in the initial state. The drive spring 939 should not be so wide as to be able to contact the locks.

The lower end 932 of the hull includes a passage 933. The inner sleeve 944 can extend through this passage to disengage the locking mechanism 970.

Figure 38:
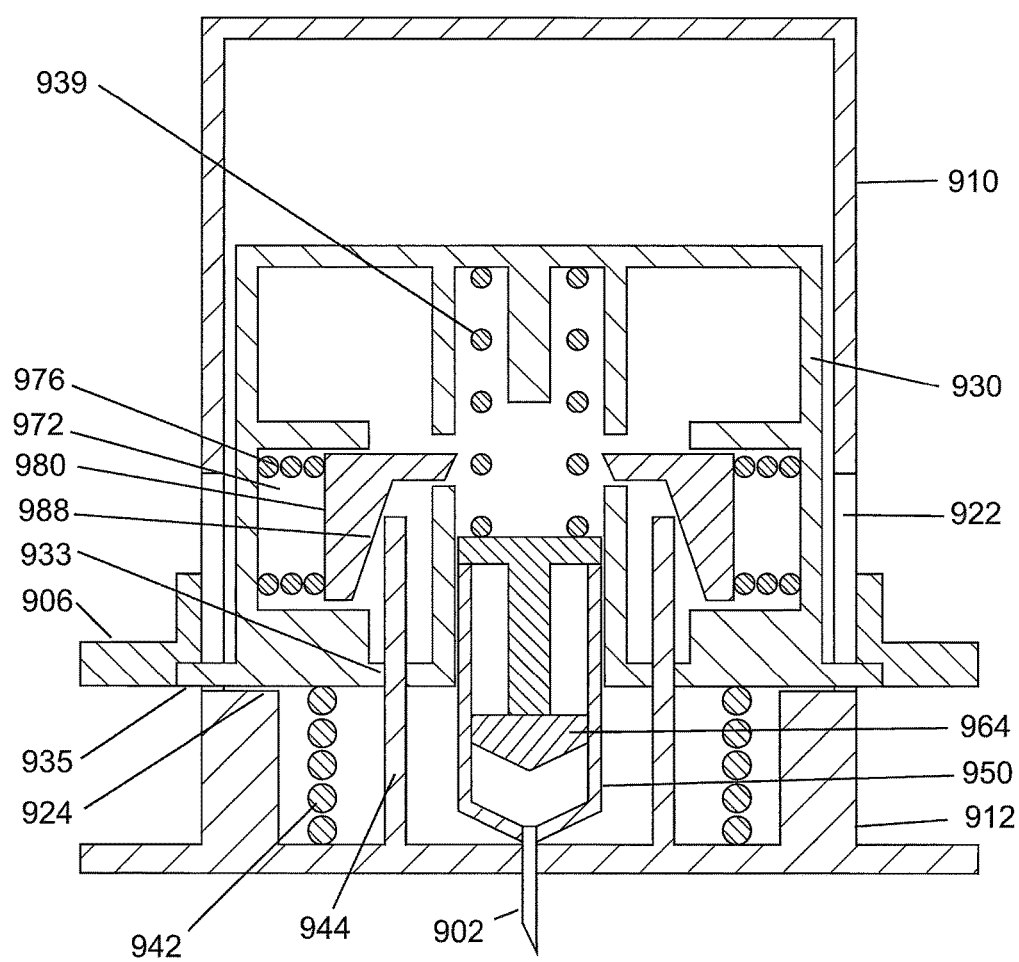
FIG. 38 is a side cross-sectional view of the fifth exemplary embodiment, showing the internal components after the upper flange has been depressed and the device has been activated.

FIG. 38 illustrates the mechanism after the upper flange has been depressed to activate the injection device. The downward motion on the upper flange 906 is transmitted through the lever 935 to the hull inside the housing, and is now at the bottom of the shaft 922. As the hull travels downward, the needle 902 protrudes through the base end 912. The inner sleeve 944 on the base end of the housing also travels through the passage 933 in the lower end of the hull. The inner sleeve 933 then pushes against the bottom tapered surface 988 of each lock to compress the locking spring 976 and push the lock 980 away from the central channel and into the lock cavity 972. Once the locks are withdrawn, the drive spring 939 is able to extend, pushing the piston 964 through the barrel 950 and dispensing fluid in the barrel through the needle. A stop surface 924 is shown here on the housing sidewall 920 to prevent the upper flange 906 from contacting the lower flange 926, though as discussed there may be no stop surface as well. The return spring 942 is also compressed.

When pressure is released from the upper flange 906, the return spring 942 will extend to push the hull 930 upwards and away from the base end 912 of the housing, retracting the needle. In this regard, the return spring 942 is stronger than the drive spring 939. As the hull moves upwards, the inner sleeve 944 withdraws. Although this may permit the locks 980 to re-engage the channel sidewall 938, this should not prevent the drive spring from being re-compressed.

Again, other internal mechanisms may be possible, such as the chemical reaction systems described further below.

Figure 39:
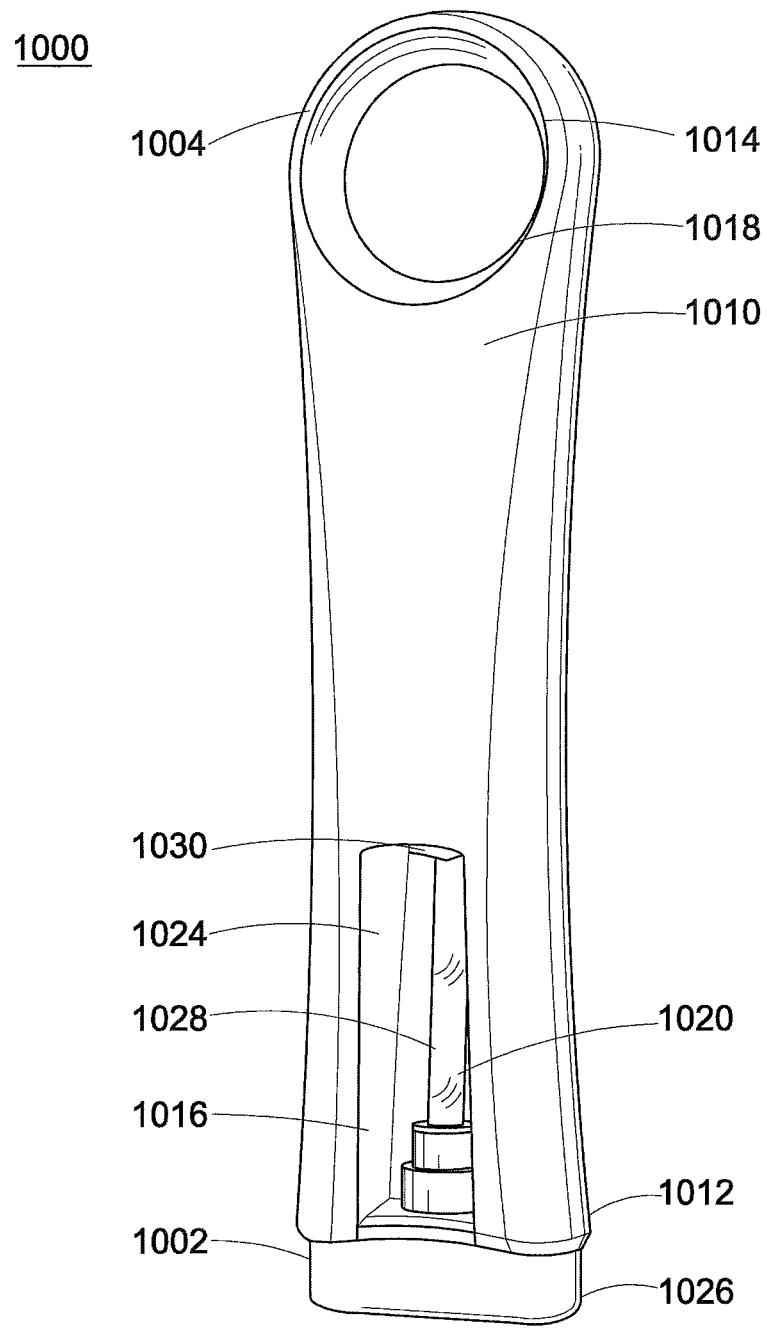
FIG. 39 is a perspective view of a sixth exemplary embodiment of an injection device of the present disclosure.
Figure 40:
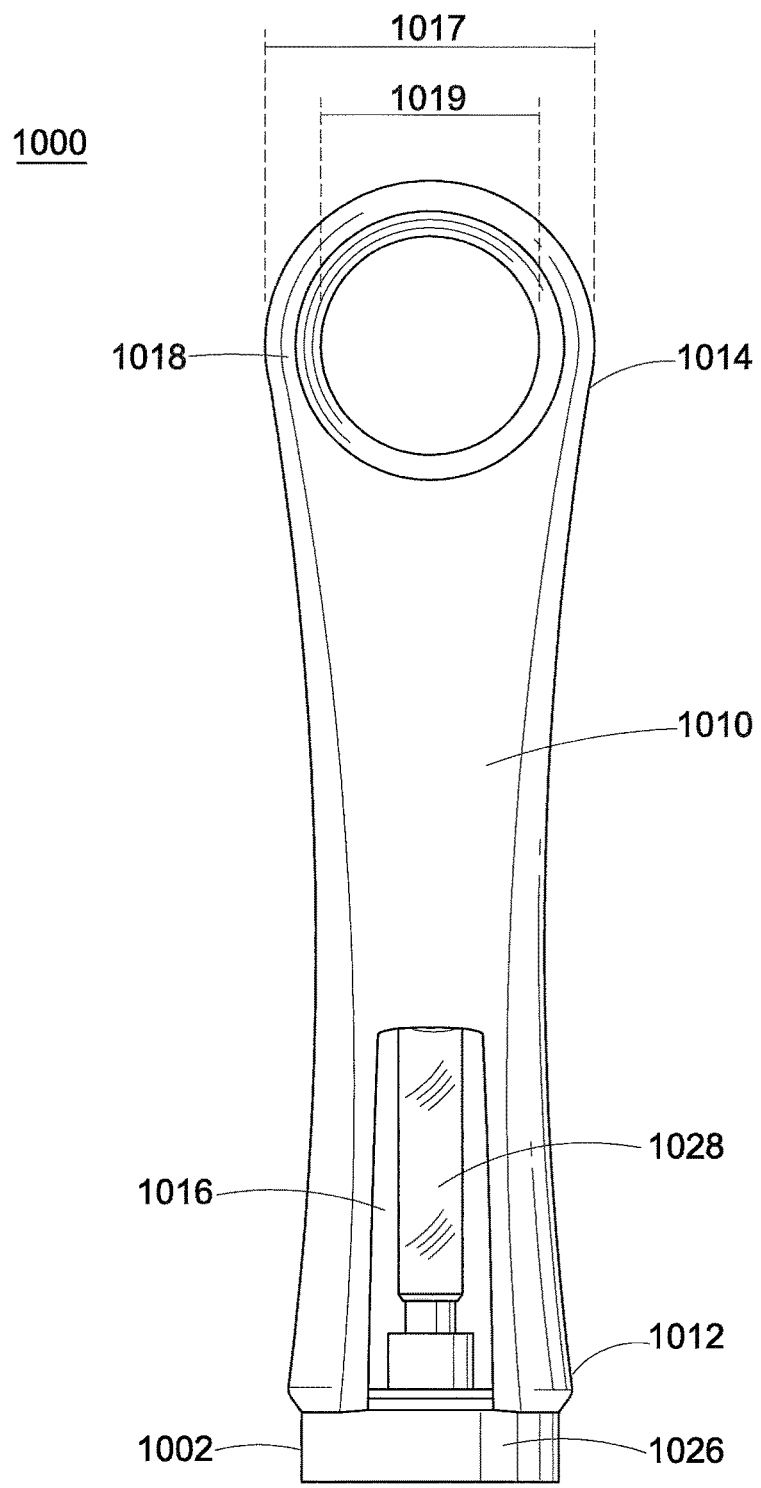
FIG. 40 is a front view of the sixth exemplary embodiment of an injection device of the present disclosure.

FIG. 39 and FIG. 40 provide additional views of another exemplary embodiment of an injection device of the present disclosure having ergonomic enhancements. The overall injection device 1000 has a base end 1002 and a top end 1004. An outer housing 1010 is present and surrounds a hull 1020. The base 1026 of the hull is visible here below the outer housing. In use, the base end 1002 of the injection device (i.e. the base 1026 of the hull) is placed against the skin at the injection site.

The outer housing 1010 has a lower end 1012 and an upper end 1014. A cutout or transparent window 1016 is present at the lower end so that the hull (i.e. the inner mechanism) is visible. The upper end 1014 of the outer housing includes a grip 1018, which is shown here as being ring shaped. The grip is sized to be easily grasped and to be comfortable. In embodiments, the grip may have an outer diameter 1017 of about 1 and ⅝ inches, and the inner diameter 1019 of the grip may be about ⅞ inches.

The base 1026 of the hull contains the needle (not visible), which is retractable. The hull 1020 contains the operating mechanism. A fluid chamber 1028 is visible, and contains the medication. A piston 1030 is located at the upper end 1024 of the fluid chamber. A penetration drive is present for inserting the needle and pushing the piston through the fluid chamber. The hull itself may be transparent for viewing its internal components.

The device is activated by pushing the outer housing 1010 downwards towards the base 1026 of the hull. The base of the hull may be considered as retracting into the outer housing to start the needle insertion and injection processes. The piston 1030 travels through the fluid chamber 1028 using various mechanical or chemical mechanisms.

Figure 41:
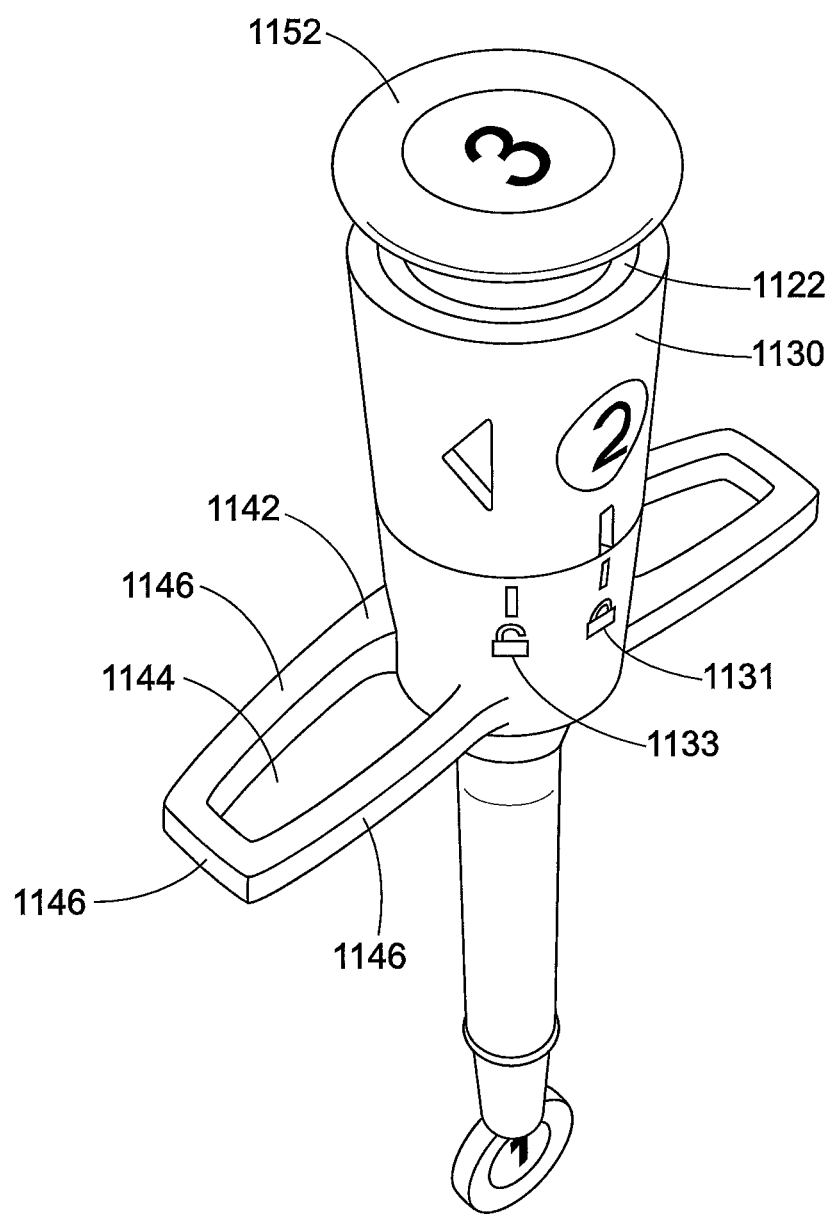
FIG. 41 is a perspective view of a seventh exemplary embodiment of an injection device of the present disclosure.
Figure 44:
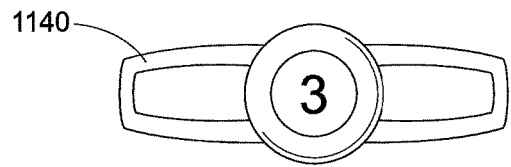
FIG. 44 is a top view of the seventh exemplary embodiment of an injection device of the present disclosure.
Figure 43:
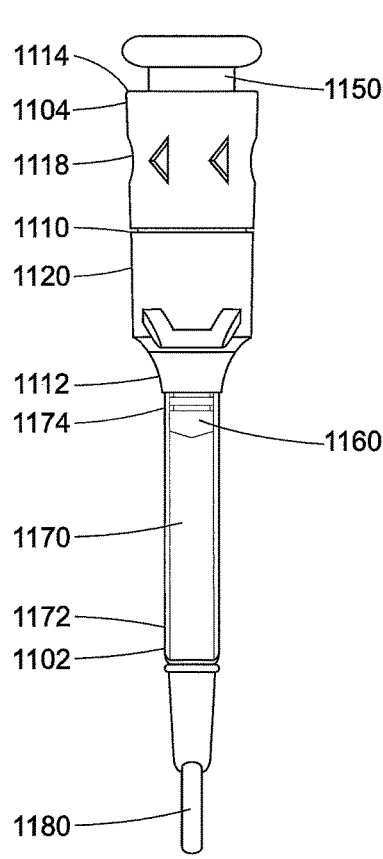
FIG. 43 is a side view of the seventh exemplary embodiment of an injection device of the present disclosure.
Figure 42:
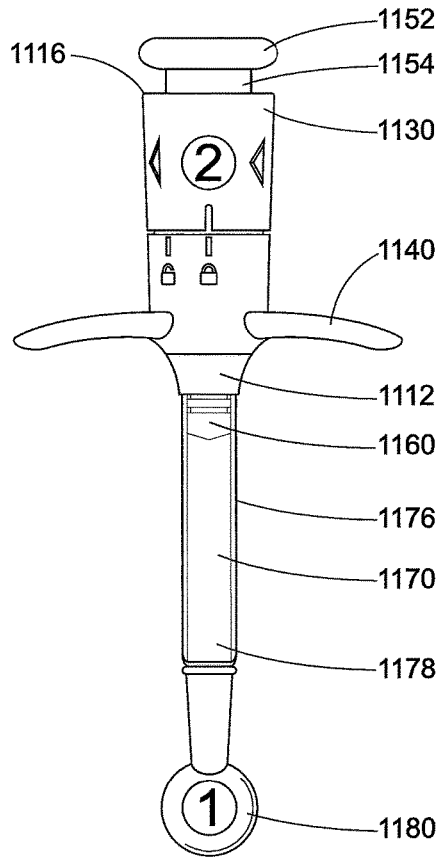
FIG. 42 is a front view of the seventh exemplary embodiment of an injection device of the present disclosure.

FIGS. 41-44 illustrate another exemplary embodiment of an injection device. FIG. 41 is a top perspective view. FIG. 42 is a front view. FIG. 43 is a side view. FIG. 44 is a plan view. The injection device 1100 here is an auto-syringe which is depicted in a storage state or a non-depressed state, in which the fluid/medication has not yet been dispensed.

The syringe 1100 may be considered as being formed from a barrel 1110 and a vial 1170, with one end of the barrel defining a top end 1104 of the syringe and one end of the vial defining a bottom end 1102 of the syringe. The barrel itself has an upper end 1114 and a lower end 1112. The vial also has an upper end 1174 and a lower end 1172. The upper end 1174 of the vial engages the lower end 1112 of the barrel. The barrel is generally wider than the vial, and is intended for gripping and handling by the user.

Referring to FIG. 42, a push button 1152 extends from an upper surface 1116 of the barrel. The push button itself is part of the plunger 1150, which also includes a plunger shaft 1154. The barrel 1110 itself can be considered as being divided into two portions, an upper portion 1118 and a lower portion 1120. The upper portion is located closer to the top end 1104 of the syringe than the lower portion. The lower portion includes two handles 1140 extending from opposite sides of the barrel. Seen from the front view of FIG. 42, each handle has an arcuate curve, curving downwards towards the lower end of the barrel at an angle of from about 1 degree to about 5 degrees (relative to a radial plane). Seen from the perspective view of FIG. 41 and from the top view of FIG. 44, each handle 1140 has a rectangular shape, with three sides 1146 and a central cutout 1142. Alternatively, each handle 1140 could be described as being formed from a strand 1144 that is bent to make three sides 1146.

The upper portion 1118 of the barrel includes a twist ring 1130 on the exterior surface 1122 of the barrel. The twist ring acts as a lock that controls whether the push button 1152 can be depressed to activate the syringe. As seen here, in a first position the push button is locked (indicated by locked icon 1131), and in a second position the push button is unlocked (indicated by unlocked icon 1133). It is contemplated that color coding will be used. For example, the locked icon would be red, while the unlocked icon would be green. The twist ring 1130 rotates around the upper portion 1118 of the barrel, which is stationary relative to the twist ring. It should be noted that the push button extends beyond the twist ring.

The vial 1170 of the syringe is formed from a sidewall 1176 that defines a fluid chamber 1178 which holds the fluid or medication to be dispensed by the syringe. The needle (not visible) is located at the bottom end of the syringe, or at a lower end 1172 of the vial. A piston 1160 is visible at the upper end 1174 of the fluid chamber, or at the lower end 1112 of the barrel. It is contemplated that the vial is usually transparent, so that the contents of the vial are visible and the user can know the amount that has, been dispensed.

Finally, a needle cap 1180 is shown for covering the needle. It is contemplated that the needle may be fixed in place or may be automatically inserted/retracted from the lower end of the vial.

The syringe is prominently labeled with universally understood symbols to increase ease of use. Referring to FIG. 42, the needle cap 1180 is labeled with the number "1", indicating that the first step to using the syringe is to remove the needle cap. The twist ring 1130 is labeled with the number "2", indicating that twisting is the second step, with carved triangles indicating the direction to turn the twist ring. Twisting unlocks the push button 1152. As best seen in FIG. 44, the push button is labeled with the number "3" indicating that the third step to use the syringe is to depress the push button.

Regarding the internal workings of the syringe, it is contemplated that the barrel would be separated into two chambers in the storage state, with the plunger and the twist ring locked position being used to maintain the separation. For example, the other end of the plunger shaft may form part of the barrier between the two chambers. The twist ring can be used to lock the plunger in place using known structures. One chamber would contain a liquid reagent, while the other chamber would contain a dry reagent. When the push button is depressed, the two chambers would be joined together so the liquid reagent and the dry reagent could mix. A gaseous byproduct is generated from a chemical reaction between the liquid reagent and the dry reagent. The additional force generated by the gas pressure will eventually push on the piston, causing the piston to travel through the vial and push the fluid/medication in the vial through the needle. An example of the liquid reagent is a bicarbonate which has been pre-dissolved in a solvent, such as water. An example of the dry reagent is a dry acid powder, such as citrate. If desired, a release agent such as sodium chloride (NaCl) can be included with the dry reagent to provide nucleation sites that allow the gas to evolve from solution more quickly.

FIG. 45 and FIG. 46 show another embodiment of an injection device that is wearable. FIG. 45 shows the injection device in its assembled form, while FIG. 46 shows the device with its two components separated from each other.

It is contemplated that this injection device 1200 is in the form of a device that can be worn on the arm of the user, but aesthetically resembles a fashion accessory rather than a medical device. The device includes two separate components, a control interface 1210 and a medication band 1220. The control interface is reusable, while the medication band is replaceable. The control interface forms an outer surface 1202 of the device, while the medication band forms the inner surface 1204 of the device which contacts the skin of the user.

The control interface 1210 is intended to be durable and contain the electronics, electronic display, and other controls needed for the injection device. For example, as illustrated here, the control interface can act as a watch by providing day and time information (reference numeral 1216). The control interface includes an exterior surface 1212 and two side surfaces 1214, which cooperate with the medication band.

The medication band 1220 acts as a replaceable medicine bladder. The medication band is formed from a strip 1222 that includes a microchip 1224, microneedles 1226, and sensors 1228. The microchip is flexible and contains readable information, such as the medication, dosage, batch, etc. The microneedles 1228 are used to dispense medication from one or more reservoirs 1230 into the user's skin. The sensors can be used to obtain patient information such as temperature, pulse rate, etc. for reporting to the control interface.

Figure 47:
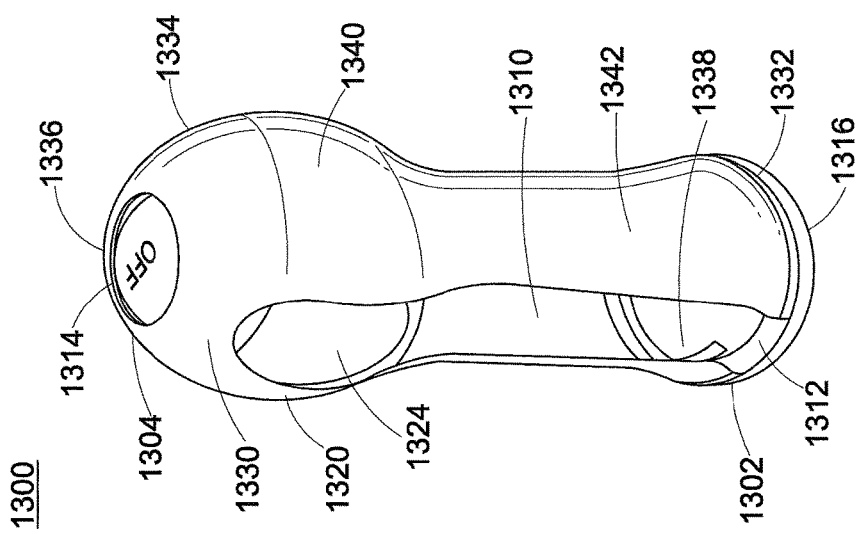
FIG. 47 is a perspective view of a ninth exemplary embodiment of an injection device of the present disclosure in an off state.

FIG. 47 is a perspective view of another exemplary embodiment of an injection device. The device 1300 here includes a hull 1310 and an outer twist ring 1330. The device 1300 has a top end 1304 and a bottom end 1302. The hull 1310 runs from the top end to the bottom end of the device, and has an upper end 1314 and a lower end 1312. The outer twist ring 1330 also runs from the top end to the bottom end of the device, and has an upper end 1334 and a lower end 1332. The upper end of the hull is adjacent the upper end of the outer twist ring, and their lower ends are adjacent as well.

A ridge or flange 1316 extends radially from the lower end 1312 of the hull. This flange may be integral to the hull, or can be a separate piece attached to the hull. In embodiments, the flange may have a width 1315 of from about 2 inches to about 4 inches, including about 2.5 inches. It should be noted that the flange extends around the entire lower end. The upper end 1314 of the hull includes a bulb 1320, or in other words has a bulbous shape. The bulb can be divided into quadrants. It is contemplated that two opposite quadrants of the bulb are made from a soft squeezable material 1322, while the other two quadrants 1324 are made from a relatively rigid material. The hull may be transparent so that the fluid/medication is visible and the dosage can be seen by the user.

The upper end 1334 of the outer twist ring is a contoured shell 1340 that conforms to the bulb 1320 of the hull. The top of the outer twist ring includes a cutout or transparent window 1336 that exposes the top 1321 of the bulb. This exposes a display 1318 located in the hull 1310 to be seen by the user. The outer twist ring 1330 extends from the top end 1304 of the device to the bottom end 1302 of the device. Two longitudinal cutout sections 1338 are present in the outer twist ring that expose the hull. Put another way, two curtains 1342 hang from the contoured shell 1340 of the outer twist ring. The cutout sections 1338 extend from the lower end of the twist ring to a height sufficient to expose the squeezable quadrants 1322 of the hull. This permits the dosage to be viewed by the user. The outer twist ring is made from a relatively rigid material as well.

FIG. 47 illustrates the injection device in a storage state. Here in this first position, the outer twist ring 1330 is rotated to cover the squeezable quadrants 1322 of the hull, so that the rigid quadrants 1324 are present on the exterior of the device. This state is indicated as "OFF" in the display on the top.

Figure 48:
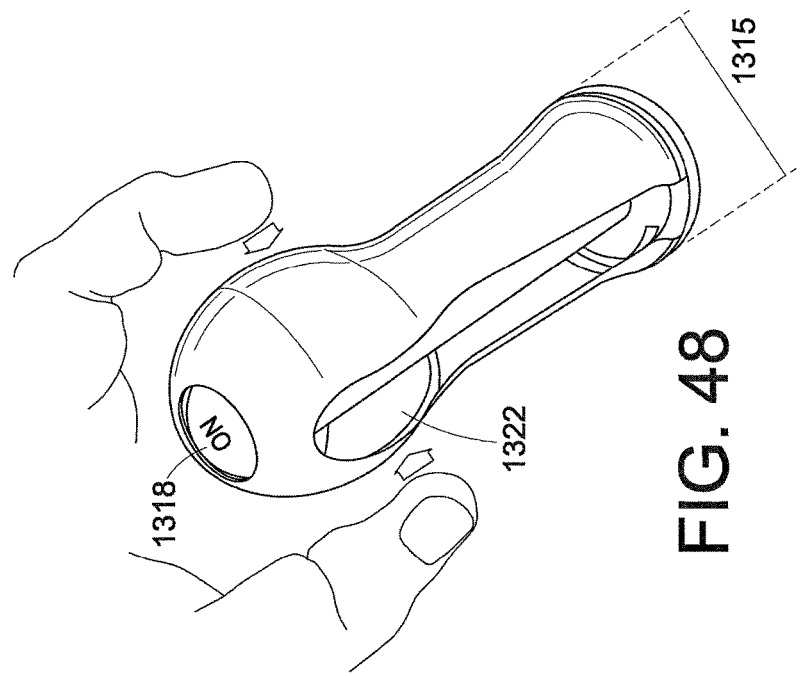
FIG. 48 is a perspective view of the ninth exemplary embodiment in an on state.

FIG. 48 illustrates the injection device in a usage state. Here, the outer twist ring 1330 is rotated 90 degrees so that the curtains 1342 of the outer twist ring align with the rigid quadrants 1324 of the bulb, and the cutouts 1338 align with the squeezable quadrants 1322. Put another way, in this second position the outer twist ring exposes the squeezable quadrants. This state is indicated as "ON" in the display on the top. The bulb 1320 can then be squeezed to activate the syringe. For example, the squeezing motion can be used to break a barrier between two compartments that causes mixing and gas generation to occur, pushing on a piston that ejects fluid, as described above.

Figure 49:
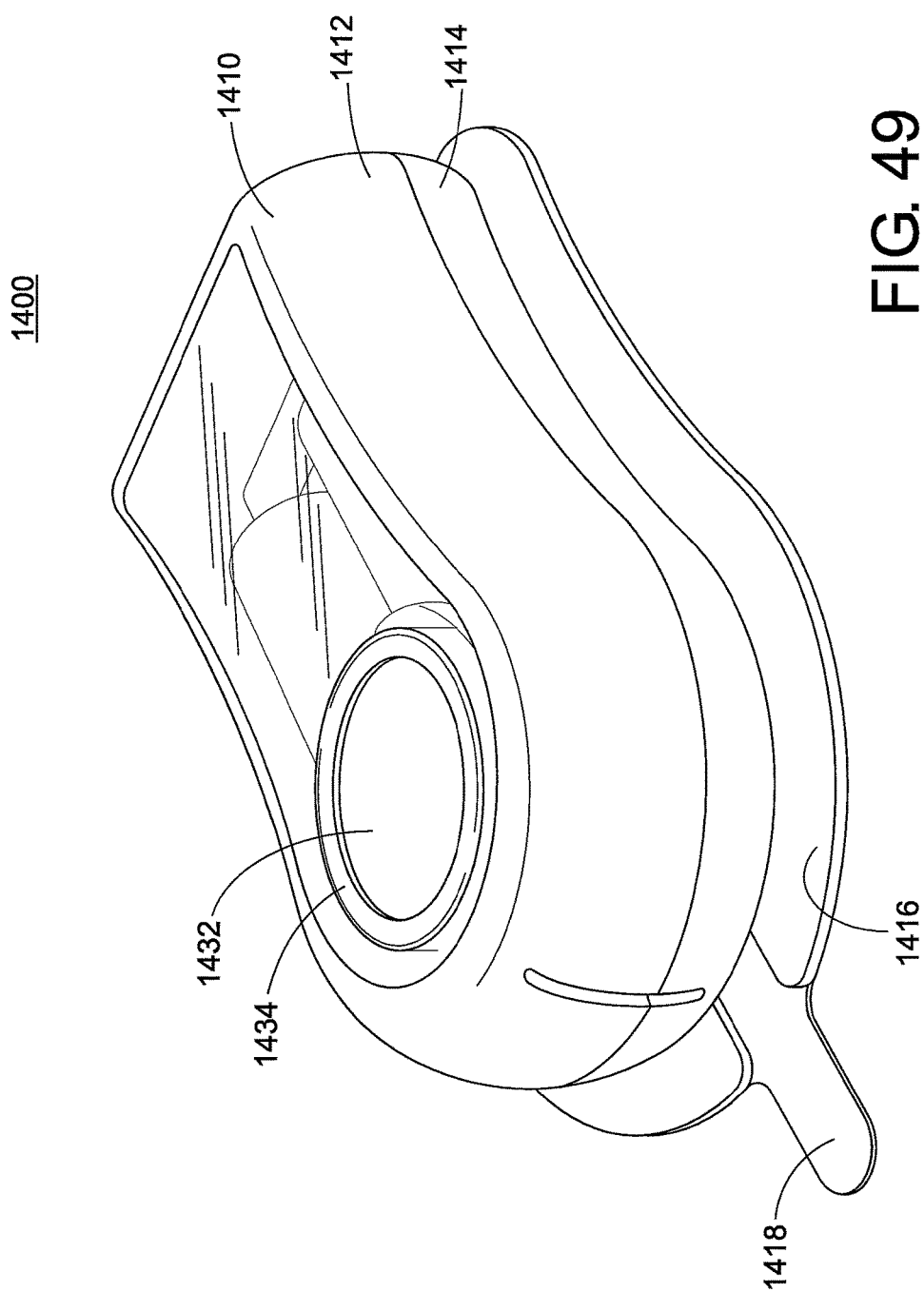
FIG. 49 is an assembled perspective view of a tenth exemplary embodiment of an injection device of the present disclosure, in the form of a patch pump.
Figure 50:
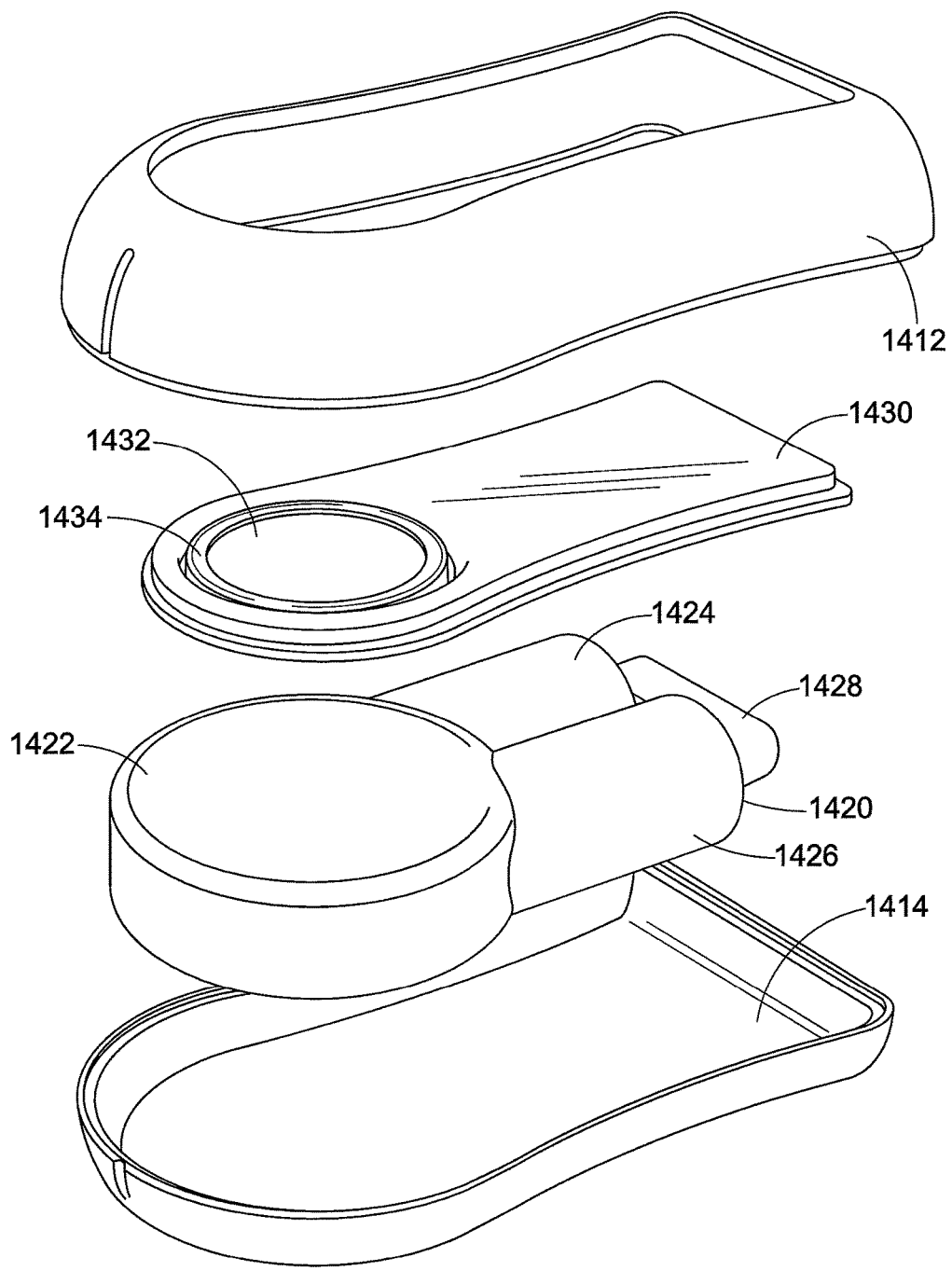
FIG. 50 is an exploded view of the patch pump of FIG. 50.

FIG. 49 and FIG. 50 illustrate another embodiment of an injection device. FIG. 49 is a perspective assembled view, while FIG. 50 provides an exploded view of the device. This device is in the form of a wearable single-use patch pump.

The device 1400 includes a housing 1410 that surrounds the various components. The housing as illustrated here as being formed from a top piece 1412 and a bottom piece 1414. An adhesive patch 1416 is present on the bottom surface of the housing. In storage, the adhesive patch is covered by a thin film (not visible) to which is attached a pull tab 1418. The pull tab extends from one side of the perimeter of the device, and can be easily grasped by the user's fingers to expose the adhesive. The pull tab and thin film can be made from a hypoallergenic plastic film or other known materials.

Referring now to FIG. 50, located within the housing is the pump 1420, which comprises a reagent chamber 1422, a reaction chamber 1424, and a fluid chamber 1426. As shown here, the reagent chamber is located to one end of the reaction chamber and the fluid chamber. The reagent chamber is fluidly connected to the reaction chamber, but not to the fluid chamber. The reaction chamber and the fluid chamber are located side-by-side, though this can vary as desired. The reagent chamber can be considered to be oriented in a longitudinal axis, with the reaction chamber and the fluid chamber being oriented in a radial axis. The reaction chamber 1424 and the fluid chamber 1426 are fluidly connected by a passage 1428 at the end opposite that of the reagent chamber. The fluid chamber includes an outlet that is connected to a needle (not shown), which will extend from the bottom surface of the housing. A protective layer 1430 can be included to cover the pump 1420. The protective layer includes a button 1432 which is located above the reagent chamber. The button may be surrounded by a ring 1434.

It is contemplated that this pump will operate using a chemical reaction system similar to that described above. The reagent chamber 1422 and the reaction chamber 1424 each contain reagent, and are divided by an internal barrier (not visible). A gas-generating chemical reaction can be initiated by breaking the barrier between these two chambers. The barrier could be broken, for example, by pushing the button 1432 to increase pressure and break the barrier. This would cause the reagents in these chambers to mix. The gas pressure builds up and acts on a piston (not visible) in the fluid chamber 1426, causing fluid to exit through the needle. When the delivery of fluid/medication is complete, the ring 1434 would pop up to indicate completion. The needle may be fixed in place, or can be an auto-retractable needle.

Figure 52:
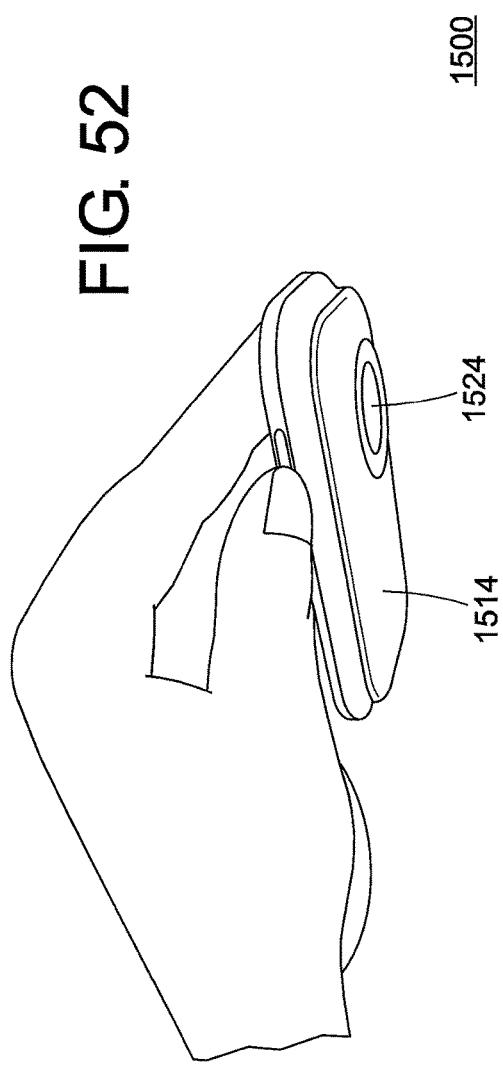
FIG. 52 is a bottom perspective view of the embodiment of FIG. 52.
Figure 51:
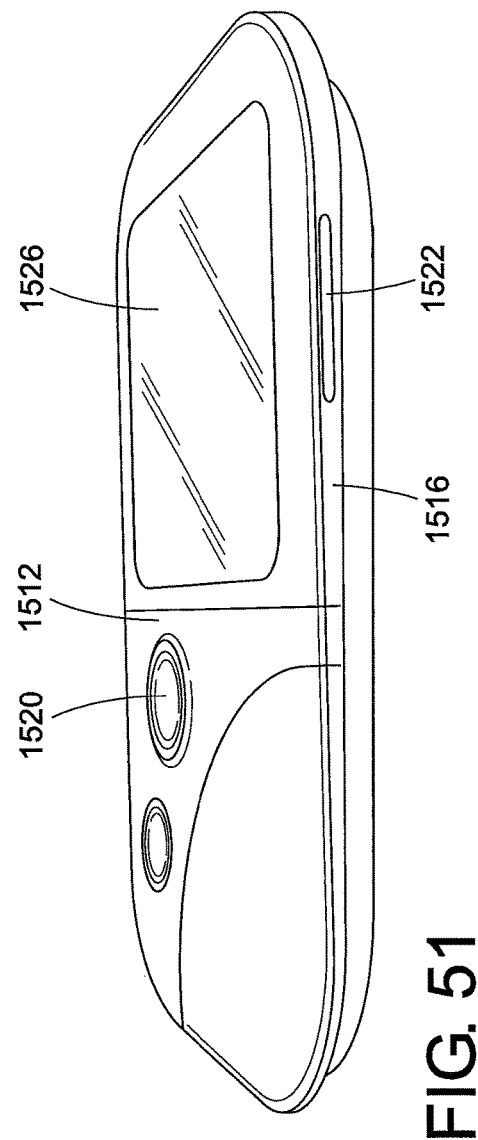
FIG. 51 is a top perspective view of an eleventh exemplary embodiment of an injection device of the present disclosure.

FIG. 51 and FIG. 52 are perspective views of another exemplary embodiment of an injection device. FIG. 51 shows the top, while FIG. 52 also permits the bottom to be seen. This device 1500 is contemplated to be a digital auto-injector, and does not physically attach to the user's skin using an adhesive. One end of the top surface 1512 of the housing can include a display 1526, such as an LCD. An injection button 1520 is also located on the top surface. A secondary button 1522 is located on a side surface 1516 of the housing (here, the right side). As seen in FIG. 52, the injecting site 1524 of the device is located on the bottom surface 1514 of the housing. The injecting site may be, for example, a patch of microneedles attached to a drug reservoir inside the device. There may be one or multiple reservoirs. It is contemplated that the injection device can be reusable, or that the injecting site could be a disposable patch. The injection device could be used to monitor the medication history of the device. For example, the device could record the dosage of a particular injection, the medicine injected, the date/time of the injection, etc. The display could provide useful information to the user.

Figure 53:
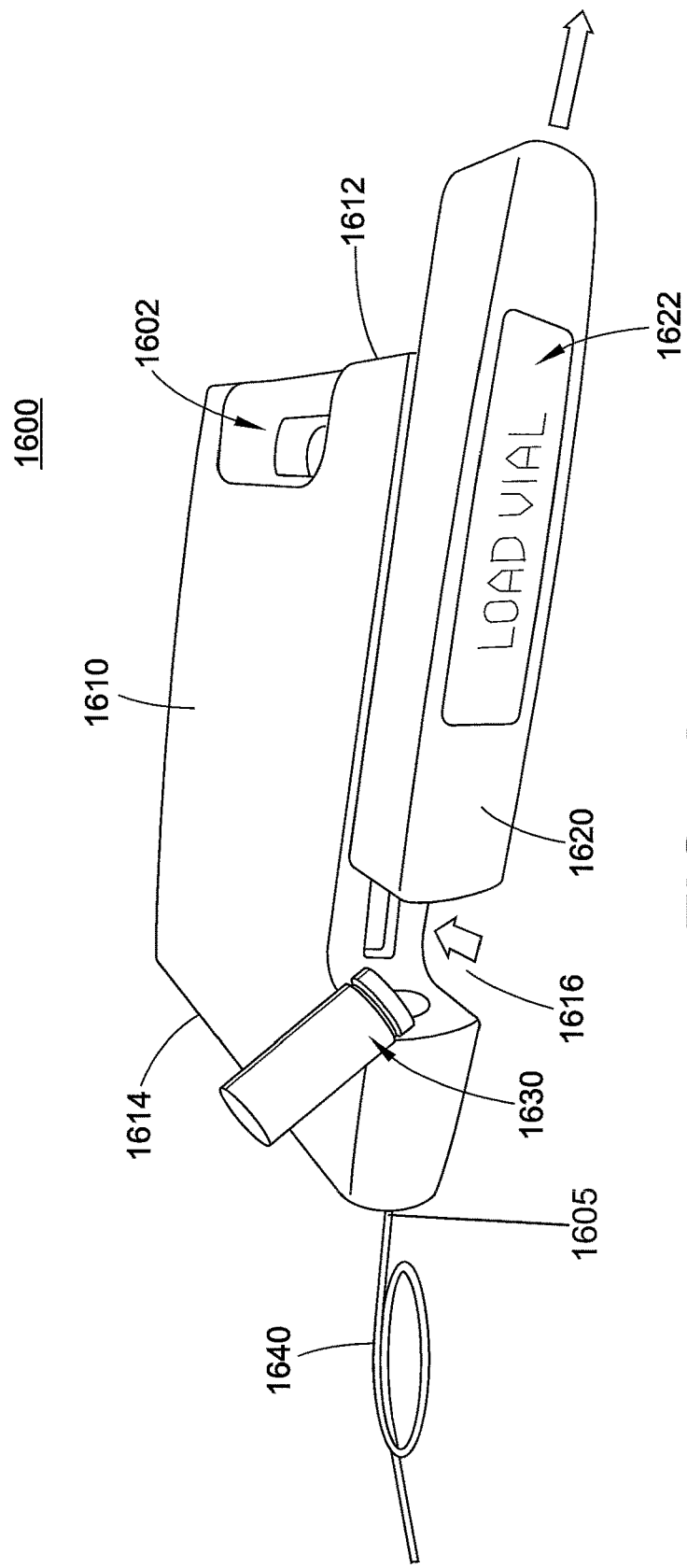
FIG. 53 is a perspective view of a twelfth exemplary embodiment of an injection device of the present disclosure.

FIG. 53 is another exemplary embodiment of an injection device of the present disclosure. This device 1600 is a home infusion pump with a compact form factor. As illustrated here, this device has a relatively rectangular housing 1610 with rounded surfaces and corners. A top side 1612 of the device includes a carrying handle 1602. A front side 1616 of the device includes a sliding door 1620 that extends from the top side when in an open position. A vial or cartridge 1630 containing the fluid/medication can be inserted into the device when the door is opened. The door also includes a display 1622, such as an LCD, that can be used to display certain information or instructions such as "LOAD VIAL". The fluid/medication is dispensed through an outlet 1605 on the housing that can be located on any side of the pump, including the front side 1616 or the bottom side 1614 or the top side 1612. The delivery tube 1640 is also visible here.

FIGS. 54-57 are variations of another embodiment of an injection device of the present disclosure, in which the injection device is configured to communicate with a smart device, such as a smartphone, tablet computer, or regular desktop or laptop computer.

Figure 54:
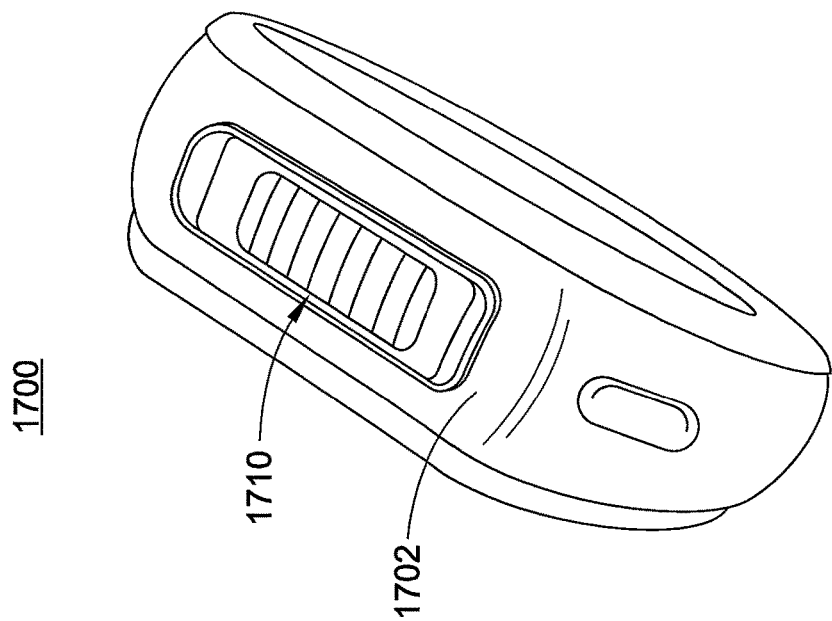
FIG. 54 is a top view of a first variation on a final exemplary embodiment of an injection device of the present disclosure, in which the injection device is wearable and can communicate with an electronic accessory, such as a smartphone, tablet, or computer.
Figure 55:
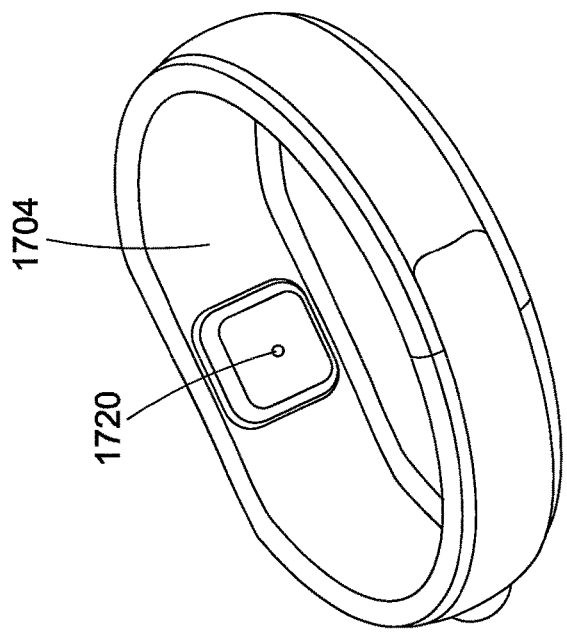
FIG. 55 is a bottom view of the first variation of FIG. 54.

FIG. 54 and FIG. 55 illustrate one variation in which the injection device has the form factor of a wristband, similar to that of FIG. 45 and FIG. 46. This variation may include two separate components as previously described, or may be one integrated component.

The injection device 1700 has an outer surface 1702 and an inner surface 1704. The user interface is present on the outer surface and includes the electronic display 1710 and other controls needed for the injection device. It is contemplated that the injection device is made from a flexible substrate, for comfort and fit. An injection pad or port 1720 is present on the inner surface (i.e. against the user's skin). The injection port contains a patch of microneedles attached to a drug reservoir (not visible) located within the injection device. In addition, the injection device contains electronic components for optimizing performance.

Figure 56:
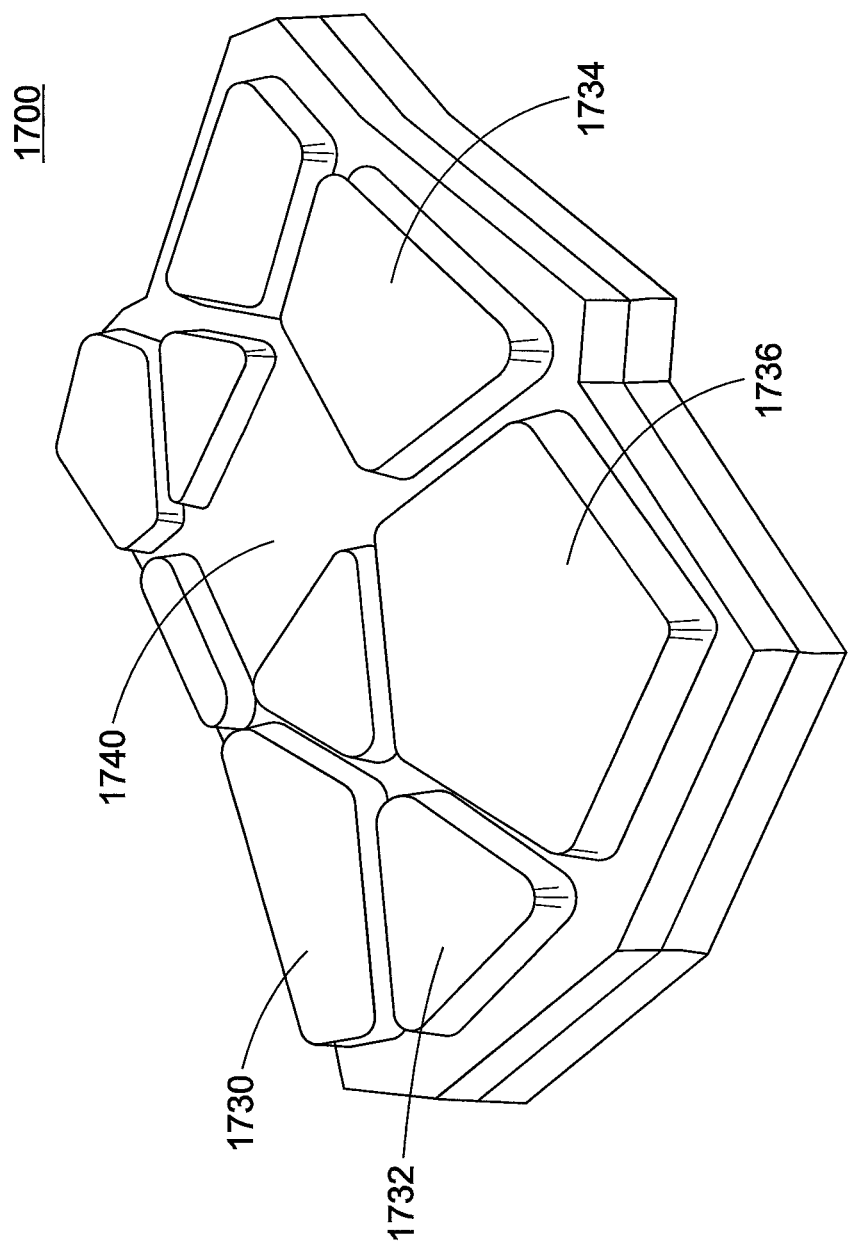
FIG. 56 is a perspective view of a second variation on the final exemplary embodiment, showing another embodiment of an injection device.

FIG. 56 is another embodiment of an injection device. As illustrated here, the injection device 1700 comprises a plurality of shaped injection pads 1730. Each pad includes a drug reservoir and a patch of microneedles to dispense the drug in the reservoir. Here, the pads are attached to a flexible substrate 1740. Each pad is differently shaped to permit flexing of the injection device. For example, some pads are triangular (1732), some are quadrilateral (1734), and some are pentagonal (1736). It is contemplated that such an injection device could be shaped into the form of regular clothing, such as shorts, tank tops, etc. A communications port (not illustrated) may be present on the injection device so that a smart device can be plugged in, or a wireless communications link may be provided.

Figure 57:
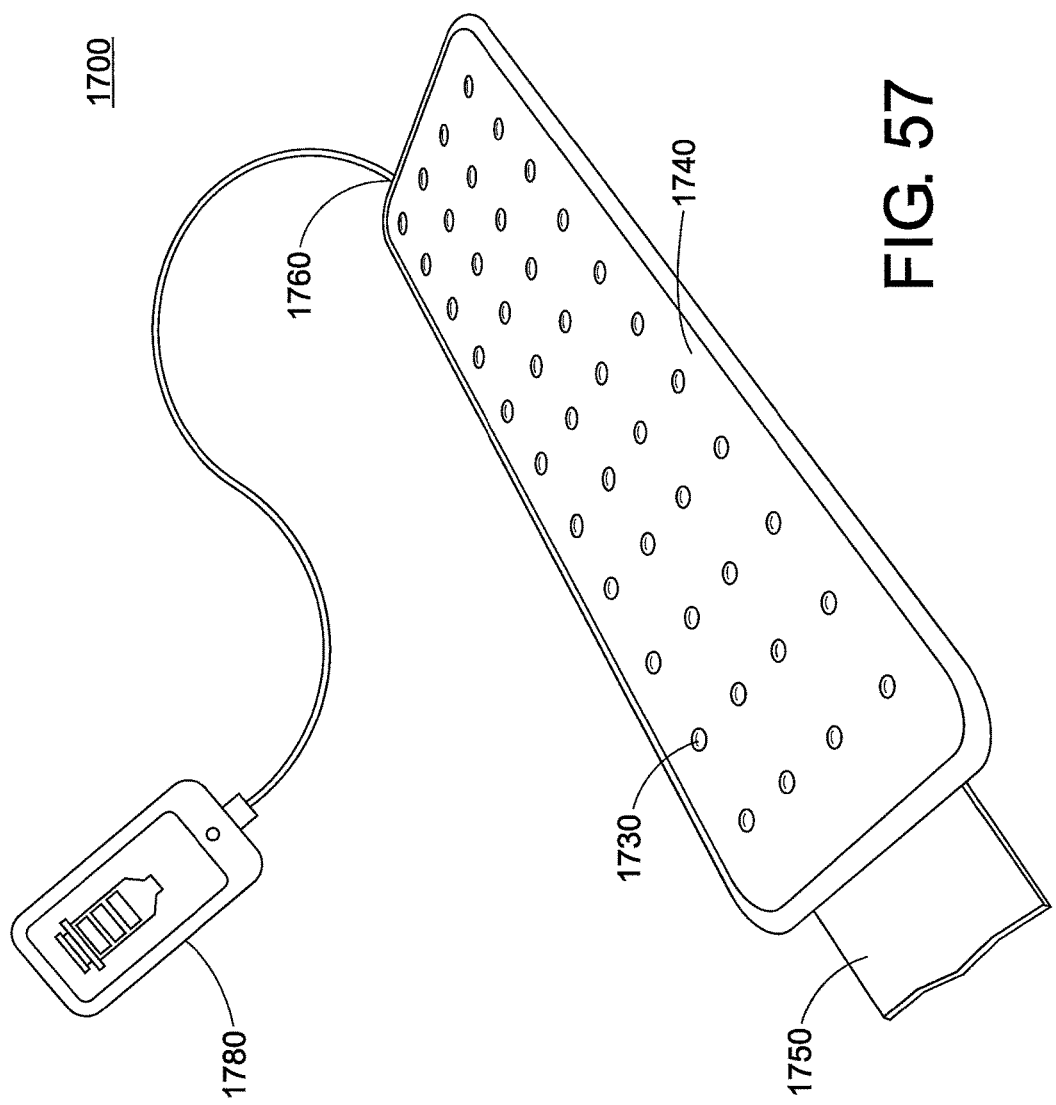
FIG. 57 is a perspective view of a third variation on the final exemplary embodiment, showing another embodiment of an injection device.

FIG. 57 is another embodiment of an injection device. As illustrated here, the injection device 1700 has a rectangular shape and comprises a plurality of injection pads 1730 which are attached to a flexible substrate 1740. The injection pads are arranged in a regular pattern. This embodiment is contemplated to be used in the form of an arm wrap, with a fastener 1750 being located on one end of the device that cooperates with another fastener on the substrate (e.g. a hook-and-loop fastener). Again, each pad includes a drug reservoir and a patch of microneedles to dispense the drug in the reservoir. Here, a communications port 1760 is illustrated into which the smart device 1780 can be plugged. The port is shown here located at the end opposite the fastener, though it can generally be located anywhere on the injection device.

It is contemplated that the injection device is used in conjunction with the smart device to upload personal information and received real-time diagnostic feedback for optimal dose performance. This information can be used to track and/or record the injection history of the user. The smart device becomes a user interface with the injection device when they are connected, either through a wired or wireless connection. The smart device can send information to the injection device such as a patient ID, dose settings (time, amount, etc.), reminders to take a dose, and other data settings for the injection device. In turn, the injection device can send information to the smart device such as the dose history, patient ID, etc. Such software and communications methods are conventional. The user interface and software residing on the smart device minimizes the cost and complexity of the injection device itself, providing upgradeable and expandable software features to enhance functionality.

All of the various injection devices described herein may contain various electronic components for communicating with other medical instruments. For example, the injection device might contain a RFID tag that contains information such as the dose amount, a time stamp for the injection, the manufacturer, the batch from which the medication was manufactured, the device serial number, and other tracking information.

The devices described herein can be made using materials and methods known in the art. The processes and devices described herein may be used to deliver a high-viscosity fluid containing protein microparticles made using the processes described in U.S. Provisional Patent Application Ser. No. 61/556,047, filed Nov. 4, 2011, the disclosure of which is hereby incorporated by reference in its entirety. The devices described herein may also use the core annular flow processes and devices described in U.S. Provisional Patent Application Ser. No. 61/556,491, filed on Nov. 7, 2011, and in U.S. Provisional Patent Application Ser. No. 61/673,864, filed on Jul. 20, 2012, the disclosures of which are hereby incorporated by reference in their entirety. They can also be used as part of the systems described in U.S. Provisional Patent Application Ser. No. 61/556,542, filed Nov. 4, 2011, the disclosure of which is hereby incorporated by reference in their entirety. They can also be dispensed using the chemical reaction systems and devices described in U.S. Provisional Patent Application Ser. No. 61/713,236, filed Oct. 12, 2012 or U.S. Provisional Patent Application Ser. No. 61/713,250, filed Oct. 12, 2012, the disclosures of which are hereby incorporated by reference in their entirety.

The present disclosure has been described with reference to several exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An injection device for delivering a fluid to a patient, comprising:
a plunger including a plunger handle and a piston;
a housing having a top end and a base end that has an orifice;
a barrel located within the housing for containing a fluid; and
a lower flange extending radially from the base end of the housing;
wherein the plunger handle has a gripping end with an external grip, and the piston is movably positioned within the barrel for dispensing the fluid from the barrel, the plunger further including a sidewall configured to interact with the plunger handle, wherein in an initial state the plunger handle is adapted to move relative to the sidewall and away from the lower flange to latch to the sidewall, and when latched to the sidewall the plunger handle is depressible towards the lower flange to start an injection process wherein fluid is dispensed from the barrel by the piston through the orifice.

2. The injection device of claim 1, wherein the lower flange is a deformable material capable of creating suction when the plunger handle is pulled away from the lower flange.

3. The injection device of claim 1, wherein the housing has a right circular conical shape.

4. The injection device of claim 1, wherein the plunger handle includes a hollow shaft that surrounds a lower channel sidewall of the housing, the shaft having a bottom end and a top end, the lower channel sidewall of the housing being slidably received within the bottom end of the shaft, the barrel being positioned within the lower channel sidewall.

5. The injection device of claim 1, wherein the top end of the housing includes an opening for receiving the plunger handle.

6. The injection device of claim 1, the sidewall including an exterior surface that interacts with the plunger handle, wherein the plunger handle is adapted to move together with the sidewall when the plunger handle is latched to the sidewall, and the sidewall is prevented from moving away from the lower flange when the plunger handle is moved in the initial state.

7. The injection device of claim 6, wherein the plunger handle includes a latching end having a tongue that engages a groove of the sidewall to join the plunger handle and the sidewall together.

8. The injection device of claim 6, wherein the housing includes a lower channel sidewall extending from the base end, and the sidewall is adapted to move down the lower channel sidewall during a depression of the plunger handle towards the lower flange when the plunger handle is latched to the sidewall.

9. The injection device of claim 1, further comprising a needle coupled to an end of the barrel and configured to dispense the fluid from the barrel during the injection process, wherein in the initial state the needle does not protrude from the base end of the housing, and the needle is configured to protrude through the base end of the housing when the plunger handle is pushed towards the lower flange while latched to the sidewall.

10. The injection device of claim 9, wherein the needle retracts into the housing in response to the plunger handle reaching an end of a push stroke while latched to the sidewall.

11. The injection device of claim 9, wherein when latched to the sidewall the plunger handle is moveable from a first level to second level, wherein when the plunger handle is at the first level the plunger is operative to push the barrel downwards to cause the needle to extend out of the housing, and the piston moves with the barrel prior to the plunger handle reaching the second level, and when the plunger handle is at the second level the plunger is operative to begin depressing the piston through the barrel to dispense fluid through the needle.

12. The injection device of claim 1, wherein in the initial state a latching end of the plunger handle is adapted to slide on an exterior surface of the sidewall.

13. The injection device of claim 12, wherein the width of the lower flange is at least twice the width of the base end of the housing.

14. The injection device of claim 1, wherein the piston is not moved within the barrel during movement of the plunger handle in the initial state, and the plunger is operative to push the piston through the barrel when the plunger handle is latched to the sidewall.

15. The injection device of claim 1, wherein the external grip is ring shaped.

* * * * *